(12) United States Patent
Allen et al.

(10) Patent No.: US 8,420,631 B2
(45) Date of Patent: Apr. 16, 2013

(54) 6-SUBSTITUTED-2,3,4,5-TETRAHYDRO-1H-BENZO[D]AZEPINES AS 5-HT$_{2C}$ RECEPTOR AGONISTS

(75) Inventors: John Gordon Allen, Newbury Park, CA (US); Karin Briner, Indianapolis, IN (US); Anne Marie Camp, Basingstoke (GB); Manuel Javier Cases-Thomas, Basingstoke (GB); Richard Charles Hoying, Plainfield, IN (US); Maria Angeles Martinez-Grau, Alcobendas (ES); Michael Philip Mazanetz, Basingstoke (GB); Natalia Pokrovskaia, New Westminster (CA); Richard Edmund Rathmell, Basingstoke (GB); Roger Ryan Rothhaar, Reelsville, IN (US); Selma Sapmaz, Basingstoke (GB); Andrew Caerwyn Williams, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 1066 days.

(21) Appl. No.: 11/995,344

(22) PCT Filed: Sep. 1, 2006

(86) PCT No.: PCT/US2006/034430
§ 371 (c)(1),
(2), (4) Date: Jan. 11, 2008

(87) PCT Pub. No.: WO2007/028131
PCT Pub. Date: Mar. 8, 2007

(65) Prior Publication Data
US 2008/0207897 A1 Aug. 28, 2008

Related U.S. Application Data

(60) Provisional application No. 60/713,584, filed on Sep. 1, 2005.

(51) Int. Cl.
| | | |
|---|---|---|
| A61P 3/04 | (2006.01) | |
| A61P 25/00 | (2006.01) | |
| A61P 25/22 | (2006.01) | |
| A61P 25/24 | (2006.01) | |
| A61K 31/55 | (2006.01) | |
| C07D 223/16 | (2006.01) | |
| C07D 401/06 | (2006.01) | |
| C07D 403/04 | (2006.01) | |
| C07D 409/04 | (2006.01) | |
| C07D 417/06 | (2006.01) | |

(52) U.S. Cl.
USPC .................................. 514/217.01; 540/594

(58) Field of Classification Search ............. 514/217.01; 540/594
See application file for complete search history.

(56) References Cited

U.S. PATENT DOCUMENTS
| | | | |
|---|---|---|---|
| 4,265,890 A | 5/1981 | Holden et al. | |
| 4,985,352 A | 1/1991 | Julius et al. | |
| 5,639,748 A | 6/1997 | DeMarinis et al. | |
| 5,698,766 A | 12/1997 | Julius et al. | |

FOREIGN PATENT DOCUMENTS
| | | |
|---|---|---|
| EP | 0285 287 | 10/1988 |
| EP | 1213017 A2 | 6/2002 |
| WO | WO 93/03015 | 2/1993 |
| WO | WO 93/04686 | 3/1993 |
| WO | WO 93/04866 | 3/1993 |
| WO | WO 02/074746 | 9/2002 |
| WO | WO/02/074746 | 9/2002 |
| WO | WO 03 006466 | 1/2003 |
| WO | WO 03/045940 | 6/2003 |
| WO | WO 03/086306 | 10/2003 |
| WO | WO 2005/003096 | 1/2005 |
| WO | WO 2005/019179 | 3/2005 |
| WO | WO 2005/019180 | 3/2005 |
| WO | WO 2005/042490 | 5/2005 |
| WO | WO 2005/042491 | 5/2005 |
| WO | WO 2005/082859 | 9/2005 |
| WO | WO 2006/069363 | 6/2006 |
| WO | WO 2006/071740 | 7/2006 |

OTHER PUBLICATIONS

Vikers et al., Psycholpharmacology, 167: 274-280 (2003).
Tecott et al., Nature, 374: 542-546 (1995).
Martin et al., Pharmacol. Biochem. Behav., 71: 615 (2002).
Chou-Green et al., Physiology & Behavior, 78: 641-649 (2003).
Leysen et al., Trends in Drug Research II, 29: 49-61 (1998).
Frank et al., Neuropsychopharmacology 27: 869-873 (2002).
Upton et al., Eur. J. Pharmacol., 359:33 (1998).
Fitzgerald, Ennis, Annual Reports in Medicinal Chemistry, 37: 21-30 (2002).
Nelson et al., Naunyn-Schmiedeberg's Arch. Pharm., 359: 1-6 (1999).
V. Setola et al., Mol. Pharmacology, 63: 1223-1229 (2003).
Frishman, Kotob, Journal of Clinical Pharmacology, 39: 7-16 (1999).
Seeman, Van Tol, Trends in Pharmacological Sciences, 15: 264-270 (1994).
Data Base Registry: XP002419374, Sep. 30, 2005.
Database Registry: XP002419375, Sep. 30, 2005.
Database Registry: XP002419376, Sep. 30, 2005.
Database Registry: XP002419377, Sep. 30, 2005.
M. Catret et al., The 5-HT and alpha-Adrenoceptor Antagonist Effect of Four Benzylisoquinoline Alkaloids on Rat Aorta, J. Pharm. Pharmacol. 1998, 50, pp. 317-322.

Primary Examiner — Brenda Coleman
(74) Attorney, Agent, or Firm — R. Craig Tucker

(57) ABSTRACT

The present invention provides 6-substituted 2,3,4,5-tetrahydro-1H-benzo[d]azepines of Formula (I) as selective 5-HT$_{2C}$ receptor agonists for the treatment of 5-HT$_{2C}$ associated disorders including obesity, obsessive/compulsive disorder, depression, and anxiety: where $R^6$ is —C≡C—$R^{10}$, —CH=CR$^{11}$R$^{11'}$, or —(C$_0$-C$_8$)alkyl-Ar$^2$ optionally substituted on the alkyl moiety with 1 to 6 fluoro substituents and other substituents are as defined in the specification.

5 Claims, No Drawings

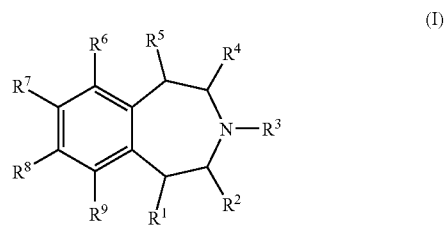

(I)

6-SUBSTITUTED-2,3,4,5-TETRAHYDRO-1H-BENZO[D]AZEPINES AS 5-HT$_{2C}$ RECEPTOR AGONISTS

This U.S. national stage application of International Application PCT/US2006/034430, filed Sep. 1, 2006, claims priority to U.S. provisional application Ser. No. 60/713584, filed Sep. 1, 2005.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2A}$, 5-HT$_{2B}$, and 5-HT$_{2C}$. The 5-HT$_{2C}$ receptor has been isolated and characterized (Julius, et al., U.S. Pat. No. 4,985,352), and transgenic mice lacking the 5-HT$_{2C}$ receptor have been reported to exhibit seizures and an eating disorder resulting in increased consumption of food (Julius et al., U.S. Pat. No. 5,698,766). The 5-HT$_{2C}$ receptor has also been linked to various other neurological disorders including obesity (Vickers et al., Psychopharmacology, 167: 274-280 (2003)), hyperphagia (Tecott et al., Nature, 374: 542-546 (1995)), obsessive compulsive disorder (Martin et al., Pharmacol. Biochem. Behav., 71: 615 (2002); Chou-Green et al., Physiology & Behavior, 78: 641-649 (2003)), depression (Leysen, Kelder, Trends in Drug Research II, 29: 49-61 (1998)), anxiety (Curr. Opin. Invest. Drugs 2(4), p. 317 (1993)), substance abuse, sleep disorder (Frank et al., Neuropsychopharmacology 27: 869-873 (2002)), hot flashes (EP 1213017 A2), epilepsy (Upton et al., Eur. J. Pharmacol., 359: 33 (1998); Fitzgerald, Ennis, Annual Reports in Medicinal Chemistry, 37: 21-30 (2002)), and hypogonadism (Curr. Opin. Invest. Drugs 2(4), p. 317 (1993)).

Certain substituted 2,3,4,5-tetrahydro-1H-benzo[d]azepine compounds have been disclosed as useful therapeutics as for example:

U.S. Pat. No. 4,265,890 describes certain substituted 2,3,4,5-tetrahydro-1H-benzo[d]azepine compounds as dopaminergic receptor antagonists for use as antipsychotics and antiemetics, inter alia.

EP 0 285 287 describes certain substituted 2,3,4,5-tetrahydro-1H-benzo[d]azepine compounds for use as agents to treat gastrointestinal motility disorders, inter alia.

WO 93/03015 and WO 93/04686 describe certain substituted 2,3,4,5-tetrahydro-1H-benzo[d]azepine compounds as alpha-adrenergic receptor antagonists for use as agents to treat hypertension and cardiovascular diseases in which changes in vascular resistance are desirable, inter alia.

WO 02/074746 A1 describes certain substituted 2,3,4,5-tetrahydro-1H-benzo[d]azepine compounds as 5-HT$_{2C}$ agonists for the treatment of hypogonadism, obesity, hyperphagia, anxiety, depression, sleep disorder, inter alia.

WO 03/006466 A1 describes certain substituted tricyclic hexahydroazepinoindole and indoline compounds as 5-HT ligands and consequently their usefulness for treating diseases wherein modulation of 5-HT activity is desired.

WO 05/019180 describes 6-(2,2,2-trifluoroethylamino)-7-chloro-2,3,4,5-tetrahydro-1H-benzo[d]azepine as a potent and selective 5-HT$_{2C}$ agonist for the treatment of inter alia obesity, anxiety, depression, and obsessive-compulsive disorder.

High affinity 5-HT$_{2C}$ receptor agonists would provide useful therapeutics for the treatment of the above mentioned 5-HT$_{2C}$ receptor-associated disorders including obesity, hyperphagia, obsessive/compulsive disorder, depression, anxiety, substance abuse, sleep disorder, hot flashes, and hypogonadism. High affinity 5-HT$_{2C}$ receptor agonists that are also selective for the 5-HT$_{2C}$ receptor, would provide such therapeutic benefit without the undesirable adverse events associated with current therapies. Achieving selectivity for the 5-HT$_{2C}$ receptor, particularly as against the 5-HT$_{2A}$ and 5-HT$_{2B}$ receptors, has proven difficult in designing 5-HT$_{2C}$ agonists. 5-HT$_{2A}$ receptor agonists have been associated with problematic hallucinogenic adverse events. (Nelson et al., Naunyn-Schmiedeberg's Arch. Pharm., 359: 1-6 (1999)). 5-HT$_{2B}$ receptor agonists have been associated with cardiovascular related adverse events, such as valvulopathy. (V. Setola et al., Mol. Pharmacology, 63: 1223-1229 (2003), and ref. cited therein).

Previous references to substituted 2,3,4,5-tetrahydro-1H-benzo[d]azepine compounds as potential therapeutics have predominantly recited their uses as alpha adrenergic and/or dopaminergic modulators. Adrenergic modulators are often associated with the treatment of cardiovascular diseases (Frishman, Kotob, Journal of Clinical Pharmacology, 39: 7-16 (1999)). Dopaminergic receptors are primary targets in the treatment of schizophrenia and Parkinson's disease (Seeman, Van Tol, Trends in Pharmacological Sciences, 15: 264-270 (1994)). It will be appreciated by those skilled in the art that selectivity as against these and other physiologically important receptors will generally also be preferred characteristics for therapeutics for the specific treatment of 5-HT$_{2C}$ associated disorders as described above.

The present invention provides selective 5-HT$_{2C}$ agonist compounds of Formula I:

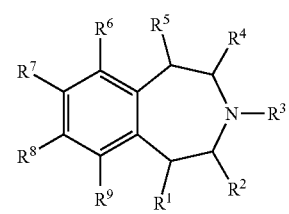

where:
$R^1$ is hydrogen, fluorine, or (C$_1$-C$_3$)alkyl;
$R^2$, $R^3$, and $R^4$ are each independently hydrogen, methyl, or ethyl;
$R^5$ is hydrogen, fluorine, methyl, or ethyl;
$R^6$ is —C≡C—R$^{10}$, —CH═CR$^{11}$R$^{11'}$, —(C$_0$-C$_8$)alkyl-Ar$^2$ optionally substituted on the alkyl moiety with 1 to 6 fluoro substituents, —(C$_0$-C$_8$)alkyl-Het$^1$ optionally substituted on the alkyl moiety with 1 to 6 fluoro substituents, or —(C$_1$-C$_5$)alkyl-N(R$^{13}$)C(O)—R$^{12}$ optionally substituted on the alkyl moiety with 1 to 6 fluoro substituents;
$R^7$ is hydrogen, halo, cyano, (C$_1$-C$_6$)alkyl optionally substituted with 1 to 6 fluoro substituents, (C$_2$-C$_6$)alkenyl optionally substituted with 1 to 6 fluoro substituents, (C$_1$-C$_6$)alkoxy optionally substituted with 1 to 6 fluoro substituents, or (C$_1$-C$_6$)alkylthio optionally substituted with 1 to 6 fluoro substituents;
$R^8$ is hydrogen, halo, cyano, hydroxy, or —SCF$_3$;
$R^9$ is hydrogen, halo, cyano, hydroxy, —CF$_3$, —SCF$_3$, or (C$_1$-C$_3$)alkoxy optionally substituted with 1 to 6 fluoro substituents;
$R^{10}$ is Het$^1$-(C$_1$-C$_5$)alkyl optionally substituted on the alkyl moiety with 1 to 6 fluorine substituents,
$R^{12}$—C(O)N(R$^3$)—(C$_1$-C$_5$)alkyl optionally substituted on the alkyl moiety with 1 to 6 fluorine substituents,
$R^{14}R^{15}$NC(O)—NR$^{13}$—(C$_1$-C$_5$)alkyl optionally substituted on the alkyl moiety with 1 to 6 fluorine substituents, $R^{14}R^{15}NC(O)$—O—$(C_1-C_5)$alkyl optionally substituted on the alkyl moiety with 1 to 6 fluorine substituents, $R^{14}R^{15}NC(O)$—$(C_1-C_5)$alkyl optionally substituted on the alkyl moiety with 1 to 6 fluorine substituents, $(C_1-C_6)$alkoxy-$(C_1-C_5)$alkyl optionally substituted on the alkoxy and alkyl moieties independently with 1 to 6 fluoro substituents, $(C_3-C_7)$cycloalkyloxy-$(C_1-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkoxy-$(C_1-C_5)$alkyl optionally substituted on the alkoxy and alkyl moieties independently with 1 to 6 fluoro substituents, $Ar^4$—$(C_0-C_3)$alkoxy-$(C_1-C_5)$alkyl optionally substituted on the alkoxy and alkyl moieties independently with 1 to 6 fluoro substituents, $(C_1-C_6)$alkyl-S—$(C_1-C_5)$alkyl optionally substituted on each alkyl moiety independently with 1 to 6 fluoro substituents, $(C_3-C_7)$cycloalkyl-S—$(C_1-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkyl-S—$(C_1-C_5)$alkyl optionally substituted on each alkyl moiety independently with 1 to 6 fluoro substituents, $Ar^4$—$(C_0-C_3)$alkyl-S—$(C_1-C_5)$alkyl optionally substituted on each alkyl moiety independently with 1 to 6 fluoro substituents, $(C_1-C_6)$alkyl-$SO_2$—$(C_1-C_8)$alkyl optionally substituted on each alkyl moiety independently with 1 to 6 fluoro substituents, $(C_3-C_7)$cycloalkyl-$SO_2$—$(C_1-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkyl-$SO_2$—$(C_1-C_5)$alkyl optionally substituted on each alkyl moiety independently with 1 to 6 fluoro substituents, $Ar^4$—$(C_0-C_3)$alkyl-$SO_2$—$(C_1-C_5)$alkyl optionally substituted on each alkyl moiety independently with 1 to 6 fluoro substituents, $(C_1-C_6)$alkyl-C(O)—$(C_1-C_5)$alkyl optionally substituted on each alkyl moiety independently with 1 to 6 fluoro substituents, $(C_3-C_7)$cycloalkyl-C(O)—$(C_1-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkyl-C(O)—$(C_1-C_5)$alkyl optionally substituted on each alkyl moiety independently with 1 to 6 fluoro substituents, or $Ar^4$—$(C_0-C_3)$alkyl-C(O)—$(C_1-C_5)$alkyl optionally substituted on each alkyl moiety independently with 1 to 6 fluoro substituents;

$R^{11}$ is $Ar^1$—$(C_0-C_3)$alkyl optionally substituted on the alkyl moiety with 1 to 6 fluoro substituents, $Ph^2$-$(C_0-C_3)$alkyl optionally substituted on the alkyl moiety with 1 to 6 fluoro substituents, $R^{12}$—C(O)N($R^{13}$)—$(C_1-C_5)$alkyl optionally substituted on the alkyl moiety with 1 to 6 fluoro substituents, or $Het^1$-$(C_1-C_5)$alkyl optionally substituted on the alkyl moiety with 1 to 6 fluoro substituents;

$R^{11'}$ is hydrogen or methyl;

$R^{12}$ is $(C_1-C_6)$alkyl optionally substituted with 1 to 6 fluoro substituents;

$(C_3-C_7)$cycloalkyl$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $(C_1-C_6)$alkoxy-$(C_0-C_5)$alkyl optionally substituted on the alkoxy and alkyl moieties independently with 1 to 6 fluoro substituents, $(C_3-C_7)$cycloalkyloxy-$(C_0-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $(C_1-C_6)$alkyl-S—$(C_0-C_5)$alkyl optionally substituted on each alkyl moiety independently with 1 to 6 fluoro substituents, $(C_3-C_7)$cycloalkyl-S—$(C_1-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkyl optionally substituted on the alkyl moiety with 1 to 6 fluoro substituents, or $Ar^4$—$(C_0-C_3)$alkyl optionally substituted on the alkyl moiety with 1 to 6 fluoro substituents;

$R^{13}$ is hydrogen or $(C_1-C_3)$alkyl optionally substituted with 1 to 6 fluoro substituents;

$R^{14}$ is $(C_1-C_6)$alkyl optionally substituted with 1 to 6 fluoro substituents;

$(C_3-C_7)$cycloalkyl$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $(C_1-C_6)$alkoxy-$(C_1-C_5)$alkyl optionally substituted on the alkoxy and alkyl moieties independently with 1 to 6 fluoro substituents, $(C_3-C_7)$cycloalkyloxy-$(C_1-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, ($C_1$-$C_6$)alkyl-S—($C_1$-$C_5$)alkyl optionally substituted on the alkyl moieties independently with 1 to 6 fluoro substituents, ($C_3$-$C_7$)cycloalkylthio-($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, $Ph^3$-($C_0$-$C_3$)alkyl optionally substituted on the alkyl moiety with 1 to 6 fluoro substituents, or $Ar^4$—($C_0$-$C_3$)alkyl optionally substituted on the alkyl moiety with 1 to 6 fluoro substituents;

$R^{15}$ is hydrogen or ($C_1$-$C_3$)alkyl optionally substituted with 1 to 6 fluoro substituents, or $R^{14}$ and $R^{15}$ may be taken together with the nitrogen atom to which they are attached to form $Het^2$;

$Ar^1$ is an aromatic heterocycle substituent selected from the group consisting of pyrrolyl furanyl, thiophenyl, thiazolyl, isothiazolyl, oxazolyl, isoxazolyl and pyridyl, any of which may optionally be substituted with 1 to 3 substituents independently selected from the group consisting of halo, ($C_1$-$C_3$)alkyl, ($C_1$-$C_3$)alkoxy, —$CF_3$, —O—$CF_3$, nitro, cyano, hydroxy and —$SCF_3$, wherein when $Ar^1$ is pyridyl, said pyridyl may alternatively, optionally be substituted with
  i) 1 to 4 independently selected halo substituents; or
  ii) 1 to 3 substituents independently selected from the group consisting of halo, cyano, and hydroxy, methyl, —$CF_3$, and methoxy; or
  iii) 0, 1, or 2 substituents independently selected from the group consisting of halo, cyano, and hydroxy, methyl, —$CF_3$, and methoxy, and further substituted with one substituent selected from the group consisting of ($C_1$-$C_6$)alkyl optionally substituted with 1 to 6 fluoro substituents, ($C_1$-$C_6$)alkoxy-($C_0$-$C_3$)alkyl optionally substituted on the alkoxy and alkyl moieties independently with 1 to 6 fluoro substituents, ($C_3$-$C_7$)cycloalkyloxy-($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally further substituted with 1 to 6 fluoro substituents, provided that no more than 2 of the substituents on the cycloalkyl moiety are alkyl, ($C_1$-$C_6$)alkyl-S—($C_0$-$C_3$)alkyl optionally substituted on the alkyl moieties independently with 1 to 6 fluoro substituents, ($C_3$-$C_7$)cycloalkylthio($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-$SO_2$—($C_0$-$C_3$)alkyl optionally substituted on the alkyl moieties independently with 1 to 6 fluoro substituents, ($C_3$-$C_7$)cycloalkyl-$SO_2$—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-C(O)—($C_0$-$C_3$)alkyl optionally substituted on the alkyl moieties independently with 1 to 6 fluoro substituents, ($C_3$-$C_7$)cycloalkyl-C(O)—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-C(O)NH—($C_0$-$C_3$)alkyl optionally substituted on the alkyl moieties independently with 1 to 6 fluoro substituents, ($C_3$-$C_7$)cycloalkyl-C(O)NH—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-NHC(O)—($C_0$-$C_3$)alkyl optionally substituted on the alkyl moieties independently with 1 to 6 fluoro substituents, and ($C_3$-$C_7$)cycloalkyl-NHC(O)—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl;

$Ar^2$ is an aromatic group linked through carbon selected from the list consisting of phenyl, naphthyl, pyrrolyl, 1,2,3-triazolyl, thiophenyl, thiazolyl, isothiazolyl, oxazolyl, isoxazolyl and pyridyl, any one of which may be optionally substituted with 1 to 5 independently selected halo substituents, or with 1 to 3 substituents independently selected from the group consisting of halo, cyano, phenyl, hydroxy, ($C_1$-$C_6$)alkyl optionally further substituted with 1 to 6 fluoro substituents, ($C_1$-$C_6$)alkoxy optionally further substituted with 1 to 6 fluoro substituents, ($C_1$-$C_6$)alkylthio optionally further substituted with 1 to 6 fluoro substituents, ($C_1$-$C_6$)alkyl-$NR^{13}$—($C_1$-$C_3$)alkyl optionally further substituted on an alkyl moiety with 1 to 6 fluoro substituents, ($C_3$-$C_7$)cycloalkyl-($C_0$-$C_3$)alkyl-$NR^{13}$—($C_1$-$C_3$)alkyl optionally further substituted on an alkyl moiety with 1 to 6 fluoro substituents, ($C_1$-$C_6$)alkyl-C(O)$NR^{13}$—($C_1$-$C_3$)alkyl optionally further substituted on an alkyl moiety with 1 to 6 fluoro substituents, and ($C_3$-$C_7$)cycloalkyl-($C_0$-$C_3$)alkyl-$NR^{13}$—($C_1$-$C_3$)alkyl optionally further substituted on an alkyl moiety with 1 to 6 fluoro substituents;

$Ar^3$ is pyridyl optionally substituted with 1 to 4 independently selected halo substituents, or with 1 to 3 substituents independently selected from the group consisting of halo, cyano, hydroxy, —$SCF_3$, ($C_1$-$C_6$)alkyl optionally further substituted with 1 to 6 fluoro substituents, and ($C_1$-$C_6$) alkoxy optionally further substituted with 1 to 6 fluoro substituents;

$Ar^4$ is pyridyl optionally substituted with 1 to 4 independently selected halo substituents, or with 1 to 3 substituents independently selected from the group consisting of halo, cyano, hydroxy, ($C_1$-$C_6$)alkyl optionally further substituted with 1 to 6 fluoro substituents, ($C_1$-$C_6$)alkoxy optionally further substituted with 1 to 6 fluoro substituents, ($C_1$-$C_6$)alkylthio optionally further substituted with 1 to 6 fluoro substituents, $(C_1-C_6)$alkylsulfonyl, $(C_1-C_6)$alkyl-C(O)—, and $(C_1-C_6)$alkyl-NHC(O)—;

Het$^1$ is a heterocycle, linked through either carbon or nitrogen, selected from the group consisting of pyrazolyl, pyrazolinyl, pyrazolidinyl, imidazolyl, imidazolinyl, imidazolidinyl, thiazolyl, thiazolinyl, thiazolidinyl, oxazolyl, oxazolinyl, oxazolidinyl, pyrrolyl, pyrrolinyl, pyrrolidinyl, 1,2,4-triazolyl, 1,3,4-triazolyl, piperidyl, tetrahydropyridyl, dihydropyridyl, piperazinyl, tetrahydropyrazinyl, dihydropyrazinyl, hexahydropyrimidyl, tetrahydropyrimidyl, dihydropyrimidyl, morpholinyl, thiomorpholinyl, homomorpholinyl, homopiperidinyl, indazolyl, indazolinyl, benzimidazolyl, benzimidazolinyl, benzothiazolyl, benzothiazolinyl, benzoxazolyl, benzoxazolinyl, indolyl, indolinyl, isoindolyl, isoindolinyl, benzotriazolyl, dihydroquinolinyl, tetrahydroquinolinyl, dihydroisoquinolinyl, tetrahydroisoquinolinyl, dihydroquinazolinyl, tetrahydroquinazolinyl, dihydroquinoxalinyl, tetrahydroquinoxalinyl, benzoxazinyl, benzothiazinyl, benzazepinyl, and benzoxazepinyl, any one of which may be optionally substituted on carbon atoms of the heterocyclic ring with 1 to 2 oxo substituents, and independently optionally substituted on either carbon or nitrogen atoms of the heterocyclic ring, with 1 to 2 substituents independently selected from the group consisting of $(C_1-C_6)$alkyl optionally further substituted with 1 to 6 fluoro substituents, Ph$^1$-$(C_0-C_3)$alkyl optionally further substituted on the alkyl moiety with 1 to 6 fluoro substituents, and Ar$^3$—$(C_0-C_3)$alkyl optionally further substituted on the alkyl moiety with 1 to 6 fluoro substituents, or two adjacent substituents taken together with the heterocyclic ring atoms to which they are attached form a 5- or 6-membered saturated or partially saturated ring;

Het$^2$ is a saturated, nitrogen-containing heterocycle substituent selected from the group consisting of pyrrolidinyl, piperidinyl, homopiperidinyl, morpholinyl, thiomorpholinyl, homomorpholinyl, homothiomorpholinyl, and piperazine, any one of which may optionally be substituted with $(C_2-C_6)$alkyl optionally substituted with 1 to 6 fluoro substituents, or with 1 to 2 methyl substituents each optionally substituted with 1 to 3 fluoro substituents;

Ph$^1$ is phenyl optionally substituted with 1 to 5 independently selected halo substituents, or with 1 to 3 substituents independently selected from the group consisting of halo, cyano, —SCF$_3$, hydroxy, $(C_1-C_6)$alkyl optionally further substituted with 1 to 6 fluoro substituents, and $(C_1-C_6)$alkoxy optionally further substituted with 1 to 6 fluoro substituents;

Ph$^2$ is phenyl optionally substituted with
i) 1 to 5 independently selected halo substituents; or
ii) 1 to 3 substituents independently selected from the group consisting of halo, cyano, hydroxy, methyl, methoxy, and —CF$_3$; or
iii) 0, 1 or 2 substituents independently selected from the group consisting of halo, cyano, hydroxy, methyl, methoxy, and —CF$_3$, and further substituted with one substituent selected from the group consisting of
$(C_1-C_6)$alkyl optionally substituted with 1 to 6 fluoro substituents,
$(C_1-C_6)$alkoxy-$(C_0-C_3)$alkyl optionally substituted on the alkoxy and alkyl moieties independently with 1 to 6 fluoro substituents,
$(C_3-C_7)$cycloalkyloxy-$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-S—$(C_0-C_3)$alkyl optionally substituted on the alkyl moieties independently with 1 to 6 fluoro substituents,
$(C_3-C_7)$cycloalkylthio$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-SO$_2$—$(C_0-C_3)$alkyl optionally substituted on the alkyl moieties independently with 1 to 6 fluoro substituents,
$(C_3-C_7)$cycloalkyl-SO$_2$—$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-C(O)—$(C_0-C_3)$alkyl optionally substituted on the alkyl moieties independently with 1 to 6 fluoro substituents,
$(C_3-C_7)$cycloalkyl-C(O)—$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-C(O)NH—$(C_0-C_3)$alkyl optionally substituted on the alkyl moieties independently with 1 to 6 fluoro substituents,
$(C_3-C_7)$cycloalkyl-C(O)NH—$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-NHC(O)—$(C_0-C_3)$alkyl optionally substituted on the alkyl moieties independently with 1 to 6 fluoro substituents, and
$(C_3-C_7)$cycloalkyl-NHC(O)—$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl;

Ph$^3$ is phenyl optionally substituted with 1 to 5 independently selected halo substituents, or with 1 to 3 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylsulfonyl, $(C_1-C_6)$alkyl-C(O)—, and $(C_1-C_6)$alkyl-NHC(O)—;

or a pharmaceutically acceptable salt or solvate thereof.

This invention also provides pharmaceutical compositions which comprise a compound of Formula I, or a pharmaceutically acceptable salt thereof, in association with a pharmaceutically acceptable carrier, diluent, or excipient.

In another aspect of the present invention, there is provided a method for increasing activation of the 5-HT$_{2C}$ receptor in mammals comprising administering to a mammal in need of such activation an effective amount of a compound of Formula I, or a pharmaceutically acceptable salt thereof.

The present invention also provides a method for treating obesity in mammals comprising administering to a mammal in need of such treatment an effective amount of a compound of Formula I, or a pharmaceutically acceptable salt thereof.

The present invention also provides a method for treating obsessive/compulsive disorder in mammals comprising administering to a mammal in need of such treatment an effective amount of a compound of Formula I, or a pharmaceutically acceptable salt, thereof.

Furthermore, the present invention provides a method for treating depression in mammals comprising administering to a mammal in need of such treatment an effective amount of a compound of Formula I, or a pharmaceutically acceptable salt thereof.

Furthermore, the present invention provides a method for treating anxiety in mammals comprising administering to a mammal in need of such treatment an effective amount of a compound of Formula I, or a pharmaceutically acceptable salt thereof.

In preferred embodiments of the above methods of treatment utilizing a compound of Formula I, or a pharmaceutically acceptable salt thereof, the mammal is a human.

In another aspect of the present invention, there is provided a compound of Formula I for use in selectively increasing activation of the 5-HT$_{2C}$ receptor and/or for use in treating a variety of disorders associated with decreased activation of 5-HT$_{2C}$ receptors. Preferred embodiments of this aspect of the invention include a compound of Formula I for use in the treatment of obesity, hyperphagia, obsessive/compulsive disorder, depression, anxiety, substance abuse, sleep disorder, hot flashes, and/or hypogonadism. Particularly preferred embodiments of this aspect of the invention include the treatment of obesity, obsessive/compulsive disorder, depression, and/or anxiety.

In another aspect of the present invention, there is provided the use of one or more compounds of Formula I in the manufacture of a medicament for the activation of 5-HT$_{2C}$ receptors in a mammal. In preferred embodiments of this aspect of the invention, there is provided the use of one or more compounds of Formula I in the manufacture of a medicament for the treatment of obesity, hyperphagia, obsessive/compulsive disorder, depression, anxiety, substance abuse, sleep disorder, hot flashes, and/or hypogonadism. Particularly preferred embodiments of this aspect of the invention include the use of one or more compounds of Formula I in the manufacture of medicaments for the treatment of obesity, obsessive/compulsive disorder, depression, and/or anxiety.

Additionally, the present invention provides a pharmaceutical formulation adapted for the treatment of obesity, or for the treatment of obsessive/compulsive disorder, or for the treatment of depression, or for the treatment of anxiety, each of which comprise a compound of Formula I in association with a pharmaceutically acceptable carrier, diluent or excipient.

In those instances where the disorders which can be treated by 5-HT$_{2C}$ agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The general chemical terms used throughout have their usual meanings. For example, the term "alkyl" refers to a branched or unbranched saturated hydrocarbon group. The term "n-alkyl" refers to an unbranched alkyl group. By way of illustration, but without limitation, the term "(C$_1$-C$_2$)alkyl" refers to methyl and ethyl. The term "(C$_1$-C$_3$) n-alkyl" refers to methyl, ethyl, and propyl. The term "(C$_1$-C$_3$)alkyl" refers to methyl, ethyl, propyl, and isopropyl. The term "(C$_1$-C$_4$) n-alkyl" refers to methyl, ethyl, n-propyl, and 71-butyl. The term "(C$_1$-C$_4$)alkyl" refers to methyl, ethyl, propyl, isopropyl, n-butyl, isobutyl, sec-butyl, and tert-butyl. The term "(C$_1$-C$_6$)alkyl" refers to all branched and unbranched alkyl groups having from one to six carbon atoms. The term "(C$_3$-C$_6$)alkyl" refers to all branched and unbranched alkyl groups having from three to six carbon atoms. The term "(C$_2$-C$_6$)alkyl" refers to all branched and unbranched alkyl groups having from two to six carbon atoms.

(C$_x$-C$_y$)alkyl may also be used in conjunction with other substituents to indicate a branched or unbranched saturated hydrocarbon linker for the substituent, where x and y indicate the range of carbon atoms permitted in the linker moiety. By way of illustration, but without limitation, —(C$_0$-C$_1$)alkyl refers to a single bond or a methylene linker moiety; —(C$_0$-C$_3$)alkyl further includes trimethylene, alpha- or beta-methyl ethylene, dimethyl methylene, or ethyl methylene. —(C$_0$-C$_8$)alkyl refers to a single bond or a branched or unbranched alkylene linker having from 1 to 8 carbons. —(C$_1$-C$_3$)alkyl, —(C$_1$-C$_4$)alkyl, —(C$_1$-C$_8$)alkyl, and —(C$_1$-C$_6$)alkyl, refer to branched or unbranched alkylene linkers having from 1 to 3, 4, 5, or 6, carbons, respectively, while —(C$_2$-C$_6$)alkyl refers to branched or unbranched alkylene linkers having from 2 to 6 carbons.

The term "alkenyl" refers to a branched or unbranched unsaturated hydrocarbon group. By way of illustration, but without limitation, the term "(C$_2$-C$_6$)alkenyl" refers to a branched or unbranched hydrocarbon group having from 2 to 6 carbon atoms and 1 or more carbon-carbon double bonds. Allyl means a propyl-2-en-1-yl moiety (CH$_2$=CH—CH$_2$—).

The term "(C$_3$-C$_7$)cycloalkyl" refers to cyclopropyl, cyclobutyl, cyclopentyl, cyclohexyl and cycloheptyl. Cycloalkylalkyl refers to a cycloalkyl moiety linked through a branched or unbranched alkylene linker, as for example, but without limitation, —CH$_2$—, —CH$_2$CH$_2$—, —CH(CH$_3$)—, —CH$_2$CH$_2$CH$_2$—, —CH$_2$CH(CH$_3$)—, —CH(CH$_3$)CH$_2$—, —CH(CH$_2$CH$_3$)—, and the like. (C$_3$-C$_7$)cycloalkyl(C$_0$-C$_{1, 2 or 3}$)alkyl, refers to cycloalkyls linked through a single bond (i.e. C$_0$-alkyl) or an alkylene linker. Each alkyl, cycloalkyl, and cycloalkylalkyl group may be optionally substituted as provided for herein.

The terms "alkoxy", "cycloalkyloxy", and "sulfonyloxy" refer to an alkyl group, cycloalkyl group, or sulfonyl group, respectively, that is bonded through an oxygen atom.

The terms "alkylthio", "trifluoromethylthio", "cycloalkylthio" ("cyclohexylthio"), "phenylthio", and "furanylthio" refer to an alkyl group, trifluoromethyl group, cycloalkyl (cyclohexyl) group, phenyl group, or furanyl group, respectively, that is bonded through a sulfur atom.

The terms "alkylcarbonyl", "cycloalkylcarbonyl", "alkoxycarbonyl", "phenylcarbonyl", and "phenyloxycarbonyl", refer to an alkyl, cycloalkyl, alkoxy, phenyl, or phenyloxy group bonded through a carbonyl moiety.

The term "alkylsulfonyl" (t-butylsulfonyl, trifluoromethylsulfonyl, etc.), refers to an optionally substituted alkyl group bonded through a sulfonyl moiety (—$SO_2$—).

The term "halo" refers to fluoro, chloro, bromo, or iodo. Preferred halo groups are fluoro, chloro, and bromo. More preferred halo groups are fluoro and chloro.

The term "amino protecting group" as used in this specification refers to a substituent commonly employed to block or protect the amino functionality while reacting other functional groups on the compound. Examples of such amino protecting groups include the formyl group, the trityl group, the acetyl group, the trichloroacetyl group, the trifluoroacetyl group, the chloroacetyl, bromoacetyl, and iodoacetyl groups, carbamoyl-type blocking groups such as benzyloxycarbonyl, 9-fluorenylmethoxycarbonyl ("FMOC"), t-butoxycarbonyl (t-BOC), and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", $3^{rd}$ edition, John Wiley and Sons, New York, N.Y., 1999, chapter 7, hereafter referred to as "*Greene*".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula V). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of activating $5\text{-}HT_{2C}$ receptors and/or elicit a given pharmacological effect.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)— and (S)— and the cis and trans designation of relative stereochemistry are used to refer to specific isomers and relative stereochemistry. Known optical rotations are designated by (+) and (−) for dextrorotatary and levorotatary, respectively. Where a chiral compound is resolved into its isomers, but absolute configurations or optical rotations are not determined, the isomers are arbitrarily designated as isomer 1, isomer 2, etc. While all enantiomers, diastereomers, and mixtures thereof, are contemplated within the present invention, preferred embodiments are single enantiomers and single diastereomers.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see for example, Berge, S. M, Bighley, L. D., and Monklouse, D. C., *J. Pharm. Sci.*, 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

Typical inorganic acids used to form such salts include hydrochloric, hydrobromic, hydroiodic, nitric, sulfuric, phosphoric, hypophosphoric, metaphosphoric, pyrophosphoric acid, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caproate, caprylate, cinnamate, citrate, formate, fumarate, glycolate, heptanoate, hippurate, lactate, malate, maleate, hydroxymaleate, malonate, mandelate, nicotinate, isonicotinate, oxalate, phthalate, terephthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate (mesylate), naphthalene-1-sulfonate, naphthalene-2-sulfonate, naphthalene-1,5-sulfonate, p-toluenesulfonate, xylenesulfonate, tartrate, and the like.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio. Terms such as "$(acid)_x$" are understood to mean that the molar ratio of the salt formed is not known and can not be presumed, as for example, but without limitation, $(HCl)_x$ and $(\text{methanesulfonic acid})_x$.

Abbreviations used herein are defined as follows:

"2B-3 ethanol" means ethanol denatured with toluene.

"Anal. Calc'd" or "Anal. Calcd" means calculated elemental analysis.

"Boc" or "t-Boc" means tert-butoxycarbonyl.

"bp" means boiling point.

"Brine" means a saturated aqueous sodium chloride solution.

"CV" means calorific value of oxygen.

"DCM" means dichloromethane (i.e. methylene chloride, $CH_2Cl_2$).

"DME" means 1,2-dimethoxyethane.

"DMF" means N,N-dimethylformamide.

"DMSO" means dimethylsulfoxide.

"DOI" means (+)-1-(2,5-dimethoxy-4-[$^{125}$I]-iodophenyl)-2-aminopropane.

"DPPA" means diphenyl phosphoryl azide.

"DPPP" means 1,3-bis(diphenylphosphino)propane.

"EDTA" means ethylenediaminetetraacetic acid.

"EE" means energy expenditure.

"EtOAc" means ethyl acetate.

"GC-MS" means gas chromatography—mass spectrometry.

"GDP" means guanosine diphosphate.

"GTP" means guanosine triphosphate.

"GTPγ[$^{35}$S]" means guanosine triphosphate having the terminal phosphate substituted with $^{35}$S in place of an oxygen.

"HPLC" means high-pressure liquid chromatography.

"IR" means InfraRed.

"ISPA" means immunoadsorption scintillation proximity assay.

"m-CPBA" means meta-chloroperoxybenzoic acid.

"mp" means melting point.

"Ms" in a chemical structure means the methanesulfonyl moiety (—SO$_2$CH$_3$).

"MS (APCI+)" means mass spectroscopy using atmospheric pressure chemical ionization.

"MS (ES+)" means mass spectroscopy using electrospray ionization.

"MTBE" means methyl t-butyl ether.

"NMR" means nuclear magnetic resonance.

"Pd/C" means palladium on activated carbon.

"psi" means pounds per square inch.

"RQ" means respiratory quotient.

"SCX chromatography" means chromatography on an SCX column or cartridge.

"SCX column" or "SCX cartridge", as used herein, refers to a Varian Bond Elute® silica based strong cation exchange resin column or disposable cartridge or equivalent.

"Sudan III" means 1-[(4-phenylazo)phenylazo]-2-naphthalenol.

"Tf" in a chemical structure means the trifluoromethanesulfonyl moiety (—SO$_2$CF$_3$).

"TFA" means trifluoroacetic acid.

"THF" means tetrahydrofuran.

"TLC" means thin layer chromatography.

While all of the compounds of the present invention are useful as 5-HT$_{2C}$ agonists, certain classes are preferred, as for example, compounds having any of the following enumerated selections of substituents: Compounds wherein 1) $R^7$ is halo;
2) $R^7$ is chloro;
3) $R^7$ is fluoro;
4) $R^7$ is (C$_1$-C$_6$)alkyl optionally substituted with 1 to 6 fluoro substituents;
5) $R^7$ is (C$_1$-C$_3$)alkyl optionally substituted with 1 to 6 fluoro substituents;
6) $R^7$ is —CF$_3$;
7) $R^7$ is (C$_3$-C$_6$)alkenyl optionally substituted with 1 to 6 fluoro substituents;
8) $R^7$ is (C$_3$-C$_6$)alkenyl;
9) $R^7$ is cyano;
10) $R^{1-5}$ are each hydrogen;
11) $R^5$ is methyl or ethyl;
12) $R^5$ is methyl;
13) $R^3$ is methyl;
14) $R^3$ is hydrogen;
15) $R^9$ is hydrogen;
16) $R^9$ is (C$_1$-C$_3$)alkoxy;
17) $R^9$ is methoxy;
18) $R^9$ is halo;
19) $R^9$ is chloro;
20) $R^9$ is cyano;
21) $R^9$ is —CF$_3$;
22) $R^6$ is —C≡C—R$^{10}$;
23) the proximal alkylene linker in $R^{10}$ is (C$_1$-C$_4$)alkyl;
24) the proximal alkylene linker in $R^1$ is (C$_1$-C$_3$)alkyl;
25) the proximal alkylene linker in $R^{10}$ is (C$_2$-C$_3$)alkyl;
26) $R^{10}$ is Het$^1$-(C$_1$-C$_5$)alkyl;
27) $R^{10}$ is Het$^1$-(C$_1$-C$_5$)alkyl and Het$^1$ is 2-oxo-imidazolidin-1-yl optionally further substituted;
28) $R^{10}$ is Het$^1$-(C$_1$-C$_5$)alkyl and Het$^1$ is 2-oxo-imidazolidin-1-yl;
29) $R^{10}$ is Het$^1$-(C$_1$-C$_5$)alkyl and Het$^1$ is 2,5-dioxo-imidazolidin-1-yl optionally further substituted;
30) $R^{10}$ is Het$^1$-(C$_1$-C$_5$)alkyl and Het$^1$ is 2,5-dioxo-imidazolidin-1-yl;
31) $R^{10}$ is $R^{12}$—C(O)N(R$^{13}$)—(C$_1$-C$_5$)alkyl;
32) $R^{10}$ is $R^{12}$—C(O)N(R$^{13}$)—(C$_1$-C$_5$)alkyl and $R^{13}$ is hydrogen;
33) $R^{10}$ is $R^{12}$—C(O)N(R$^{13}$)—(C$_1$-C$_5$)alkyl, $R^{13}$ is hydrogen, and $R^{12}$ is (C$_1$-C$_6$)alkyl optionally substituted with 1 to 6 fluoro substituents, or (C$_3$-C$_7$)cycloalkyl-(C$_0$-C$_3$)alkyl;
34) $R^{10}$ is $R^{12}$—C(O)N(R$^{13}$)—(C$_1$-C$_5$)alkyl, $R^{13}$ is hydrogen, and $R^{12}$ is (C$_1$-C$_6$)alkyl optionally substituted with 1 to 6 fluoro substituents, or (C$_3$-C$_7$)cycloalkyl;
35) $R^{10}$ is $R^{12}$—C(O)N(R$^{13}$)—(C$_1$-C$_5$)alkyl, $R^{13}$ is hydrogen, and $R^{12}$ is (C$_1$-C$_6$)alkoxy-(C$_0$-C$_3$)alkyl optionally substituted with 1 to 6 fluoro substituents;
36) $R^{10}$ is $R^{12}$—C(O)N(R$^{13}$)—(C$_1$-C$_5$)alkyl, $R^{13}$ is hydrogen, and $R^{12}$ is (C$_1$-C$_6$)alkoxy- optionally substituted with 1 to 6 fluoro substituents (i.e. (C$_0$-C$_3$)alkyl is C$_0$ alkyl, which is a single bond);
37) $R^{10}$ is $R^{14}R^{15}$NC(O)—NR$^{13}$—(C$_1$-C$_5$)alkyl optionally substituted on the alkyl moiety with 1 to 6 fluorine substituents;
38) $R^{10}$ is $R^{14}R^{15}$NC(O)—NR$^{13}$—(C$_1$-C$_5$)alkyl and $R^{13}$ is hydrogen;
39) $R^6$ is —CH=C—R$^{11}$R$^{11'}$;
40) $R^{11'}$ is hydrogen;
41) $R^{11'}$ is methyl;
42) $R^{11}$ is Ar$^1$—(C$_0$-C$_3$)alkyl optionally substituted on the alkyl moiety with 1 to 6 fluoro substituents;
43) $R^{11}$ is Ar$^1$—(C$_0$-C$_3$)alkyl and Ar$^1$ is optionally substituted pyrrolyl;
44) $R^{11}$ is Ar$^1$—(C$_1$-C$_3$)alkyl and Ar$^1$ is optionally substituted pyridyl;
45) $R^{11}$ is Ar$^1$—(C$_0$-C$_3$)alkyl and Ar$^1$ is optionally substituted thiophenyl;
46) $R^{11}$ is Het$^1$-(C$_1$-C$_5$)alkyl
47) $R^{11}$ is Het$^1$-(C$_1$-C$_5$)alkyl and Het$^1$ is optionally substituted dihydroimidizolyl;
48) $R^{11}$ is Het$^1$-(C$_1$-C$_5$)alkyl and Het$^1$ is optionally substituted 2-oxo-dihydroimidizol-1-yl;
49) $R^{11}$ is $R^{12}$—C(O)N(R$^{13}$)—(C$_1$-C$_5$)alkyl;
50) $R^{11}$ is $R^{12}$—C(O)N(R$^{13}$)—(C$_1$-C$_5$)alkyl and $R^{13}$ is hydrogen;
51) $R^{11}$ is $R^{12}$—C(O)N(R$^{13}$)—(C$_1$-C$_5$)alkyl and $R^{13}$ is hydrogen and $R^{12}$ is optionally substituted (C$_3$-C$_7$)cycloalkyl-(C$_0$-C$_3$)alkyl;
52) $R^{11}$ is Ph$^2$-(C$_0$-C$_3$)alkyl optionally substituted on the alkyl moiety with 1 to 6 fluoro substituents;
53) $R^{11}$ is Ph$^2$-(C$_0$-C$_3$)alkyl wherein Ph$^2$- is phenyl substituted with 1 to 3 substituents selected from halo and (C$_1$-C$_6$)alkyl;
54) $R^{11}$ is Ph$^2$-(C$_0$-C$_3$)alkyl wherein Ph$^2$- is phenyl substituted with 1 to 3 substituents selected from halo and (C$_1$-C$_3$)alkyl;
55) $R^{11}$ is Ph$^2$-(C$_0$-C$_3$)alkyl wherein Ph$^2$- is phenyl substituted with 1 to 3 halo substituents;
56) $R^6$ is —(C$_0$-C$_8$)alkyl —Ar$^2$, optionally substituted on the alkyl moiety with 1 to 6 fluoro substituents;
57) $R^6$ is —(C$_0$-C$_3$)alkyl —Ar$^2$;
58) $R^6$ is -ethyl-Ar$^2$ (i.e. —(C$_0$-C$_3$)alkyl is selected to be C$_2$-alkyl); and 59) $R^6$ is —$Ar^2$ (i.e. —($C_0$-$C_3$)alkyl is selected to be $C_0$-alkyl, which is a single bond).

It will be understood that the above classes may be combined to form additional preferred classes. Exemplary combinations include, but are not limited to:
60) Any one of preferred embodiments 22) through 59) (the preferred selections for $R^6$), combined with any one of preferred embodiments 1) through 9) (the preferred selections for $R^7$);
61) Any one of preferred embodiments 22) through 59) (the preferred selections for $R^6$), wherein $R^7$ is halogen;
62) Any one of preferred embodiments 22) through 59) (the preferred selections for $R^6$), wherein $R^7$ is chloro;
63) A preferred combination according to 60), 61), or 62), wherein $R^{1-5}$, and $R^8$ are each hydrogen;
64) A preferred combination according to 60), 61), or 62), wherein $R^{1-5}$, $R^1$ and $R^9$, are each hydrogen.
65) Any one of preferred embodiments 10) through 21), wherein $R^7$ is other than hydrogen;
66) Any one of preferred embodiments 10) through 14), wherein $R^9$ is hydrogen;
67) Any one of preferred embodiments 10) through 14), wherein $R^7$ is other than hydrogen and $R^9$ is hydrogen;
68) Any one of preferred embodiments 10) through 14), wherein $R^7$ is chloro and $R^9$ is hydrogen;
69) Any one of preferred embodiments 22) through 59) (the preferred embodiments for $R^6$), wherein $R^{1-5}$ and $R^{8-9}$ are each hydrogen;
70) Any one of preferred embodiments 22) through 38) (the preferred embodiments for selections wherein $R^6$ is —C≡C—$R^{10}$), wherein $R^{1-5}$ and $R^{8-9}$ are each hydrogen;
71) Any one of preferred embodiments 39) through 55) (the preferred embodiments for selections wherein $R^6$ is —CH=C $R^{11}R^{11'}$), wherein $R^{1-5}$ and $R^{8-9}$ are each hydrogen;
72) Any one of preferred embodiments 56) through 59) (the preferred embodiments for selections wherein $R^6$—($C_0$-$C_8$)alkyl-$Ar^2$), wherein $R^{1-5}$ and $R^{8-9}$ are each hydrogen;
73) Any one of preferred embodiments 42) through 55), wherein $R^{11'}$ is hydrogen;

Particularly preferred compounds of formula (I) are those wherein $R^6$ is —C≡C—$R^{10}$, —CH=C$R^{11}R^{11'}$, —($C_0$-$C_8$) alkyl-$Ar^2$ optionally substituted on the alkyl moiety with 1 to 6 fluoro substituents, or —($C_0$-$C_8$)alkyl-$Het^1$ optionally substituted on the alkyl moiety with 1 to 6 fluoro substituents. More particularly, are those compounds wherein $R^6$ is —C≡C—$R^{10}$, —CH=C$R^{11}R^{11'}$, —($C_0$-$C_8$)alkyl-$Ar^2$ optionally substituted on the alkyl moiety with 1 to 6 fluoro substituents.

Particularly preferred compounds of formula (I) are those wherein $R^7$ is halogen, and in particular wherein $R^7$ is chloro.

Also preferred are those compounds of formula (I) wherein $R^9$ is hydrogen.

Other preferred compounds of formula (I) are those wherein $R^9$ is ($C_1$-$C_3$)alkoxy, preferably methoxy, or halo, preferably chloro.

Particularly preferred compounds of formula (I) are those wherein $R^7$ is other than hydrogen and $R^9$ is hydrogen, and most especially wherein $R^7$ is chloro and $R^9$ is hydrogen.

Also preferred are those compounds of formula (I) wherein $R^3$ is hydrogen or methyl, and especially wherein $R^3$ is hydrogen.

Also preferred are those compounds of formula (I) wherein $R^{1-5}$ and $R^{8-9}$ are each hydrogen.

One favored group of compounds of the present invention is that represented by formula (Ia), and pharmaceutically acceptable salts and solvates thereof:

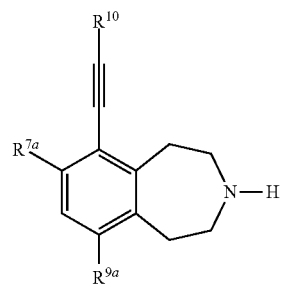

wherein
$R^{7a}$ is halogen, and especially chloro;
$R^{9a}$ is hydrogen, halogen, cyano, hydroxy, or —$CF_3$; and
$R^{10}$ is as defined in relation to formula (I).

Preferred embodiments according to formula Ia are those enumerated above pertaining to compounds wherein $R^6$ may be —C≡C—$R^{10}$.

Another favored group of compounds of the present invention is that represented by formula (Ib), and pharmaceutically acceptable salts and solvates thereof:

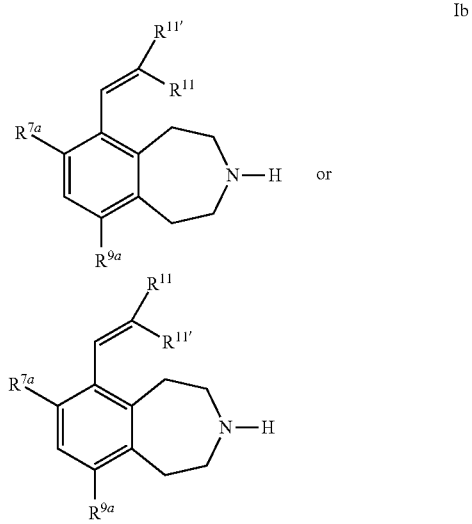

wherein
$R^{7a}$ is halogen, and especially chloro;
$R^{9a}$ is hydrogen, halogen, cyano, hydroxy, or —$CF_3$; and
$R^{11}$ and $R^{11'}$ are as defined in relation to formula (I).

Preferred embodiments according to formula Ib are those wherein $R^{11}$ is in the cis conformation relative to the tetrahydrobenzazepine core structure. Other preferred embodiments are those enumerated above pertaining to compounds wherein $R^6$ may be —CH=C—$R^{11}R^{11'}$.

Yet another favored group of compounds of the present invention is that represented by formula (Ic), and pharmaceutically acceptable salts and solvates thereof:

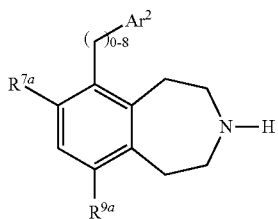

wherein
  $R^{7a}$ is halogen, and especially chloro;
  $R^{9a}$ is hydrogen, halogen or $(C_1-C_3)$alkoxy, particularly hydrogen, chloro or methoxy, and especially hydrogen; and
  $Ar^2$ is as defined in relation to formula (I).

Preferred embodiments according to formula Ic are those enumerated above pertaining to compounds wherein $R^6$ may be alkyl-$Ar^2$.

Yet another favored group of compounds of the present invention is that represented by formula (Id), and pharmaceutically acceptable salts and solvates thereof:

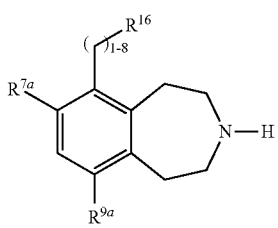

wherein
  $R^{7a}$ is halogen, and especially chloro;
  $R^{9a}$ is hydrogen, halogen, cyano, hydroxy, or —$CF_3$;
  $R^{16}$ is -$Het^1$ or —$N(R^{13})C(O)$—$R^{12}$; and
  $Het^1$, $R^{13}$, and $R^{12}$ are as defined in claim 1 in relation to formula (I);

Specific preferred compounds of the present invention are those described in the Examples herein, including the free bases and the pharmaceutically acceptable salts and solvates thereof.

It will be appreciated that the preferred definitions of the various substituents recited herein may be taken alone or in combination and, unless otherwise stated, apply to the generic formula (I) for compounds of the present invention, as well as to the preferred classes of compounds represented by formulae (Ia), (Ib), and (Ic).

The compounds of the invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may by isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties as is well appreciated by those of ordinary skill in the art. The reduction of alkynes to either alkenes or alkanes, at the choice of the operator, and the reduction of alkenes to alkanes, are well known within the ordinary skill of the art. Examples of appropriate catalysts, solvents and reaction conditions are described by P. Rylander, "Hydrogenation Methods", Academic Press, New York, N.Y., 1985, chapters 2 and 3, hereafter referred to as "*Rylander*". All substituents, unless otherwise indicated, are as previously defined, and all reagents are well known and appreciated in the art.

Compounds of formula I where $R^6$ is an alkyne-linked substituent may be prepared as illustrated in Scheme I, where Pg is a suitable protecting group for a secondary amine such as, but not limited to, 2,2,2-trifluoroacetyl or tert-butoxycarbonyl, and variables $R^1$, $R^2$, $R^4$, $R^5$, $R^7$, $R^8$, $R^9$ and $R^{10}$ are as previously defined.

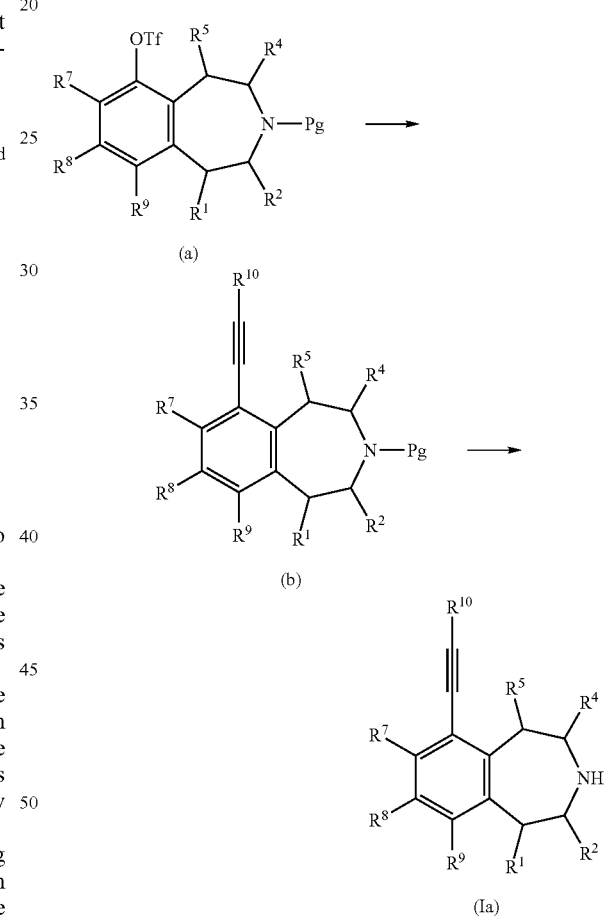

Mix the 6-triflate of the 2,3,4,5-tetrahydro-1H-benzo[d] azepines (a) with an appropriately substituted acetylene, a suitable palladium/copper catalyst mixture in a solvent, typically DMF, using triethylamine as base, and heat to afford the desired compound (b). Deprotection reaction and the standard extractive and chromatographic techniques afford the desired compound (Ia). The acetylenes are either commercially available or may be prepared by methods well known to the skilled artisan.

Alternately compound (b) could be prepared from the alcohol (d) as shown in Scheme II below.

Scheme II

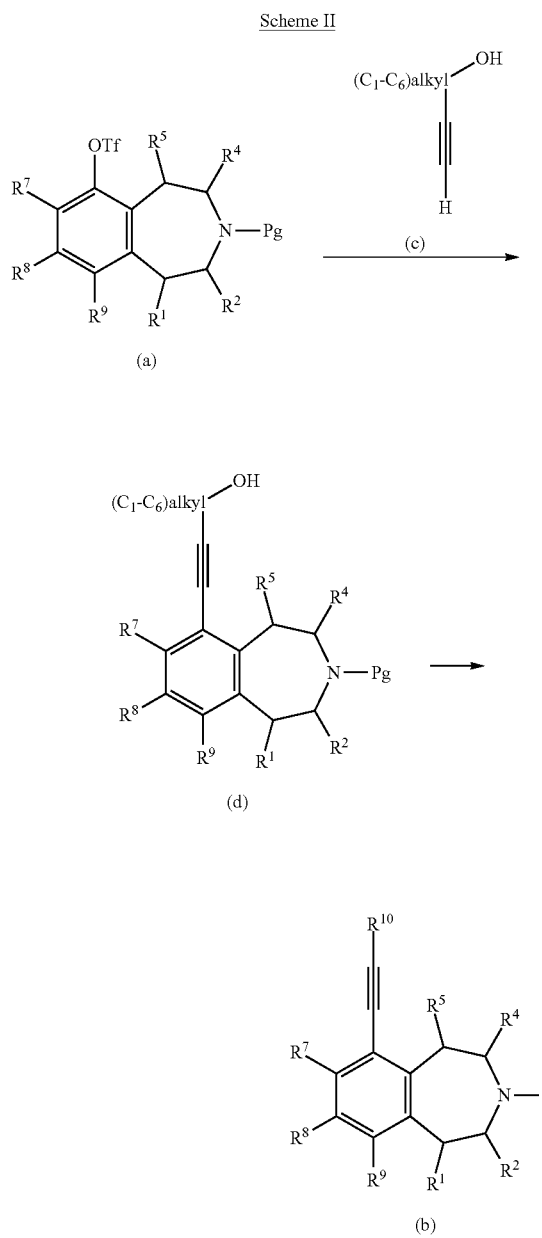

Mix the 6-triflate of the desired 2,3,4,5-tetrahydro-1H-benzo[d]azepines (a) with an appropriate acetylenic alcohol (c), a suitable palladium/copper catalyst mixture in a solvent, typically DMF, using triethylamine as base, and heat to afford the desired compound (d). Activate the alcohol by conversion to a sulfonate ester or a halide, using methods well known to the skilled artisan, then couple with a suitable nucleophile, such as an amine, alcohol, thiol or heterocycle such as $Het^1$ (as previously defined), in the presence of a suitable base in an appropriate solvent, typically acetonitrile, DMF, THF, acetone, or the like, to give compound (b). Alternately, compound (b) can be obtained by Mitsunobu reaction of compound (d) with an appropriate heterocycle such as $Het^1$ (as previously defined), a phosphine reagent such as triphenylphosphine, and diethyl azodicarboxylate (DEAD) or 1,1'-(azodicarbonyl)-dipiperidine in an anhydrous solvent, for example THF. The acetylenic alcohols (c) are either commercially available or may be prepared by methods well known to the skilled artisan.

Alternately compound (b) could be prepared from the amines (f) as shown in Scheme III.

Scheme III

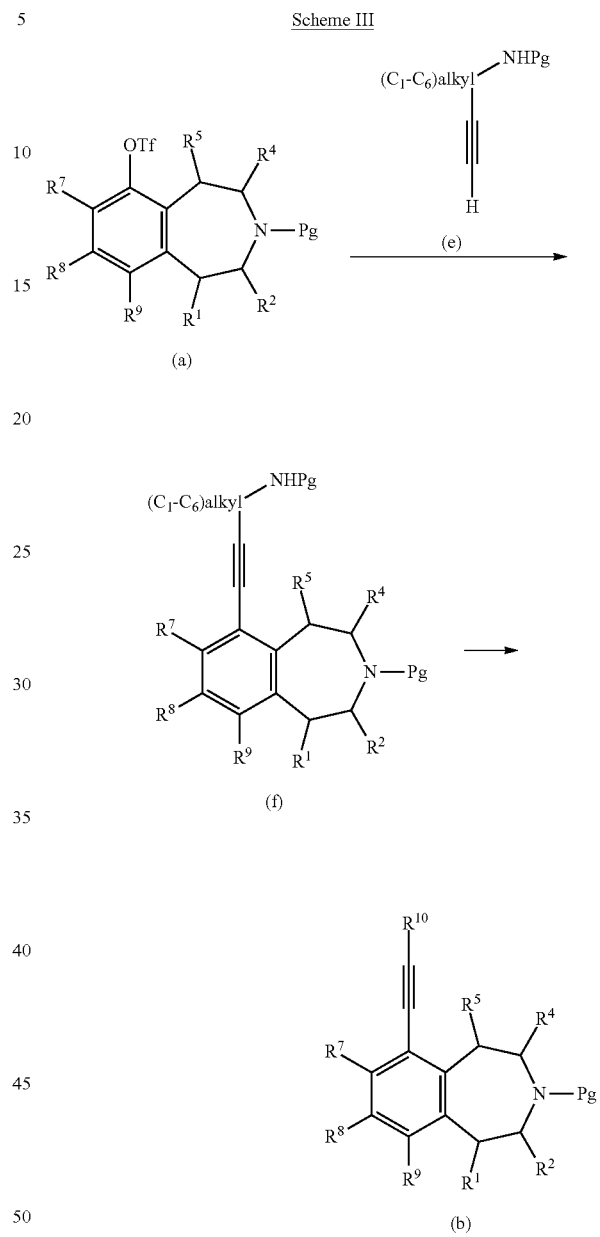

Mix the 6-triflate of the 2,3,4,5-tetrahydro-1H-benzo[d]azepines (a) with an appropriately protected acetylenic amine (e), a suitable palladium/copper catalyst mixture in a solvent, typically DMF, using triethylamine as base, and heat to afford the desired compound (f). Deprotection of the amine and coupling with a carboxylic acid, acyl halide, acid anhydride, alkyl chloroformate or alkyl isocyanate, by methods well known to the skilled artisan, affords the desired compound (b). The protected acetylenic amines (e) are either commercially available or may be prepared by methods well known to the skilled artisan.

Compounds of Formula I where $R^6$ is an alkene- or alkane-linked substituent may be prepared from the alkynes (b) as illustrated in Scheme IV.

Scheme IV

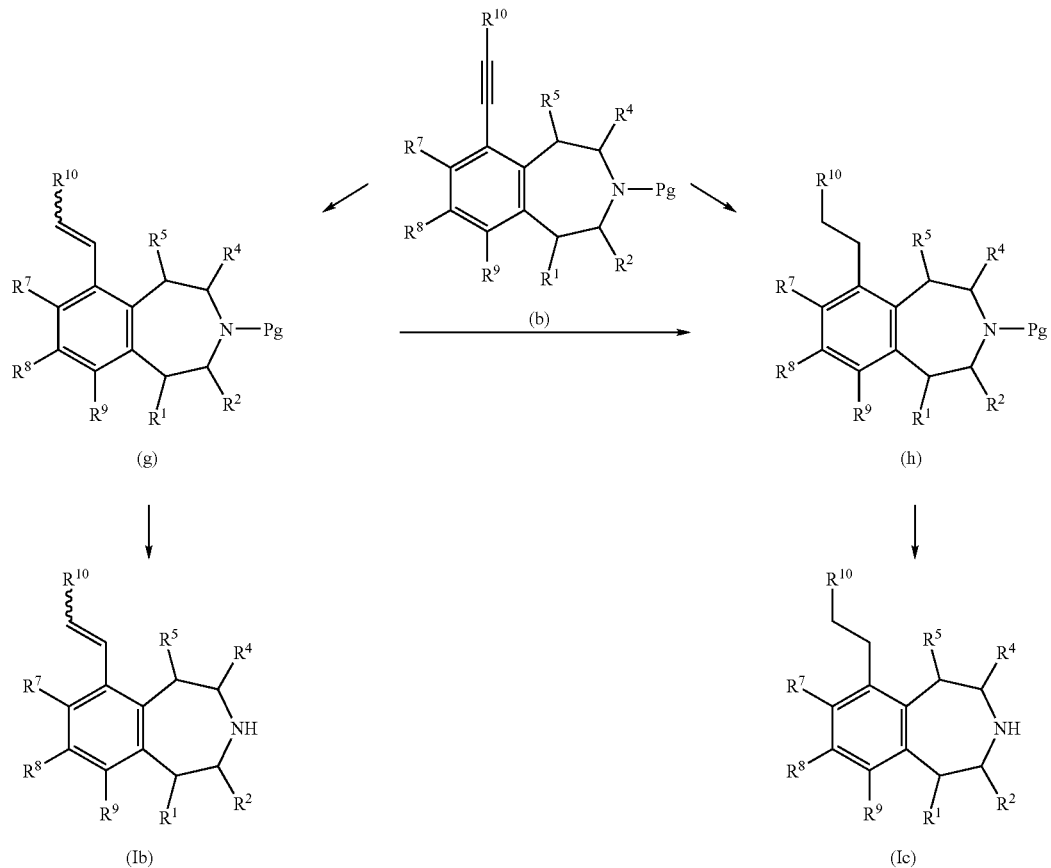

Partial reduction of compound (b) by methods well known to the skilled artisan affords alkene (g). (See Rylander, chapter 3). Deprotection reaction and the standard extractive and chromatographic techniques afford the desired compound (Ib). Complete reduction of compound (b) by methods well known to the skilled artisan to affords alkane (h). (See Rylander, chapters 2 and 3). Deprotection reaction and the standard extractive and chromatographic techniques afford the desired compound (Ic). Alternately, alkane (h) may be obtained from alkene (g) by reduction, using methods well known to the skilled artisan. (See Rylander, chapter 2).

Compounds of Formula I where $R^6$ is an alkene-linked substituent may alternately be prepared from the triflate (a) as illustrated in Scheme V. ($R^{11}$ and $R^{11'}$ are as previously defined.)

Scheme V

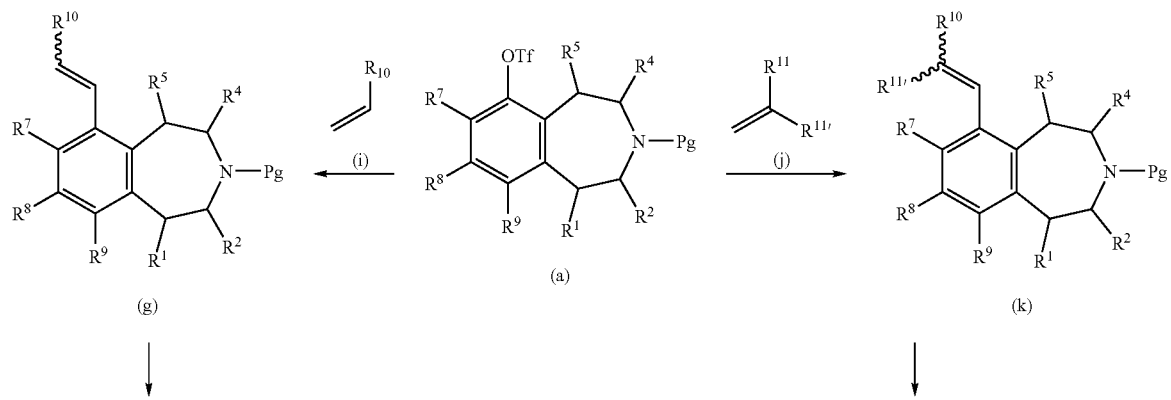

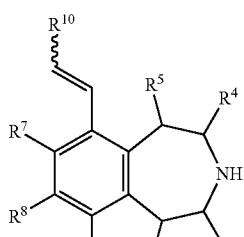

(Ib)

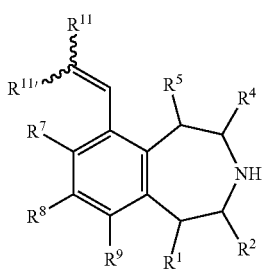

(Id)

The 6-triflate protected 2,3,4,5-tetrahydro-1H-benzo[d]azepines (a) can be converted to the compounds (g) or (k), under Heck conditions, by treatment with an appropriate alkene (i) or (j) in the presence of an effective palladium catalyst, such as tetrakistriphenylphosphinepalladium(0) or palladium (II) acetate and triphenylphosphine, and a base in a suitable solvent, typically toluene, DMF or 1,4-dioxane under an inert atmosphere. Deprotection reaction and the standard extractive and chromatographic techniques afford the desired compounds (Ib) and (Id). The alkenes (i) and (O) are either commercially available or may be prepared by methods well known to the skilled artisan.

Compounds of Formula I where $R^6$ is an alkane-linked substituent may be prepared from the alkenes (k) as illustrated in Scheme VI.

Reduction of alkenes (k) by methods well known to the skilled artisan affords alkane (l). (See Rylander, chapter 2). Deprotection reaction and the standard extractive and chromatographic techniques afford the desired compound (Ie).

Scheme VI

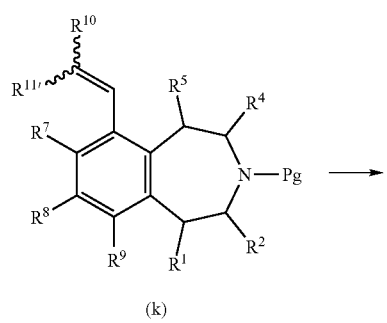

(k)

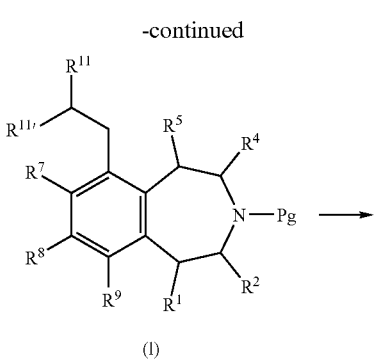

(l)

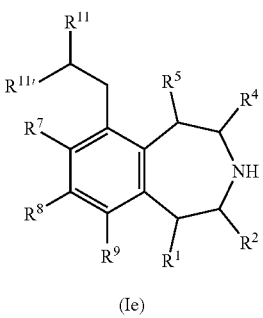

(Ie)

Alternately, compounds of Formula I where $R^6$ is an alkane-linked substituent may be prepared from the triflate (a) as illustrated in Scheme VII.

Scheme VII

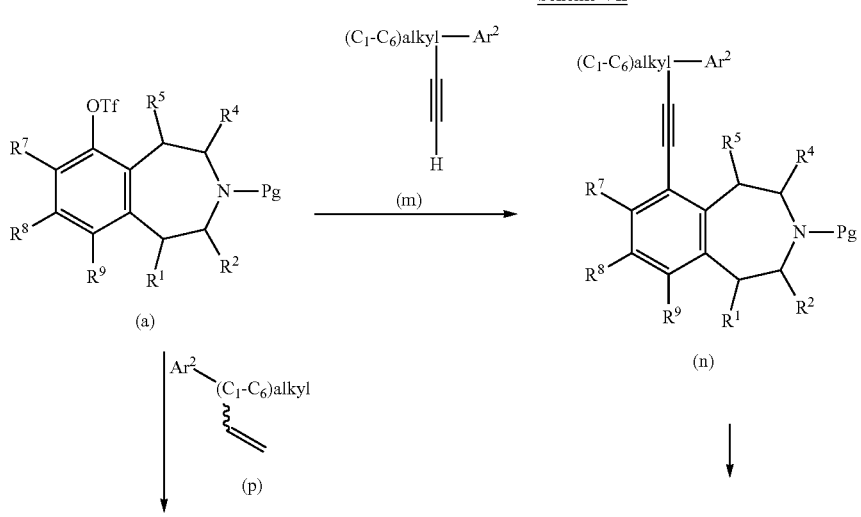

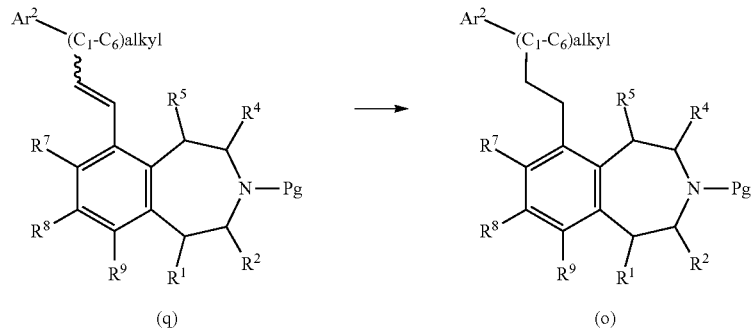

(q)  (o)

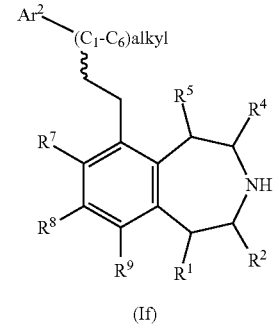

(If)

Mix the 6-triflate of the 2,3,4,5-tetrahydro-1H-benzo[d]azepines (a) with an appropriately substituted acetylene (m), a suitable palladium/copper catalyst mixture in a solvent, typically DMF, using triethylamine as base, and heat to afford the desired compound (n). Reduction of alkynes (n) by methods well known to the skilled artisan, as referenced above, affords alkane (o). Deprotection reaction and the standard extractive and chromatographic techniques afford the desired compound (If). The acetylenes (m) are either commercially available or may be prepared by methods well known to the skilled artisan. Alternately, the 6-triflate protected 2,3,4,5-tetrahydro-1H-benzo[d]azepines (a) can be converted to the alkene (q), under Heck conditions, by treatment with an appropriate alkene (p) in the presence of an effective palladium catalyst, and a base in a suitable solvent, typically toluene, DMF or 1,4-dioxane under an inert atmosphere. Reduction of alkenes (q), by methods well known to the skilled artisan, and referenced above, affords alkane (o). Deprotection reaction and the standard extractive and chromatographic techniques afford the desired compound (If). The alkenes (p) are either commercially available or may be prepared by methods well known to the skilled artisan.

The appropriate 6-triflate of 2,3,4,5-tetrahydro-1H-benzo[d]azepines (a) may be prepared as described in Scheme VIII. Compound (a) may be prepared from 1-naphthol. 1-Naphthol can be converted to 5-hydroxy-1,4-dihydronaphthalene (r) by Birch reduction using ammonia and lithium metal at low temperature. Methylation of the 6-hydroxy group affords the compound (s). Ozonolysis of compound (s) and subsequent reduction with sodium borohydride provide the diol (t). After converting the two hydroxyl groups into two good leaving groups, for example methanesulfonates, cyclize the compound (u) to the 6-methoxy-2,3,4,5-tetrahydro-1H-benzo[d]azepines (v) with aqueous ammonia under pressure. Protect the ring nitrogen with a variety of alkyl halides, acid chlorides or anhydrides such as trifluoroacetic anhydride to give compound (w). Subsequently convert the methyl ether (w) to the phenol (x) with BBr$_3$ in dichloromethane or other methods well known in the literature [see for example, Greene and Wuts, Protective Groups in Organic Synthesis, 3$^{rd}$ Ed., John Wiley and sons, Chapter In, New York (1999)].

Functionalization of the aromatic ring to introduce substituents $R^{1-5}$, $R^7$, $R^8$ and $R^9$ are well known in the art and vary depending on the substitution desired. Subsequent trifluoromethanesulfonylation of the 6-hydroxy (y) affords the desired 6-trifluoromethyl-sulfonyloxy-2,3,4,5-tetrahydro-1H-benzo[d]azepines (a).

Scheme VIII

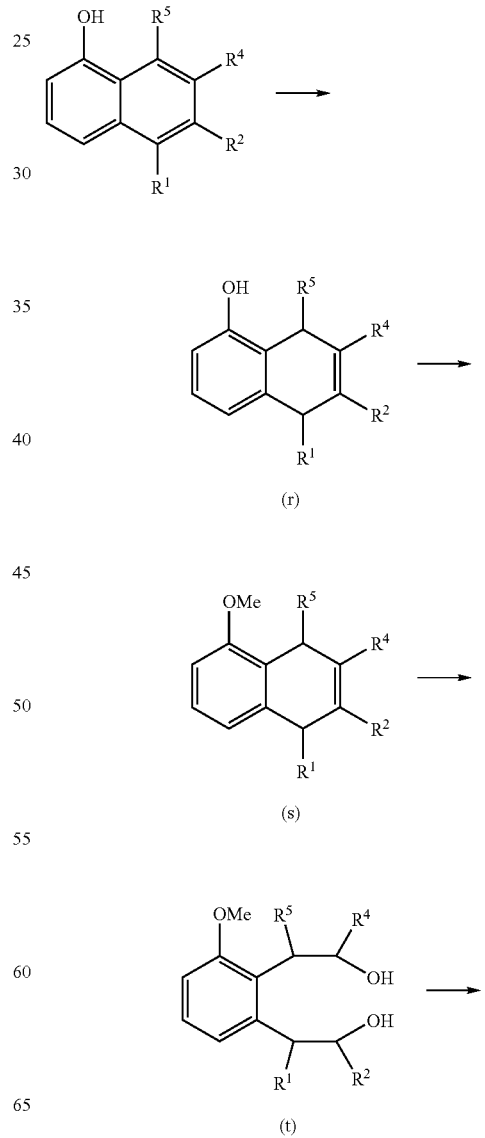

(r)

(s)

(t)

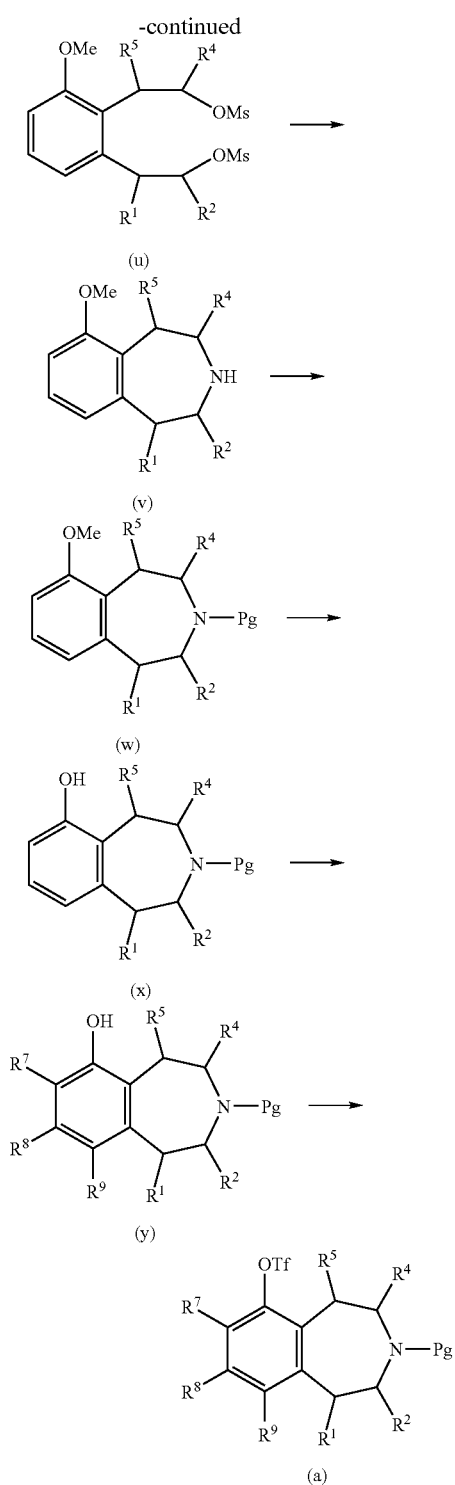

The following Preparations and Examples are illustrative of methods useful for the synthesis of the compounds of the present invention. Exemplified compounds are also particularly preferred compounds of the present invention.

General Procedure 1-1

Dissolve the appropriately substituted 3-(2,2,2-trifluoroacetyl)-2,3,4,5-tetrahydro-1H-benzo[d]azepine in ammonia/methanol solution (1-7 M). Stir for 1-16 h at room temperature unless otherwise specified. Remove the volatiles in vacuo. Purify, if necessary, by chromatography on silica gel eluting with 1-20% 2M ammonia/methanol in dichloromethane, or by SCX chromatography eluting with methanol followed by 1.0-7.0 M ammonia in methanol.

General Procedure 1-2

Dissolve the appropriately substituted 3-(2,2,2-trifluoroacetyl)-2,3,4,5-tetrahydro-1H-benzo[d]azepine (1.0 equiv.) in methanol. Add a 0.5 M aqueous solution of potassium carbonate (4.0 equiv.) and stir at room temperature for 6 h. Concentrate in vacuo and partition the residue between water and dichloromethane. Extract the aqueous phase twice with dichloromethane. Dry the combined organic extracts over $Na_2SO_4$, filter and concentrate in vacuo. Purify, if necessary, by chromatography on silica gel eluting with 1-20% 2M ammonia/methanol in dichloromethane, or by SCX chromatography eluting with methanol followed by 1.0-7.0 M ammonia in methanol.

General Procedure 1-3

Dissolve the appropriately substituted 3-tert-butoxycarbonyl-2,3,4,5-tetrahydro-1H-benzo[d]azepine in 4M hydrogen chloride in dioxane or 1M hydrogen chloride in diethyl ether and stir the mixture for 2-16 h at room temperature unless otherwise specified. Remove the solvent in vacuo. If a solid is obtained, wash the solid with ether and filter under vacuum to afford the desired hydrochloride salt. If an oil is obtained, dissolve the oil in the minimal volume of dichloromethane, methanol or EtOAc and add ether to precipitate out the solid. Remove the solvent in vacuo, wash the solid with ether and filter. Dry the solid in vacuo or under a stream of nitrogen.

General Procedure 1-4

Dissolve the appropriately substituted 3-tert-butoxycarbonyl-2,3,4,5-tetrahydro-1H-benzo[d]azepine in a mixture of trifluoroacetic acid/dichloromethane (from 1:0 to 1:10 ratio) and stir the reaction for 1-16 h at room temperature. Concentrate in vacuo and either subject the residue to SCX chromatography or partition the residue between saturated aqueous $NaHCO_3$ and dichloromethane or EtOAc. Dry the organic layer over $Na_2SO_4$ and concentrate in vacuo. Purify, if necessary, by either chromatography on silica gel (eluting with 1-20% 2M ammonia/methanol in dichloromethane) or reverse phase HPLC.

General Procedure 2-1

Dissolve the purified free base (1 equiv.) in acetone, ether or methanol and add a solution of succinic acid (1 equiv.) in a minimal volume of acetone or methanol. Stir for 1 h at room temperature. Concentrate to an oil, add a minimal volume of dichloromethane and ethyl ether to precipitate out the salt. Alternatively, to precipitate out the salt, allow the reaction mixture to stand 1-16 h at room temperature, 4° C. or −10° C. and add ether or hexane. Filter and wash the solid with ether or hexane to obtain the succinate salt. Alternatively, evaporate the solvent in vacuo, wash the solid with ether and filter or decant the solvent to obtain the succinate salt as a solid. Dry the solid in vacuo or under a stream of nitrogen.

General Procedure 2-2

Dissolve the purified free base (1 equiv.) in a minimal volume of acetone, dioxane, methanol or dichloromethane and add an excess of 4M hydrogen chloride in dioxane or a 1M solution of hydrogen chloride in diethyl ether. Stir for 1 h and evaporate the solvent to obtain the salt as a solid. Alternatively, allow the reaction mixture to stand 1 to 16 h at room temperature and add ether or hexane to precipitate out the salt. Filter and wash the solid with ether or hexane to obtain the salt as a solid. Alternatively, evaporate the solvent in vacuo, wash the solid with ether, filter or decant the solvent to obtain the hydrochloride salt as a solid. Dry the solid in vacuo or under a stream of nitrogen.

General Procedure 2-3

Dissolve the purified free base (1 equiv.) in a minimal volume of dichloromethane, ether, methanol or chloroform and add a solution of (L)-tartaric acid (1 equiv.) in a minimal volume of methanol. Allow the mixture to stand 10 min to 16 h at room temperature and evaporate the solvent to obtain the salt as a solid. Alternatively add ether or hexane to precipitate out the solid. Dry the solid in vacuo or under a stream of nitrogen. Alternatively evaporate the solvent and dissolve the resulting oil with acetonitrile/water (2:1) and water (so that the final solution has an excess of water) and freeze dry the solution.

General Procedure 3

Dissolve 7-chloro-3-(2,2,2-trifluoroacetyl)-6-trifluoromethanesulfonyloxy-2,3,4,5-tetrahydro-1H-benzo[d]azepine (1 equiv.), dichlorobis(triphenylphosphine)-palladium(II) (0.1 equiv.), tetrabutyl ammonium iodide (3 equiv.), and copper(I) iodide (0.3 equiv.) in triethylamine/DMF (1:5). Stir the mixture for 5 min at room temperature, add the appropriately substituted acetylene (2 equiv.) and heat at 70° C. for 4-14 h in a sealed tube. Cool the reaction mixture to room temperature, dilute with hexane/EtOAc (1:1) and wash with water. Dry the organic phase over MgSO$_4$, filter and concentrate in vacuo. Purify the crude mixture by chromatography on silica gel eluting with hexane/EtOAc mixtures.

Preparation 1

7-Chloro-3-(2,2,2-trifluoroacetyl)-6-trifluoromethanesulfonyloxy-2,3,4,5-tetrahydro-1H-benzo[d]azepine

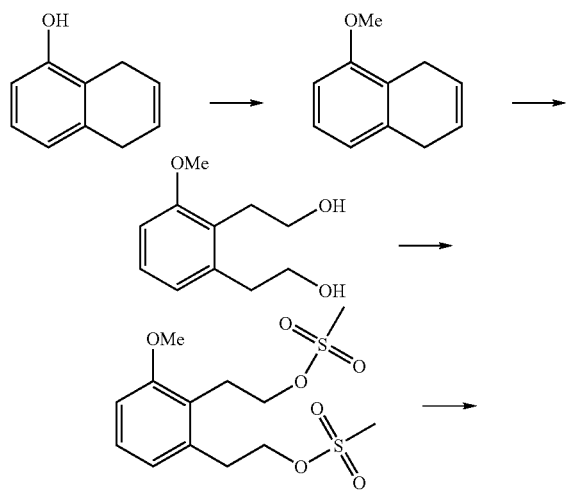

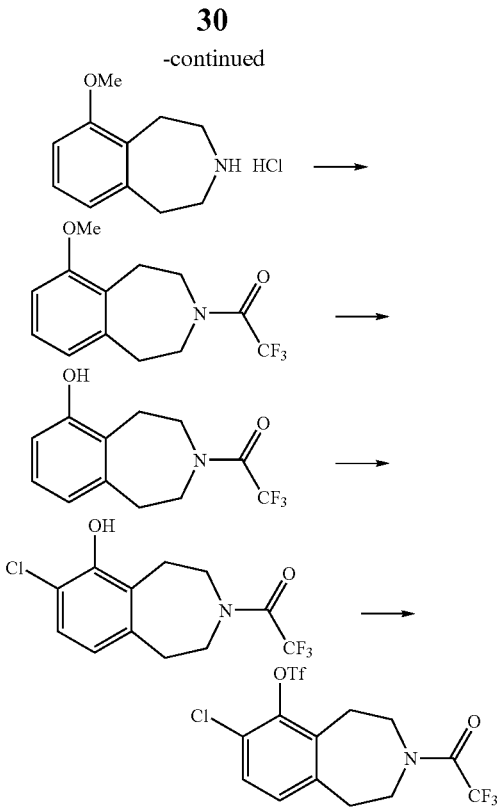

5-Methoxy-1,4-dihydronaphthalene: Add powdered potassium carbonate (193.1 g, 1.397 mol) to a solution of 5-hydroxy-1,4-dihydronaphthalene [68.08 g, 90% potency based on $^1$H-NMR, 0.4657 mol, from Societa Italiana Medicinala Scandicci, s.r.l., Reggello (Firenze), Italy] in ethanol (700 mL). Cool the solution to 0° C. with ice/water and add dimethyl sulfate (88.1 g, 66.1 mL, 0.699 mol) dropwise, maintaining the temperature between 5° C. and 10° C. Then heat the reaction mixture to 40° C. until the TLC (10:1 hexane/EtOAc) shows the absence of starting material (about 2 h). Filter off the solids by vacuum filtration and remove the solvent in vacuo. Dilute the residual brown oil with diethyl ether (500 mL), wash with 10% aqueous NH$_4$OH (500 mL), water (500 mL), brine (500 mL), dry the organic layer over Na$_2$SO$_4$, filter and concentrate in vacuo to give the crude product as a brown oil (73 g). Purify the crude product by short path distillation under vacuum (bp 120-130° C./5 Torr) to give the desired intermediate as a clear oil (69.0 g, 92.5% potency corrected) (contains some 1,2,3,4-tetrahydro-5-methoxynaphthalene as an impurity). $^1$H NMR (300 MHz, CDCl$_3$), δ 7.15 (t, 1H, J=7.9), 6.72 (dd, 2H, J=15.7, 7.9), 5.93-5.88 (m, 2H), 3.83 (s, 3H), 3.42-3.39 (m, 2H), 3.30-3.28 (m, 2H); R$_f$=0.58 eluting with 10:1 hexane/EtOAc.

2,3-Bis-(2-hydroxyethyl)-1-methoxybenzene: Charge a four-neck 5 L flask equipped with an over-head mechanical stirrer, reflux condenser, thermocouple, and gas dispersion apparatus with 5-methoxy-1,4-dihydronaphthalene (264.54 g, 89.5% potency based on $^1$H-NMR, 1.478 mol) in DCM (1.3 L) and 2B-3 ethanol (1 L). Add sudan III (10 mg) to give a faint red color. Cool the solution to −65° C. or lower, then pass O$_3$ through the solution until the solution turns a light yellow color and the TLC (10:1 hexane/EtOAc, KMnO$_4$ stain) shows the absence of the starting material (about 30 h). Transfer the solution via cannula into a slurry of NaBH$_4$ (97.8 g, 2.59 mol) in 2B-3 ethanol (500 mL) cooled in ice/water. It is important that the temperature be maintained at or above 0°

C., as for example between 0° C. and 10° C., throughout the transfer to ensure the ozonide is completely reduced to the diol. After the transfer is complete, warm the solution to ambient temperature and stir for about 30 min. Cool the slurry to 0° C. with ice/water then slowly add acetone (540 mL, 7.4 mol) to remove excess $NaBH_4$. After all the solids dissolve, remove the solvent in vacuo. Dissolve the yellow solid in DCM (1 L) and water (1 L), separate the layers and extract the aqueous layer with DCM (750 mL). Wash the combined organic layers with brine (1.5 L), add toluene (750 mL) and remove the solvent in vacuo. Dissolve the solid in DCM (500 mL) with heating, then add toluene (750 mL) and concentrate the solution in vacuo to give the desired intermediate as a light yellow solid (283.7 g, 89% potency corrected, mp 82-83° C.) (contains 1,2,3,4-tetrahydro-5-methoxynaphthalene as an impurity (8.6%)). Further purify the product by vacuum drying overnight at 75° C., 5 Torr, to remove all but trace amount of the 1,2,3,4-tetrahydro-5-methoxynaphthalene impurity. $^1$H NMR (300 MHz, $CDCl_3$), δ 7.16 (dd, 1H, J=8.2, 7.6), 6.83 (s, 1H, J=7.0), 6.76 (s, 1H, J=8.2), 3.85-3.77 (m, 7H), 3.01-2.91 (m, 4H), 2.35 (s, 2H); $^{13}$C NMR (300 MHz, DMSO-$d_6$), δ 157.5, 138.9, 126.5, 125.2, 122.0, 108.4, 62.1, 60.5, 55.3, 36.1, 29.6; IR (Kr): 3006, 2960, 2886, 2829, 1583, 1461, 1440, 1264, 1091, 1041 $cm^{-1}$; MS (ES+) m/z 178 (M+H)$^+$; Anal. Calc'd for $C_{11}H_{16}O_3$: C, 67.32; H, 8.22; N, 0. Found: C, 67.26; H, 8.10; N, 0.21; $R_f$=0.23 eluting with 95:5 DCM/methanol.

2,3-Bis-(2-methanesulfonyloxyethyl)-1-methoxybenzene: To a slurry of 2,3-bis-(2-hydroxyethyl)-1-methoxybenzene (50.6 g, 0.258 mol, 1 equiv.) and triethylamine (78.3 g, 0.774 mol, 3 equiv.) in DCM (500 mL) at 0° C., add dropwise a solution of methanesulfonyl chloride (65.0 g, 0.567 mol, 2.2 equiv.) in DCM (100 mL) over 45 min. The addition is exothermic and the methanesulfonyl chloride is added at a rate to keep the temperature below 10° C. After the addition is complete, warm the reaction to ambient temperature. Wash the solution with water (2×500 mL), and then brine (750 mL). Dry the organic layer over $Na_2SO_4$, filter and concentrate in vacuo to obtain the desired intermediate as a dark yellow oil (87.4 g, 96.2%), which is used in the next reaction without further purification. An analytical sample is obtained by flash column chromatography eluting with 100% diethyl ether. $^1$H NMR (300 MHz, $CDCl_3$), δ 7.20 (t, 1H, J=7.9), 6.82 (s, 1H, J=7.2), 6.80 (s, 1H, J=8.2), 4.41-4.34 (m, 4H), 3.83 (s, 3H), 3.16-3.09 (m, 4H), 2.91 (s, 3H), 2.87 (s, 3H); $^{13}$C NMR (300 MHz, $CDCl_3$), δ 158.07, 136.55, 128.26, 123.34, 122.39, 109.24, 69.88, 69.08, 55.55, 37.35, 37.14, 32.57, 26.47; $^{13}$C NMR (300 MHz, DMSO-$d_6$), δ 157.58, 136.79, 127.81, 122.91, 122.00, 109.33, 70.19, 68.88, 55.55, 36.49, 36.47, 31.56, 25.72; IR (Kr): 1586.8, 1469.4, 1358.51, 1267.3, 1173.9, 1105.4, 972.4, 954.6, 914.3 $cm^{-1}$; MS (ES+) m/z 257 (M+H)$^+$; Anal. Calc'd. for $C_{13}H_{20}O_7S_2$: C, 44.31; H, 5.72; N, 0. Found: C, 44.22; H, 5.68; N, 0.13; $R_f$=0.72 eluting with 95:5 DCM/methanol.

6-Methoxy-2,3,4,5-tetrahydro-1H-benzo[d]azepine: Dissolve 2,3-bis-(2-methanesulfonyloxyethyl)-1-methoxybenzene (474.4 g, 1.346 mol) in acetonitrile (7 L) and split the mixture into two equal lots. In two separate runs, add concentrated aqueous $NH_4OH$ (3.5 L) and charge the solution to a pressure vessel (PARR apparatus). Heat the solution in a closed reactor to 100° C. over 20 min (internal pressure reaches about 100 psi), and maintain at 100° C. until the reaction is complete (about 1 h, HPLC monitored). Cool the reaction mixture to ambient temperature. Combine the two lots and remove the solvent in vacuo. Dissolve the residue in MTBE (3.5 L) and water (3.5 L). Adjust the pH to 6.5 using 2M aqueous NaOH or 1M aqueous HCl as appropriate (typically the pH is about pH=5.1 and the adjustment requires about 50 mL 2M aqueous NaOH). Discard the organic layer, adjust the aqueous layer to pH=13 using 50% NaOH (about 150 mL). Extract with MTBE (2×3.5 L), wash the combined organic layers with brine (3.5 L), dry over $Na_2SO_4$, filter and concentrate in vacuo to give the title compound as a crude yellow oil that solidifies upon standing (179.3 g). Use the material for the next step without further purification. Prepare an analytical sample by purification by two Kugelrohr distillations to give a clear oil that solidifies upon standing, mp 44.3-45.0° C. $^{13}$C NMR (300 MHz, DMSO-$d_6$), δ 156.1, 144.4, 130.3, 126.2, 121.5, 108.9, 55.5, 48.2, 47.9, 39.9, 29.1; MS (ES+) m/z 163 (M+H)$^+$; Anal. Calc'd for $C_{11}H_{15}NO$: C, 74.54; H, 8.53; N, 7.90. Found: C, 74.28; H, 8.62; N, 7.86.

6-Methoxy-2,3,4,5-tetrahydro-1H-benzo[d]azepine Hydrochloride: Dissolve crude 6-methoxy-2,3,4,5-tetrahydro-1H-benzo[d]azepine (35.1 g, 0.198 mol) in 2B-3 ethanol (250 mL), heat the solution to reflux and add 2M HCl in ethanol (108.9 mL, 0.218 mol, 1.1 equiv.). Slowly add heptane (700 mL) over 10 min, then remove the heating mantle and cool the solution to ambient temperature, and finally continue the cooling with an ice/water mixture. Collect the resulting solid by vacuum filtration and wash with cold ethanol:heptane (1:2) (3×100 mL), air-dry for 15 min under vacuum, then further dry the product in a vacuum oven at 60° C. for 1 h to give the desired intermediate as a white granular solid (35.53 g, 63%): mp 246.6-246.9° C.; $^1$H NMR (300 MHz, DMSO-$d_6$), δ 9.82 (broad s, 1H), 7.12 (dd, 1H, J=7.6, 7.9), 6.88 (d, 1H J=8.2), 6.78 (d, 1H, J=7.3), 3.75 (s, 3H), 3.20-3.00 (m, 8H); $^{13}$C NMR (300 MHz, DMSO-$d_6$), δ 156.2, 141.3, 127.4, 127.2, 121.6, 109.7, 55.7, 44.9, 44.7, 31.6, 21.7; MS (ES+) m/z 178 (M+H)$^+$; Anal. Calc'd for $C_{11}H_{15}ClNO$: C, 62.12; H, 7.11; N, 6.59. Found: C, 61.95; H, 7.64; N, 6.58.

6-Methoxy-3-(2,2,2-trifluoroacetyl)-2,3,4,5-tetrahydro-1H-benzo[d]azepine: To a slurry of 6-methoxy-2,3,4,5-tetrahydro-1H-benzo[d]azepine hydrochloride (35.3 g, 0.165 mol, 1 equiv.) and triethylamine (69.1 mL, 0.496 mol, 3 equiv.) in DCM (300 mL) cooled at 0° C. with ice/water, add dropwise a solution of trifluoroacetic anhydride (25.7 mL, 0.182 mol, 1.1 equiv.) in DCM (40 mL) over 30 min, but at a rate that maintains the temperature below 10° C. After the addition is complete, warm the reaction mixture to ambient temperature and stir until the reaction is complete (verify by TLC using 9:1 $CH_2Cl_2$:methanol, about 2 h.). Wash the solution with water (2×350 mL), and then brine (350 mL), dry the organic layer over $Na_2SO_4$, filter and concentrate in vacuo to give desired intermediate as a yellow oil that solidifies upon standing (44.9 g, 96%). Use the material without further purification in the next step. Prepare an analytical sample by chromatography on silica gel eluting with 40% diethyl ether in hexane, mp 74-76° C. $^1$H NMR (300 MHz, $CDCl_3$), δ 7.16-7.11 (m, 1H), 6.81-6.74 (m, 2H), 3.81 (s, 3H), 3.79-3.64 (m, 4H), 3.11-3.07 (m, 2H), 2.99-2.95 (m, 2H); $^1$H NMR (300 MHz, DMSO-$d_6$), δ 7.13 (dd, 1H, J=1.5, 7.0), 7.08 (d, 1H, J=1.5), 6.88-6.74 (m, 1H), 3.75 (s, 3H), 3.67-3.61 (m, 4H), 3.04-2.92 (m, 4H); $^{13}$C NMR (300 MHz, DMSO-$d_6$), δ 156.43. 156.38, 155.06, 155.00, 154.60, 154.54, 154.14, 154.08, 141.31, 141.04, 127.44, 127.18, 127.05, 127.01, 122.27, 121.94, 121.90, 118.46, 114.64, 110.80, 109.52, 109.41, 55.63, 55.61, 47.11, 47.07, 46.67, 46.63, 45.61, 45.16, 35.90, 34.65, 26.18, 24.91; Anal. Calc'd for $C_{13}H_{14}F_3NO_2$: C, 57.14; H, 5.16; N, 5.13. Found: C, 57.17; H, 5.27; N, 5.08.

6-Hydroxy-3-(2,2,2-trifluoroacetyl)-2,3,4,5-tetrahydro-1H-benzo[d]azepine: To a 1M solution of $BBr_3$ (1.1 L, 1.6 equiv.), cooled at 0° C. with an ice-water bath, add 6-methoxy-3-(2,2,2-trifluoroacetyl)-2,3,4,5-tetrahydro-1H-benzo

[d]azepine (187 g, 0.684 mol) in DCM (200 mL) over 1 h., while maintaining the temperature between 0° C. and 10° C. Warm the reaction mixture to ambient temperature and stir until HPLC indicates completion of the reaction (about 2 h.). Cool the solution to 0° C. and transfer it via cannula into an ice/water solution (1.2 L), thereby precipitating the product as a white solid. Add EtOAc (2 L) to dissolve most of the precipitate, separate the layers and concentrate the organic layer in vacuo. Extract the aqueous layer three times with EtOAc (2×2 L, 1×1 L). Wash the combined organic layers with water (2 L), and then brine (2 L), dry over $Na_2SO_4$, filter and concentrate in vacuo to give the desired intermediate as a light yellow solid (166.3 g, 94%). Use the product for the next step without further purification. Prepare an analytical sample by chromatography on silica gel eluting with 40% diethyl ether in hexane: mp 183.0-185.2° C. $^1H$ NMR (300 MHz, DMSO-$d_6$), δ 9.39 (s, 1H), 6.94-6.88 (m, 1H), 6.72-6.68 (m, 1H), 6.61-6.57 (m, 1H), 3.67-3.32 (m, 4H), 2.99-2.86 (m, 4H); $^{13}C$ NMR (300 MHz, DMSO-$d_6$), δ 154.50, 141.47, 141.18, 126.77, 126.64, 125.77, 125.33, 120.38, 120.32, 118.49, 114.67, 113.64, 113.47, 47.31, 47.27, 47.00, 46.96, 45.83, 45.49, 36.17, 34.93, 26.46, 25.18, 20.66, 14.00; MS (ES+) m/z 260 (M+H)$^+$; Anal. Calc'd. for $C_{12}H_{12}F_3NO_2$: C, 55.60; H, 4.67; N, 5.40. Found: C, 55.51; H, 4.71; N, 5.29.

7-Chloro-6-hydroxy-3-(2,2,2-trifluoroacetyl)-2,3,4,5-tetrahydro-1H-benzo[d]azepine: Heat a mixture of 6-hydroxy-3-(2,2,2-trifluoroacetyl)-2,3,4,5-tetrahydro-1H-benzo[d]azepine (120 g, 0.4629 mol) and toluene (14.4 L) to 70° C. for 45 min until most of the starting material is dissolved. Add diisobutylamine (1.197 g, 1.62 mL, 9.26 mmol) followed by addition of sulfuryl chloride (62.48 g, 37.19 mL, 0.463 mol) in toluene (360 mL) over 20 min. Stir the reaction mixture for 50 min and then add additional sulfuryl chloride (4.536 g, 2.70 mL, 0.0336 mol) neat and stir the reaction mixture for 15 min at 70° C. Cool the reaction mixture to 24° C. over 30 min and then add 1N hydrochloric acid (2.00 L). Separate, wash the organic layer with saturated aqueous $NaHCO_3$ (2.00 L), brine (2.00 L) and then dry over $Na_2SO_4$. Filter and remove the solvent with a rotary evaporator at 70° C. until about 672.5 g remains using the minimum effective vacuum in order to maintain a vapor phase sufficient to prevent drying above the solvent line and self-seeding, thus preventing crystallization under these conditions. Using toluene heated to 70° C., transfer the light-yellow solution to a preheated (70° C.) 3-neck flask equipped with a mechanical stirrer. Lower the temperature to 58° C. over 1 h. If available, seed the solution with crystals of 7-chloro-6-hydroxy-3-(2,2,2-trifluoroacetyl)-2,3,4,5-tetrahydro-1H-benzo[d]azepine from a prior synthesis to enhance crystallization. After 30 min, reduce the temperature further to 55° C. and observe the initiation of the crystallization process. Hold the temperature at 55° C. for 2 h followed by 4 h at 45° C., then turn off the heat allowing the mixture to slowly reach 24° C. (ambient temperature). After stirring for 8 h with the heat off, cool the mixture to 0° C. for 2 h followed by 2 h at −10° C. Collect the resulting dense, white, granular crystals by vacuum filtration at −10° C. Rinse the crystals twice with cold (−10° C.) toluene and vacuum dry at 50° C., 5 Torr, for 12 h., to obtain the desired intermediate as a white solid (120.7 g, 99.5% purity, 88.8%): mp 133-134° C. MS (ES+) m/z 294 (M+H)$^+$. Anal. Calc'd for $C_{12}H_{11}ClF_3NO_2$: C, 49.08; H, 3.78; N, 4.77; Cl, 12.07. Found: C, 49.01; H, 3.63; N, 4.72; Cl, 12.32.

7-Chloro-3-(2,2,2-trifluoroacetyl)-6-trifluoromethanesulfonyloxy-2,3,4,5-tetrahydro-1H-benzo[d]azepine: Cool a solution of 7-chloro-6-hydroxy-3-(2,2,2-trifluoroacetyl)-2,3,4,5-tetrahydro-1H-benzo[d]azepine (60 g, 0.204 mol), triethylamine (62.6 mL, 0.448 mol, 2.2 equiv.), and DCM (590 mL) in an ice bath and add dropwise trifluoromethanesulfonic anhydride (43.5 mL, 0.258 mol, 1.26 equiv.) over 70 min. Remove the ice bath and stir the reaction mixture for 2 h. Wash the reaction mixture sequentially with water (500 mL), 1N aqueous HCl (500 mL), water (500 mL), and brine (500 mL). Dry the organic layer over $Na_2SO_4$ and concentrate in vacuo to give the crude product as a brown solid (90 g). Dissolve the solid in warm toluene (200 mL). Further purify by plug filtration chromatography over silica gel (500 g) eluting sequentially with hexane (1 L), hexane/EtOAc (9:1, 1 L), hexane/EtOAc (4:1, 1 L), and hexane/EtOAc (7:3, 9 L). Pool the eluents and evaporate the solvent to obtain the product as a yellow tan solid (86.3 g). Dissolve the solid in warm EtOAc (86 mL) and then add hexane (700 mL). If available, seed the solution with crystals of 7-chloro-3-(2,2,2-trifluoroacetyl)-6-trifluoromethylsulfonyloxy-2,3,4,5-tetrahydro-1H-benzo[d]azepine from a prior synthesis to enhance crystallization. Allow the mixture to stand at ambient temperature for 30 min. Cool the mixture at about −10° C. for 2 h., filter, rinse the crystals with cold (−10° C.) hexane/EtOAc, and air-dry on the filter under vacuum to obtain the title compound as a first crop of crystals (73.54 g). Concentrate the mother liquor to obtain a solid (12.7 g). Recrystallize the solid in a mixture of EtOAc/hexane (15 mL: 121 mL) to obtain additional title compound (7.65 g, total yield: 81.19 g, 93%).

Preparation 2

6-Bromomethyl-3-tert-butoxycarbonyl-7-chloro-2,3,4,5-tetrahydro-1H-benzo[d]azepine

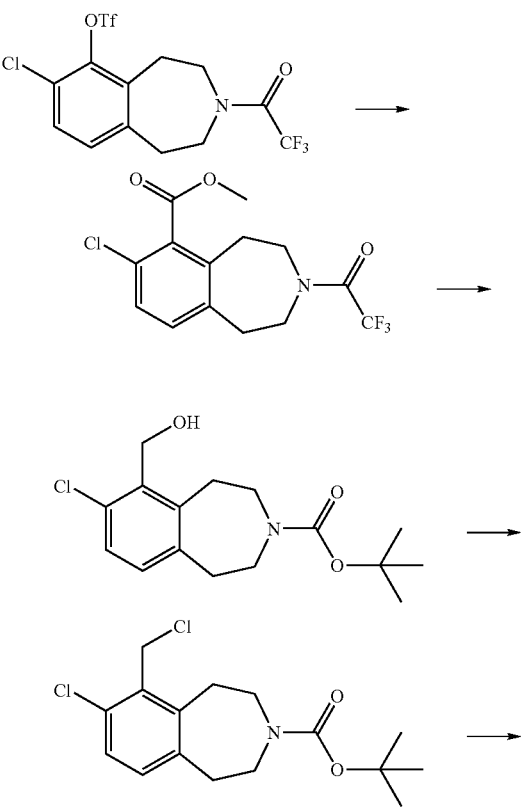

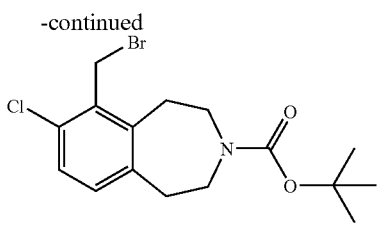

7-Chloro-6-(methoxycarbonyl)-3-(2,2,2-trifluoroacetyl)-2,3,4,5-tetrahydro-1H-benzo[d]azegine: Add 7-chloro-3-(2,2,2-trifluoroacetyl)-6-trifluoromethanesulfonyloxy-2,3,4,5-tetrahydro-1H-benzo[d]azepine (3 g, 7.1 mmol), triethylamine (3.2 mL, 16.2 mmol), palladium(II) acetate (52 mg, 0.23 mmol) and DPPP (92 mg, 0.23 mmol) to anhydrous DMSO (20 mL) and methanol (7 mL) in a pressure vessel. Flush the mixture three times with carbon monoxide at 50 psi. Charge the mixture with carbon monoxide at 50 psi and heat at 60° C. for 12 h. Cool the mixture to room temperature and dilute with water and EtOAc. Extract the aqueous phase with EtOAc. Wash the combined organic extracts with water and brine. Dry the organic layer over $Na_2SO_4$, filter and concentrate in vacuo. Purify the crude mixture by chromatography on silica gel eluting with hexane/EtOAc (20:1 and 1:1) to obtain the desired intermediate as a clear oil (2.19 g, 88%). MS (APCI+) m/z: 304 (M-MeOH+H)$^+$.

3-tert-Butoxycarbonyl-7-chloro-6-hydroxymethyl-2,3,4,5-tetrahydro-1H-benzo[d]azepine: Dissolve 7-chloro-6-(methoxycarbonyl)-3-(2,2,2-trifluoroacetyl)-2,3,4,5-tetrahydro-1H-benzo[d]azepine (2.62 g, 7.8 mmol) in anhydrous THF (75 mL) under nitrogen and add 1M lithium aluminum hydride in THF (22.05 mL). Warm the reaction to 35° C. and stir for 3.5 h. Cool the reaction to 0° C. and add sequentially water (0.85 mL), 15% aqueous NaOH (0.85 mL) and water (2.6 mL). Filter the insoluble salts and wash with THF. Concentrate in vacuo to obtain a white solid (1.92 g). Suspend the solid in dichloromethane (20 mL). Add di-tert-butyl-dicarbonate (2.26 g, 10.3 mmol) and triethylamine (1.2 mL, 8.6 mmol). Stir at room temperature for 12 h, dilute the reaction with dichloromethane and wash with water followed by brine. Dry the organic phase over $MgSO_4$, filter and concentrate in vacuo to obtain a yellow oil. Purify by chromatography on silica gel eluting with hexane/EtOAc (9:1) to obtain the desired intermediate as a white solid (1.52 g, 62%). MS (ES+) m/z: 212 (M-Boc+H)$^+$.

3-tert-Butoxycarbonyl-7-chloro-6-chloromethyl-2,3,4,5-tetrahydro-1H-benzo[d]azepine: Add methanesulfonyl chloride (1.1 g, 9.63 mmol; alternatively 2.36 g, 20.7 mmol) to 3-tert-butoxycarbonyl-7-chloro-6-hydroxymethyl-2,3,4,5-tetrahydro-1H-benzo[d]azepine (2.5 g, 8.03 mmol; alternatively 3.2 g, 10.3 mmol) and triethylamine (2.2 mL, 16.06 mmol; alternatively 4.3 mL, 30.8 mmol) in DCM (50 mL; alternatively 60 mL) at 0° C. Warm the mixture to room temperature and stir for 1 h., alternatively for 16 h. Dilute the reaction with DCM and wash the organic phase with water. Dry the organic phase over $Na_2SO_4$, filter and concentrate in vacuo to afford the title compound as a clear oil that was used immediately without any further purification. MS (ES+) m/z: 274 [M-(t-Bu)+H]$^+$.

6-Bromomethyl-3-tert-butoxycarbonyl-7-chloro-2,3,4,5-tetrahydro-1H-benzo[d]azepine: Combine 3-tert-butoxycarbonyl-7-chloro-6-chloromethyl-2,3,4,5-tetrahydro-1H-benzo[d]azepine (3.17 g, 8.14 mmol) and lithium bromide (0.98 g, 11.3 mmol) in anhydrous THF (60 mL) and stir at room temperature for 1 h. Concentrate in vacuo and partition the residue between dichloromethane/water. Dry the organic phase over $Na_2SO_4$, filter and concentrate in vacuo. Purify the crude mixture by chromatography on silica gel eluting with hexane/EtOAc (1:0 and 10:1) to obtain the title compound as a white solid (2.6 g, 85%). MS (APCI+) m/z: 274 (M-Boc+H)$^+$.

Preparation 3

3-(2,2,2-Trifluoroacetyl)-6-trifluoromethanesulfonyloxy-2,3,4,5-tetrahydro-1H-benzo[d]azepine

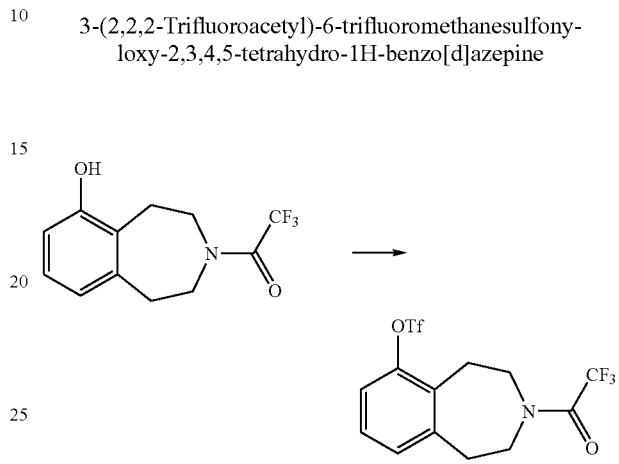

Cool a solution of 6-hydroxy-3-(2,2,2-trifluoroacetyl)-2,3,4,5-tetrahydro-1H-benzo[d]azepine (2 g, 7.72 mmol), triethylamine (1.4 mL, 10.1 mmol) and DCM (50 mL) in a cryogenic bath set at −30° C. and add dropwise trifluoromethanesulfonic anhydride (1.7 mL, 10.1 mmol) over 20 min. Stir at −30° C. for 2 h and then warm to ambient temperature overnight. Wash the reaction mixture sequentially with water (100 mL), 1N aqueous HCl (100 mL), water (200 mL), and brine (200 mL). Dry the organic layer over $Na_2SO_4$ and concentrate in vacuo to give the title compound as a colorless to light yellow oil (2.7 g, 89%) suitable for use without purification. Obtain an analytical sample by chromatography on silica gel eluting with hexane/EtOAc (9:1) to give the title compound as an off-white waxy solid. GC-MS m/z: 391 (M$^+$).

Preparation 4

7-Chloro-6-(2-pyridin-2-yl-ethyl)-3-(2,2,2-trifluoroacetyl)-2,3,4,5-tetrahydro-1H-benzo[d]azepine and 7-Chloro-6-(2-pyridin-2-yl-vinyl)-3-(2,2,2-trifluoroacetyl)-2,3,4,5-tetrahydro-1H-benzo[d]azepine

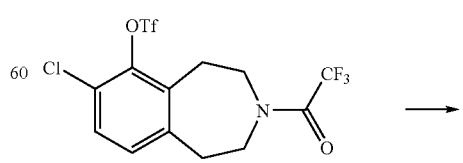

-continued

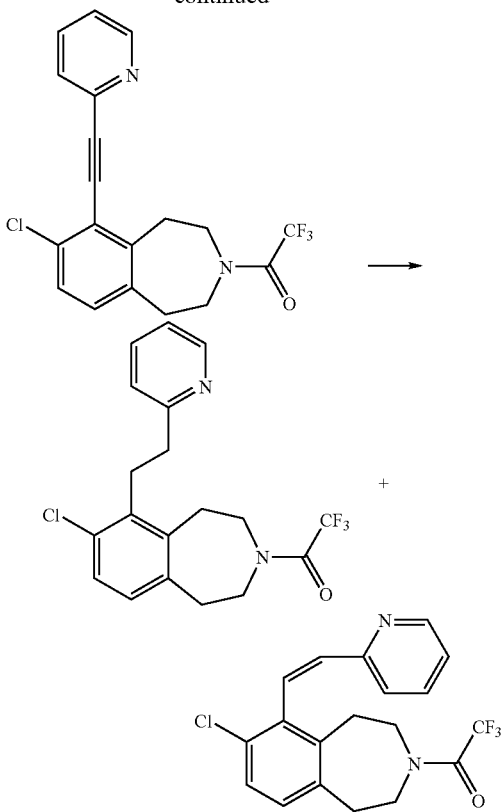

7-Chloro-6-pyridin-2-ylethynyl-3-(2,2,2-trifluoroacetyl)-2,3,4,5-tetrahydro-1H-benzo[d]azepine: Use a method simi-lar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) and 2-ethynyl-pyridine (0.2 mL, 2 mmol) in triethylamine/DMF (2, 10 mL). Heat at 80° C. for 2 h in a sealed tube. Purify the crude mixture by chromatography on silica gel eluting with isohexane/EtOAc (1:0 to 1:1 gradient over 40 min) to obtain the desired intermediate (342 mg, 90%). MS (ES+) m/z: 379 (M+H)$^+$.

7-Chloro-6-(2-pyridin-2-yl-ethyl)-3-(2,2,2-trifluoro-acetyl)-2,3,4,5-tetrahydro-1H-benzo[d]azepine and 7-chloro-6-(2-Myridin-2-yl-vinyl)-3-(2,2,2-trifluoroacetyl)-2,3,4,5-tetrahydro-1H-benzo[d]azepine: Add a solution of 7-chloro-6-pyridin-2-ylethynyl-3-(2,2,2-trifluoroacetyl)-2,3,4,5-tetrahydro-1H-benzo[d]azepine (202 mg, 0.53 mmol) in ethanol (10 mL) to a suspension of 10% Pd/C (Degussa type E101, 200 mg), then acetic acid (0.5 mL). Hydrogenate for 10 h at 68-70 psi then filter the catalyst through Celite® and concentrate in vacuo. Purify by chromatography on silica gel eluting with isohexane/EtOAc (1:0 to 1:1 gradient over 40 min) to obtain a mixture of 7-chloro-6-(2-pyridin-2-yl-ethyl)-3-(2,2,2-trifluoroacetyl)-2,3,4,5-tetrahydro-1H-benzo[d]azepine [(103 mg, 51%), MS (ES+) m/z: 383 (M+H)$^+$] and 7-chloro-6-(2-pyridin-2-yl-vinyl)-3-(2,2,2-trifluoroacetyl)-2,3,4,5-tetrahydro-1H-benzo[d]azepine [(80 mg, 40%), MS (ES+) m/z: 381 (M+H)$^+$].

Preparations 5-11

The compounds of Preparations 5-11 may be prepared essentially as described in Preparation 4 by using 7-chloro-3-(2,2,2-trifluoroacetyl)-6-trifluoromethanesulfonyloxy-2,3,4,5-tetrahydro-1H-benzo[d]azepine and the appropriately substituted alkyne. Overall yields and MS (ES+) data are shown in the Table below.

| Prep. | Structure | Compound | Yield (%) | MS (ES+) m/z |
|---|---|---|---|---|
| 5 | 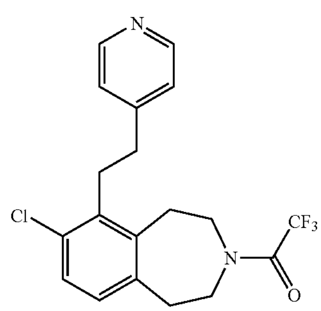 [SMILES: O=C(N1CCc2ccc(Cl)c(CCc3ccncc3)c2CC1)C(F)(F)F] | 7-Chloro-6-(2-pyridin-4-yl-ethyl)-3-(2,2,2-trifluoroacetyl)-2,3,4,5-tetrahydro-1H-benzo[d]azepine | 60 | 383 (M + H)$^+$ |
| 6 | 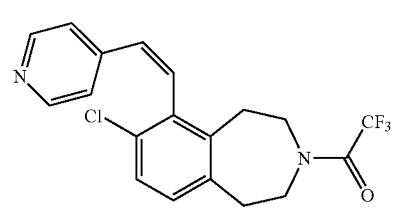 [SMILES: O=C(N1CCc2ccc(Cl)c(/C=C\c3ccncc3)c2CC1)C(F)(F)F] | 7-Chloro-6-(2-pyridin-4-yl-vinyl)-3-(2,2,2-trifluoroacetyl)-2,3,4,5-tetrahydro-1H-benzo[d]azepine | 28 | 381 (M + H)$^+$ |

-continued

| Prep. | Structure | Compound | Yield (%) | MS (ES+) m/z |
|---|---|---|---|---|
| 7 | 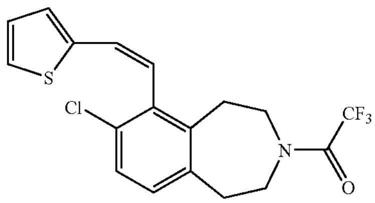 [SMILES: O=C(N1CCc2ccc(Cl)c(/C=C\c3cccs3)c2CC1)C(F)(F)F] | 7-Chloro-6-(2-thiophen-2-yl-vinyl)-3-(2,2,2-trifluoroacetyl)-2,3,4,5-tetrahydro-1H-benzo[d]azepine | 19 | 385 (M + H)+ |
| 8 | 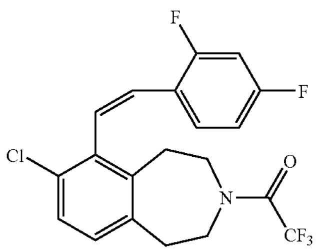 [SMILES: O=C(N1CCc2ccc(Cl)c(/C=C\c3ccc(F)cc3F)c2CC1)C(F)(F)F] | 7-Chloro-6-[2-(2,4-difluorophenyl)-vinyl]-3-(2,2,2-trifluoroacetyl)-2,3,4,5-tetrahydro-1H-benzo[d]azepine | 35 | 416 (M + H)+ |
| 9 | 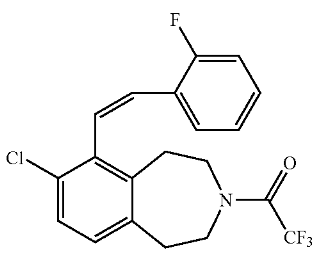 [SMILES: O=C(N1CCc2ccc(Cl)c(/C=C\c3ccccc3F)c2CC1)C(F)(F)F] | 7-Chloro-6-[2-(2-fluorophenyl)vinyl]-3-(2,2,2-trifluoroacetyl)-2,3,4,5-tetrahydro-1H-benzo[d]azepine | 68 | 398 (M + H)+ |
| 10 | 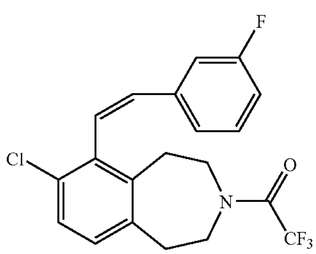 [SMILES: O=C(N1CCc2ccc(Cl)c(/C=C\c3cccc(F)c3)c2CC1)C(F)(F)F] | 7-Chloro-6-[2-(3-fluorophenyl)-vinyl]-3-(2,2,2-trifluoroacetyl)-2,3,4,5-tetrahydro-1H-benzo[d]azepine | 19 | 398 (M + H)+ |
| 11 | 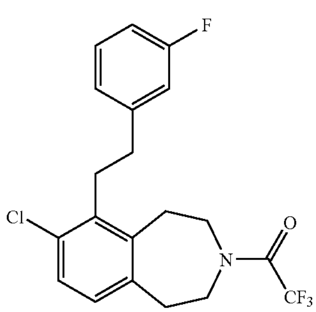 [SMILES: O=C(N1CCc2ccc(Cl)c(CCc3cccc(F)c3)c2CC1)C(F)(F)F] | 7-Chloro-6-[2-(3-fluorophenyl)-ethyl]-3-(2,2,2-trifluoroacetyl)-2,3,4,5-tetrahydro-1H-benzo[d]azepine | 19 | 400 (M + H)+ |

Preparation 12

7-Chloro-6-(2-pyridin-3-yl-ethyl)-2,3,4,5-tetrahydro-1H-benzo[d]azepine and 7-Chloro-6-(2-pyridin-3-yl-vinyl)-2,3,4,5-tetrahydro-1H-benzo[d]azepine

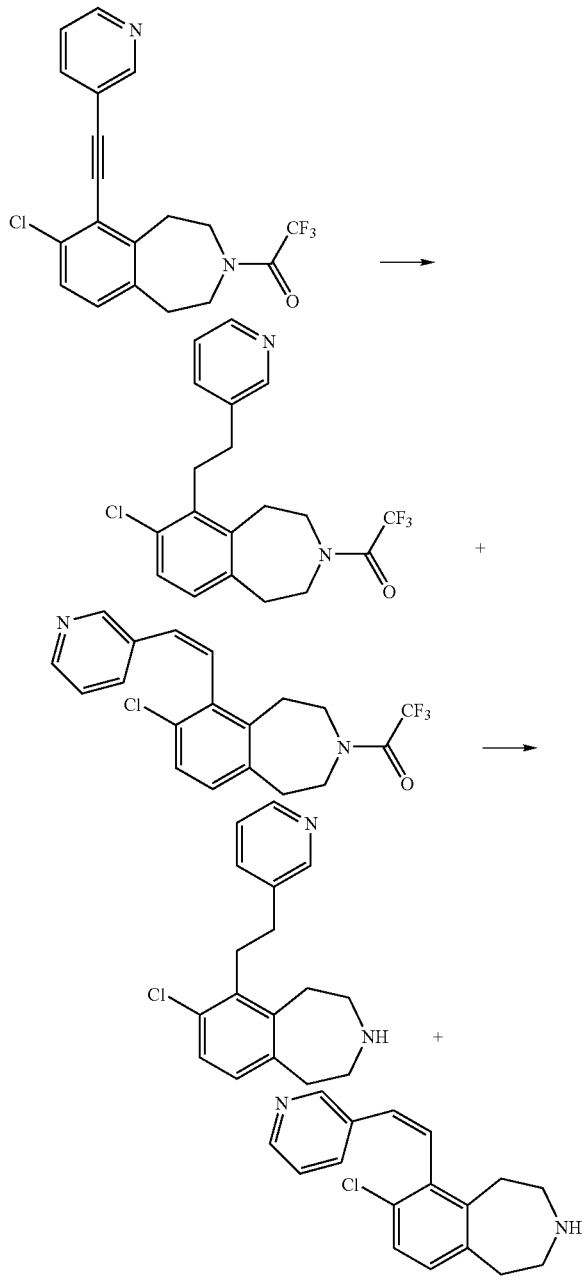

7-Chloro-6-(2-pyridin-3-yl-ethyl)-3-(2,2,2-trifluoro-acetyl)-2,3,4,5-tetrahydro-1H-benzo[d]azepine and 7-chloro-6-(2-pyridin-3-yl-vinyl)-3-(2,2,2-trifluoroacetyl)-2,3,4,5-tetrahydro-1H-benzo[d]azepine: Add a solution of 7-chloro-6-pyridin-3-ylethynyl-3-(2,2,2-trifluoroacetyl)-2,3,4,5-tetrahydro-1H-benzo[d]azepine (283 mg, 0.75 mmol) in ethanol (15 mL) to a suspension of 10% Pd/C (Degussa type E101, 320 mg), then acetic acid (0.75 mL). Hydrogenate for 16 h at 68-70 psi. Add 10% Pd/C (Degussa type E101, 200 mg), and acetic acid (1 mL) then hydrogenate for 3 h. Filter through Celite® and concentrate in vacuo. Purify by chromatography on silica gel eluting with isohexane/EtOAc (1:0 to 1:1 gradient over 40 min) to obtain a mixture of the desired intermediates (195 mg, 68%). MS (ES+) m/z: 383 and 381 (M+H)$^+$.

7-Chloro-6-(2-pyridin-3-yl-ethyl)-2,3,4,5-tetrahydro-1H-benzo[d]azepine and 7-chloro-6-(2-pyridin-3-yl-vinyl)-2,3,4,5-tetrahydro-1H-benzo[d]azepine: Use a method similar to the General Procedure 1-2 to deprotect a mixture of 7-chloro-6-(2-pyridin-3-yl-ethyl)-3-(2,2,2-trifluoroacetyl)-2,3,4,5-tetrahydro-1H-benzo[d]azepine and 7-chloro-6-(2-pyridin-3-yl-vinyl)-3-(2,2,2-trifluoroacetyl)-2,3,4,5-tetrahydro-1H-benzo[d]azepine (195 mg, 0.511 mmol). Elute through SCX column, then separate by HPLC [Luna-CN-(3717) column; flow rate: 1 mL/min; eluting with heptane/ethanol/isopropylamine (90:10:0.2) over 15 min] to obtain 7-chloro-6-(2-pyridin-3-yl-ethyl)-2,3,4,5-tetrahydro-1H-benzo[d]azepine as a brown solid [(53 mg, 34%), MS (ES+) m/z: 303 (M+H)$^+$] and 7-chloro-6-(2-pyridin-3-yl-vinyl)-2,3,4,5-tetrahydro-1H-benzo[d]azepine as a light brown oil [(31 mg, 20%), MS (ES+) m/z: 301 (M+H)$^+$].

Preparation 13

1-But-3-ynyl-imidazolidin-2-one

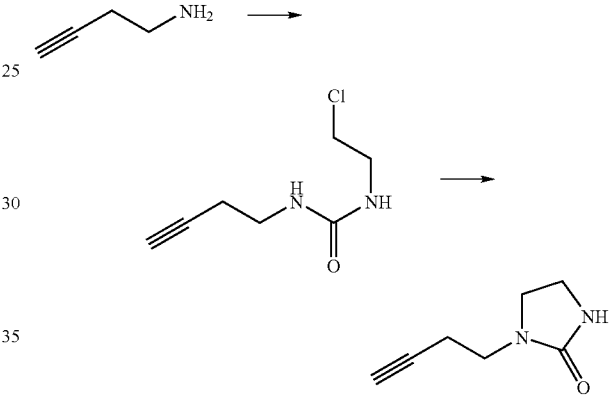

1-But-3-ynyl-3-(2-chloro-ethyl)-urea: Add chloroethyl isocyanate (5.25 g, 50 mmol) dropwise to a solution of but3-ynyl-amine (3.4 g, 50 mmol) (prepared by following the procedure described in *Tetrahedron Lett.* 1987, 43, 5145) in ethyl ether (100 mL). Stir the suspension for 30 min and filter the solid to obtain the desired intermediate (8.7 g, 100%).

1-But-3-ynyl-imidazolidin-2-one: To a solution of 1-but-3-ynyl-3-(2-chloro-ethyl)-urea (5 g, 28.7 mmol) in THF (100 mL) add tetrabutylammonium bromide (1.82 g, 5.65 mmol) and potassium hydroxide (2.01 g, 35.9 mmol). Heat the resulting suspension at 75° C. for 72 h and allow to cool to room temperature. Dilute the mixture with EtOAc (200 mL), wash with water (2×100 mL) and 1N aqueous HCl (100 mL). Dry the organic phase over MgSO$_4$, filter and concentrate in vacuo to obtain the title compound as a white powder (816 mg, 21%).

Preparation 14

3-Prop-2-ynyl-imidazolidine-2,4-dione

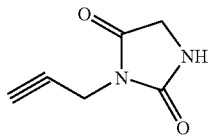

To a solution of hydantoin (10 g, 100 mmol) in THF (150 mL) add tetrabutylammonium bromide (4 g, 12.3 mmol), potassium hydroxide (5.6 g, 100 mmol) and then propargyl bromide (11.9 g, 100 mmol). Heat the mixture to 75° C. for 18 h. Dilute the mixture with EtOAc (200 mL), wash with water (2×100 mL) and 1N aqueous HCl (100 mL). Dry the organic phase over MgSO$_4$, filter and concentrate in vacuo to obtain the title compound as a yellow powder (8.3 g, 60%). Triturate the solid with diethyl ether (100 mL) to obtain the title compound as a white crystalline solid (7.8 g, 56%).

Preparation 15

The compound of Preparation 15 may be prepared essentially as described in Preparation 14 by using hydantoin and 5-chloro-1-pentyne. Purify by chromatography on silica gel eluting with diethyl ether/methanol (1:0 to 95:5). Yield is shown in the Table below.

| Prep. | Structure | Compound | Yield (%) |
|---|---|---|---|
| 15 | 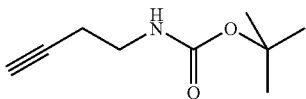 | 3-Pent-4-ynyl-imidazolidine-2,4-dione | 38 |

Preparation 16

But-3-ynyl-carbamic acid tert-butyl ester

Add triethylamine (3 mL) to a solution of 4-pentynoic acid (1.96 g, 20 mmol) in tert-butanol (6 mL) at 0° C. and then add diphenyl phosphoryl azide (CAUTION: reaction starts violently a short period after the addition). Heat the reaction mixture at 85° C. overnight under nitrogen. Concentrate in vacuo and purify the crude mixture by chromatography on silica gel eluting with dichloromethane to obtain the title compound as a white solid (1.81 g, 53%).

Preparation 17

The compound of Preparation 17 may be prepared essentially as described in Preparation 16 by using 5-hexynoic acid. Yield is shown in the Table below.

Preparation 18

N-But-3-ynyl-2,2-dimethyl-propionamide

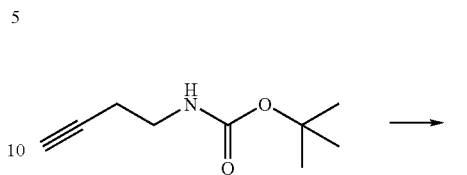

But-3-ynylamine hydrochloride: Dissolve but-3-ynyl-carbamic acid tert-butyl ester (1.81 g, 0.1 mmol) in DCM (5 mL) and add 5N aqueous HCl (5 mL). Stir vigorously at room temperature overnight. Concentrate in vacuo to a minimum amount of volume and then freeze dry to obtain the desired material as a white solid (809 mg, 79%).

N-But-3-ynyl-2,2-dimethyl-propionamide: Add triethylamine (3 mL) to a suspension of but-3-ynylamine hydrochloride (200 mg, 2.1 mmol) in DCM (10 mL) and stir for 10 min at room temperature under nitrogen. Add then neat pivaloyl chloride (284.9 µL, 2.31 mmol) and stir at room temperature overnight under nitrogen. Concentrate in vacuo, take up the residue in methanol and filter through a SCX-2 cartridge eluting with methanol to obtain the title compound (265 mg, 65%).

Preparations 19-22

The compound of Preparations 19-22 may be prepared essentially as described in Preparation 18 by using but-3-ynyl-carbamic acid tert-butyl ester or pent-3-ynyl-carbamic acid tert-butyl ester and the corresponding acid chloride. Yields are shown in the Table below.

| Prep. | Structure | Compound | Yield (%) |
|---|---|---|---|
| 17 | 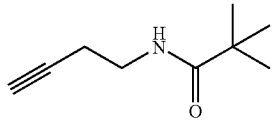 | Pent-4-ynyl-carbamic acid tert-butyl ester | 67 |

| Prep. | Structure | Compound | Yield (%) |
|---|---|---|---|
| 19 | 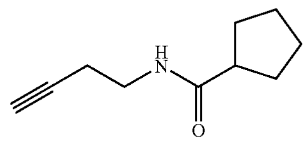 | N-But-3-ynyl-cyclopentylcarboxamide | 78 |
| 20 | 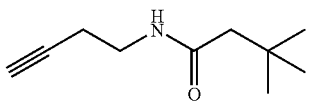 | N-But-3-ynyl-3,3-dimethyl-butyramide | 63 |
| 21 | 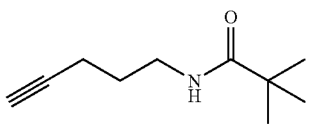 | N-Pent-4-ynyl-2,2-dimethyl-propionamide | 56 |
| 22 | 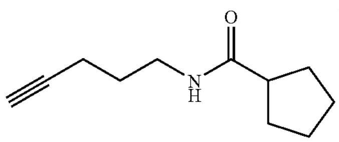 | N-Pent-4-ynyl-cyclopentylcarboxamide | 50 |

Preparation 23

N-prop-2-ynyl-cyclopentylcarboxamide

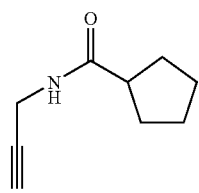

Dissolve propargylamine (1.5 g, 28.07 mmol) in DCM (50 mL), add triethylamine (7.83 mL, 56.15 mmol) and cool the mixture to 0° C. Add cyclopentanecarbonyl chloride (2.5 g, 18.72 mmol) and warm to room temperature. Stir the reaction mixture for 18 h. Wash the mixture with water (3×50 mL) and hydrochloric acid (2N, 50 mL) and dry the organic phase over MgSO$_4$. Remove the solvent in vacuo and triturate the solid with iso-hexane to give the title compound as a fine white powder (1.51 g, 53%).

Preparation 24

4-[(Cyclopentanecarbonyl-amino)-methyl]-phenyl-boronic acid

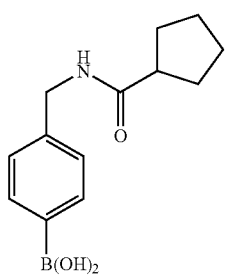 [SMILES: O=C(NCc1ccc(B(O)O)cc1)C1CCCC1]

Dissolve 4-aminomethylphenyl boronic acid hydrochloride (1.0 g, 5.34 mmol) in DCM (50 mL), add triethylamine (1.64 mL, 11.74 mmol) and cool the mixture to 0° C. Add cyclopentanecarbonyl chloride (778 mg, 5.78 mmol) and warm to room temperature. Stir the reaction mixture for 18 h, filter and wash the solid with DCM (10 mL) to give the title compound as a fine white powder (1.1 g, 83%).

Preparation 25

3-[(2,2,2-Trifluoroethyl-amino)-methyl]-phenyl-boronic acid

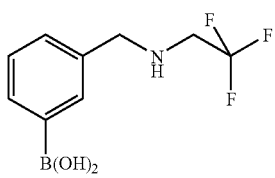 [SMILES: OB(O)c1cccc(CNCC(F)(F)F)c1]

Dissolve 3-formylphenyl boronic acid hydrochloride (2.5 g, 16.67 mmol) and 2,2,2,-trifluoroethylamine (2.97 g, 30.01 mmol) in DCM (100 mL). Add sodium triacetoxyborohydride (10.6 g, 50.02 mmol) portionwise over 10 min and stir the resulting solution for 72 h. Then quench with water (50 mw). Dry the organic fraction over MgSO$_4$, filter and concentrate in vacuo. Purify by chromatography on silica gel eluting with dichloromethane:methanol (1:0 to 19:1) to give the title compound as a colourless oil (1.41 g, 36%).

EXAMPLE 1

6-(Biphenyl-3-yl)-7-chloro-2,3,4,5-tetrahydro-1H-benzo[d]azepine Succinate

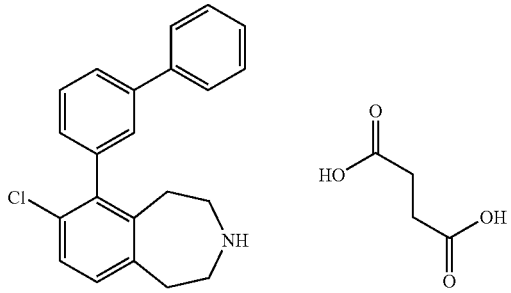 [SMILES: Clc1ccc2c(c1-c1cccc(-c3ccccc3)c1)CCNCC2 ; O=C(O)CCC(=O)O]

Combine 7-chloro-3-(2,2,2-trifluoroacetyl)-6-trifluoromethanesulfonyloxy-2,3,4,5-tetrahydro-1H-benzo[d]azepine (200 mg, 0.47 mmol), 3-biphenylboronic acid (280 mg, 1.4 mmol), tetrakis(triphenylphosphine)palladium(0) (54 mg, 0.047 mmol) and cesium fluoride (144 mg, 0.94 mmol) in anhydrous DME (8 mL) and reflux the mixture for 3 h. Cool the reaction mixture and partition between brine and EtOAc. Dry the organic layer over $Na_2SO_4$, filter and concentrate in vacuo. Purify the crude mixture by chromatography on silica gel eluting with hexane/EtOAc (1:0 to 7:3 gradient) to obtain 6-(biphenyl-3-yl)-7-chloro-3-(2,2,2-trifluoroacetyl)-2,3,4,5-tetrahydro-1H-benzo[d]azepine.

Use methods similar to the General Procedures 1-1 and 2-1 to obtain the title compound (120 mg, 56%). MS (ES+) m/z: 334 (M+H)$^+$.

EXAMPLE 2

7-Chloro-6-(2-methoxyphenyl)-2,3,4,5-tetrahydro-1H-benzo[d]azepine Succinate

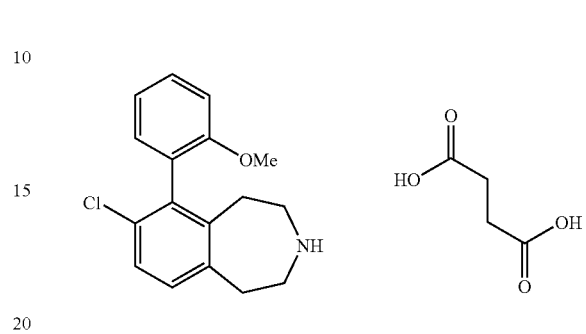

The title compound may be prepared essentially as described in Example 1, by using 7-chloro-3-(2,2,2-trifluoroacetyl)-6-trifluoromethanesulfonyloxy-2,3,4,5-tetrahydro-1H-benzo[d]azepine and 2-methoxyphenylboronic acid. Yield 58% MS (ES+) m/z: 288 (M+H)$^+$.

EXAMPLES 3-5

Examples 3-5 may be prepared essentially as described in Example 1, by using 7-chloro-3-(2,2,2-trifluoroacetyl)-6-trifluoromethanesulfonyloxy-2,3,4,5-tetrahydro-1H-benzo[d]azepine and the appropriate arylboronic acid. Use methods similar to the General Procedures 1-1 and 2-2 to obtain the title compounds. Overall yields and MS (ES+) data are shown in the Table below.

| Ex. | Structure | Compound | Yield (%) | MS (ES+) m/z |
|---|---|---|---|---|
| 3 | 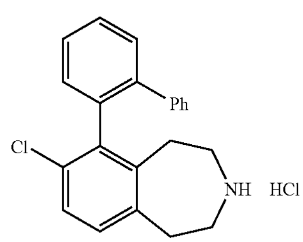 [SMILES: Clc1ccc2c(c1-c1ccccc1-c1ccccc1)CCNCC2 ; Cl] | 6-(Biphenyl-2-yl)-7-chloro-2,3,4,5-tetrahydro-1H-benzo[d]azepine Hydrochloride | 78 | 334 (M + H)$^+$ |
| 4 | 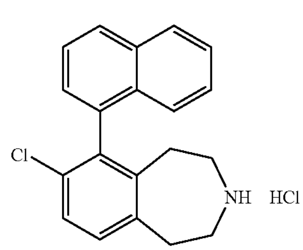 [SMILES: Clc1ccc2c(c1-c1cccc3ccccc13)CCNCC2 ; Cl] | 7-Chloro-6-(naphthalen-1-yl)-2,3,4,5-tetrahydro-1H-benzo[d]azepine Hydrochloride | 34 | 308 (M + H)$^+$ |

| Ex. | Structure | Compound | Yield (%) | MS (ES+) m/z |
|---|---|---|---|---|
| 5 | 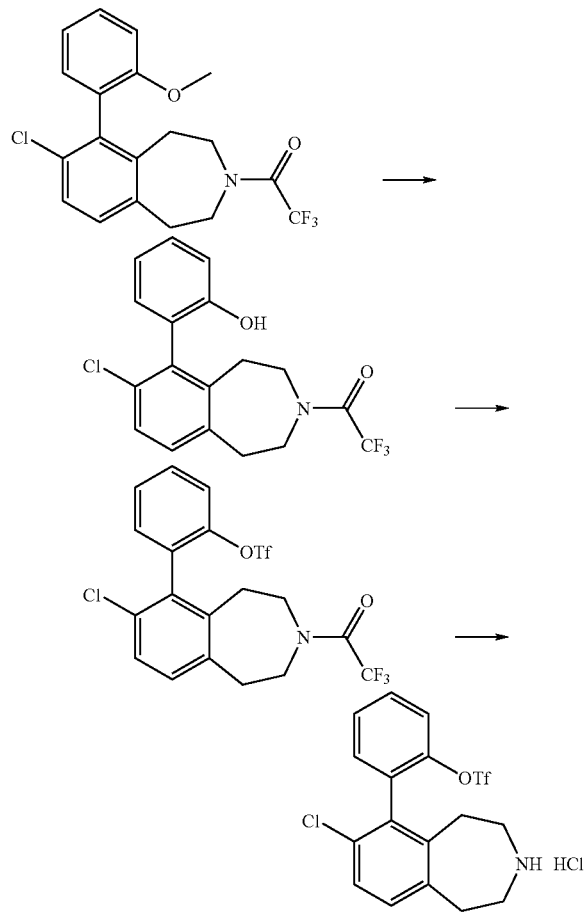 | 7-Chloro-6-(naphthalen-2-yl)-2,3,4,5-tetrahydro-1H-benzo[d]azepine Hydrochloride | 79 | 308 (M + H)+ |

EXAMPLE 6

7-Chloro-6-(2-trifluoromethylsulfonyloxyphenyl)-2,3,4,5-tetrahydro-1H-benzo[d]azepine Hydrochloride 7-Chloro-6-(2-hydroxyphenyl)-3-(2,2,2-trifluoroacetyl)-2,3,4,5-tetrahydro-1H-benzo[d]azepine: Cool boron tribromide (3.5 mL, 1M solution in dichloromethane) in dichloromethane at 0° C. and add dropwise a solution of 7-chloro-6-(2-methoxyphenyl)-3-(2,2,2-trifluoroacetyl)-2,3,4,5-tetrahydro-1H-benzo[d]azepine (840 mg, 2.19 mmol) in dichloromethane (5 mL). Stir at room temperature for 6 h. Partition between iced water and EtOAc. Dry the organic layer over Na₂SO₄, filter and concentrate in vacuo to obtain the desired intermediate as a white solid (800 mg, 99%).

74-Chloro-6-(2-trifluoromethylsulfonyloxyphenyl)-3-(2,2,2-trifluoroacetyl)-2,3,4,5-tetrahydro-1H-benzo[d]azepine: Dissolve 7-chloro-6-(2-hydroxyphenyl)-3-(2,2,2-trifluoroacetyl)-2,3,4,5-tetrahydro-1H-benzo[d]azepine (800 mg, 2.16 mmol) in dichloromethane at 0° C. and add pyridine (0.35 mL, 4.33 mmol) and slowly trifluoromethanesulfonic anhydride (732 mg, 2.16 mmol). Stir the mixture at room temperature for 2 h then pour into water and extract with dichloromethane. Dry the organic layer over Na₂SO₄, filter and concentrate in vacuo. Purify the crude mixture by chromatography on silica gel eluting with hexane/EtOAc (1:0 to 4:1 gradient) to obtain the desired intermediate (900 mg, 83%).

7-Chloro-6-(2-trifluoromethylsulfonyloxyphenyl)-2,3,4,5-tetrahydro-1H-benzo[d]azepine Hydrochloride: Use a method similar to the General Procedure 1-1, using 7-chloro-6-(2-trifluoromethylsulfonyloxyphenyl)-3-(2,2,2-trifluoroacetyl)-2,3,4,5-tetrahydro-1H-benzo[d]azepine (100 mg, 0.2 mmol) to obtain 7-chloro-6-(2-trifluoromethylsulfonyloxyphenyl)-2,3,4,5-tetrahydro-1H-benzo[d]azepine. Use a method similar to the General Procedure 2-2 to obtain the title compound (60 mg, 68% over 2 steps). MS (ES+) m/z: 406 (M+H)+.

EXAMPLE 7

7-Chloro-6-(4-phenyl-1H-pyrrol-3-yl)-2,3,4,5-tetrahydro-1H-benzo[d]azepine Succinate

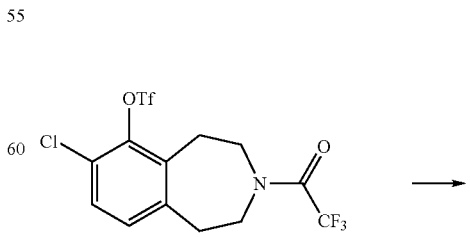

-continued

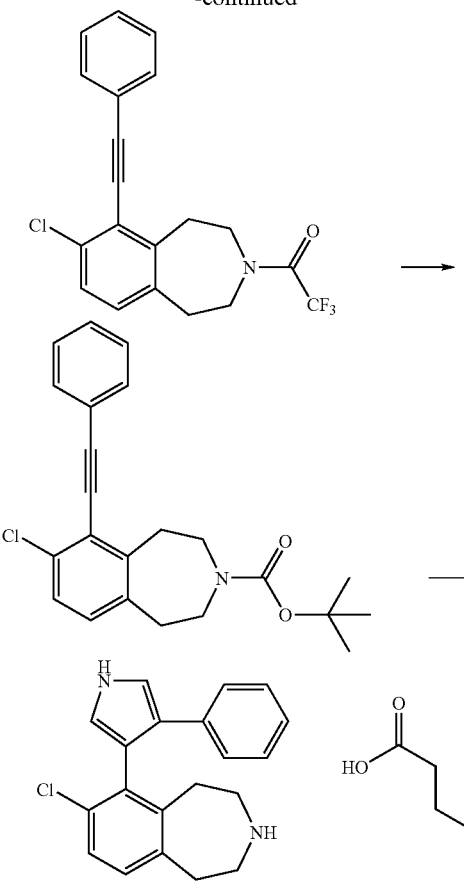

7-Chloro-6-phenethynyl-3-(2,2,2-trifluoroacetyl)-2,3,4,5-tetrahydro-1H-benzo[d]azepine: Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (1 g, 2.34 mmol) and phenylacetylene (0.51 mL, 4.68 mL) in anhydrous DMF (29 mL). Heat at 70° C. for 4 h. Purify the crude mixture by chromatography on silica gel eluting with hexane/EtOAc (1:0 to 3:2 gradient) to obtain the desired intermediate (0.81 g, 92%). Treat an aliquot with ammonia in methanol and record the mass spectrum. MS (ES+) m/z: 282 (M-TFA+H)+.

3-tert-Butoxycarbonyl-7-chloro-6-phenethynyl-2,3,4,5-tetrahydro-1H-benzo[d]azepine: Use a method similar to the General Procedure 1-1, using 7-chloro-6-phenethynyl-3-(2,2,2-trifluoroacetyl)-2,3,4,5-tetrahydro-1H-benzo[d]azepine (140 mg, 0.37 mmol) to obtain 7-chloro-6-phenethynyl-2,3,4,5-tetrahydro-1H-benzo[d]azepine as a yellow oil (124 mg). Dissolve 7-chloro-6-phenethynyl-2,3,4,5-tetrahydro-1H-benzo[d]azepine (124 mg, 0.37 mmol) in dichloromethane (5 mL), add di-tert-butyl-dicarbonate (0.1 g, 0.45 mmol) and stir for 1 h at room temperature. Remove the solvent and purify the crude mixture by chromatography on silica gel eluting with hexane/EtOAc (1:0 to 7:3 gradient) to obtain the desired intermediate as a yellow oil (130 mg, 92%).

7-Chloro-6-(4-phenyl-1H-pyrrol-3-yl)-2,3,4,5-tetrahydro-1H-benzo[d]azepine Succinate: Suspend trimethylamine-N-oxide (44 mg, 0.59 mmol) in anhydrous THF (7 mL) and add 3-tert-butoxycarbonyl-7-chloro-6-phenethynyl-2,3,4,5-tetrahydro-1H-benzo[d]azepine (150 mg, 0.39 mmol) in dichloromethane (3 mL). Cool the reaction mixture to 0° C., slowly add 1.5 M lithium diisopropylamide in THF and stir at 0° C. for 1 h. Warm the reaction mixture to room temperature, dilute with dichloromethane (20 mL) and wash with water (2×10 mL). Dry the organic layer over anhydrous Na₂SO₄, filter and concentrate in vacuo. Use a method similar to the General Procedure 1-4 to deprotect 3-tert-butoxycarbonyl-7-chloro-6-(4-phenyl-1H-pyrrol-3-yl)-2,3,4,5-tetrahydro-1H-benzo[d]azepine. Elute the crude mixture through a SCX column to obtain 7-chloro-6-(4-phenyl-1H-pyrrol-3-yl)-2,3,4,5-tetrahydro-1H-benzo[d]azepine as a yellow oil. Use a method similar to the General Procedure 2-1 to obtain the title compound as a white solid (40 mg, 30%). MS (ES+) m/z: 323 (M+H)+.

EXAMPLE 8

7-Chloro-6-(2-methyl-5-phenyl-2H-[1,2,3]triazol-4-yl)-2,3,4,5-tetrahydro-1H-benzo[d]azepine Hydrochloride

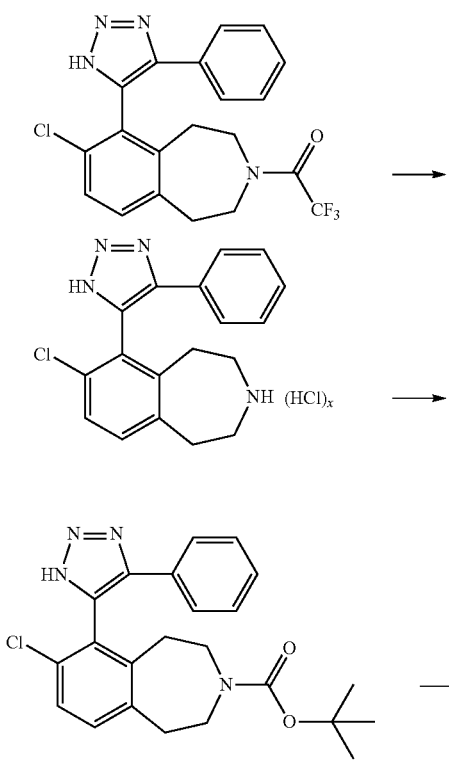

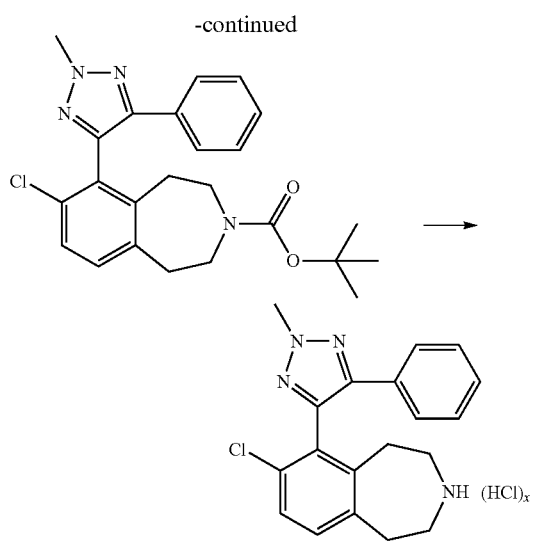

7-Chloro-6-(5-phenyl-3H-[1,2,3]triazol-4-yl)-3-(2,2,2-trifluoroacetyl)-2,3,4,5-tetrahydro-1H-benzo[d]azepine: Heat 7-chloro-6-phenylethynyl-3-(2,2,2-trifluoroacetyl)-2,3,4,5-tetrahydro-1H-benzo[d]azepine (100 mg, 0.26 mmol) and sodium azide (69 mg, 1.06 mmol) in anhydrous DMSO (5.3 mL) for 5.5 h. Cool the mixture, add brine and extract ten times with dichloromethane. Dry the combined organic extracts over Na$_2$SO$_4$, filter and evaporate onto silica gel. Purify by chromatography on silica gel eluting with hexane/EtOAc (1:0 to 2:3 gradient) to obtain the desired intermediate (43 mg, 39%). MS (ES+) m/z: 421 (M+H)$^+$.

7-Chloro-6-(5-phenyl-3H-[1,2,3]triazol-4-yl)-2,3,4,5-tetrahydro-1H-benzo[d]azepine hydrochloride: Stir 7-chloro-6-(5-phenyl-3H-[1,2,3]triazol-4-yl)-3-(2,2,2-trifluoroacetyl)-2,3,4,5-tetrahydro-1H-benzo[d]azepine (43 mg, 0.1 mmol) in 7M ammonia in methanol (10 mL) for 16 h. Concentrate the mixture in vacuo, and purify the residue by SCX chromatography. Use a method similar to the General Procedure 2-2 to obtain the desired intermediate (35 mg, 97%). MS (ES+) m/z: 325 (M+H)$^+$.

3-tert-Butoxycarbonyl-7-chloro-6-(5-phenyl-3H-[1,2,3]-triazol-4-yl)-2,3,4,5-tetrahydro-1H-benzo[d]azepine: Dissolve 7-chloro-6-(5-phenyl-3H-[1,2,3]triazol-4-yl)-2,3,4,5-tetrahydro-1H-benzo[d]azepine hydrochloride (27 mg, 0.07 mmol) in dichloromethane (2 mL) and saturated aqueous NaHCO$_3$ (2 mL). Add di-t-butyl-dicarbonate (33 mg, 0.15 mmol) and stir for 2 h at room temperature. Separate and dry the organic layer over Na$_2$SO$_4$, filter and concentrate in vacuo. Purify the crude mixture by chromatography on silica gel eluting with hexane/EtOAc (1:0 to 1:1 gradient) to obtain the desired intermediate (24 mg, 86%). MS (ES+) m/z: 425 (M+H)$^+$.

3-tert-Butoxycarbonyl-7-chloro-6-(2-methyl-5-phenyl-2H-[1,2,3]triazol-4-yl)-2,3,4,5-tetrahydro-1H-benzo[d]azepine: Dissolve 3-tert-butoxycarbonyl-7-chloro-6-(5-phenyl-3H-[1,2,3]triazol-4-yl)-2,3,4,5-tetrahydro-1H-benzo[d]azepine (24 mg, 0.06 mmol) in acetone (1.4 mL). Add potassium carbonate (41 mg, 0.3 mmol) and iodomethane (7.4 μL, 0.12 mmol) and stir for 16 h at room temperature. Filter the mixture through a fritted glass funnel and evaporate the filtrate. Purify the crude mixture by chromatography on silica gel to obtain the desired intermediate as the first of the three methylation isomers (7.8 mg, 25%).

7-Chloro-6-(2-methyl-5-phenyl-2H-[1,2,3]triazol-4-yl)-2,3,4,5-tetrahydro-1H-benzo[d]azepine Hydrochloride: Stir 3-tert-butoxycarbonyl-7-chloro-6-(2-methyl-5-phenyl-2H-[1,2,3]triazol-4-yl)-2,3,4,5-tetrahydro-1H-benzo[d]azepine (7.8 mg, 18 μmol) in trifluoroacetic acid (2 mL) at room temperature for 5 h. Concentrate in vacuo and purify the residue by HPLC (Zorbax SB-Phenyl column, 21.2×250 mm; flow rate: 22 mL/min; eluting with 10 to 90% acetonitrile in 0.1% aqueous trifluoroacetic acid). Concentrate in vacuo and elute the residue through a SCX column. Use a method similar to the General Procedure 2-2 and evaporate by lyophylization to obtain the title compound (6 mg, 100%). MS (ES+) m/z: 339 (M+H)$^+$.

EXAMPLE 9

7-Chloro-6-(5-methyl-thiophen-2-yl)-2,3,4,5-tetrahydro-1H-benzo[d]azepine Hydrochloride

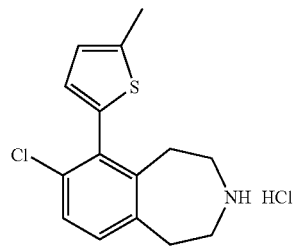 [SMILES: Cc1ccc(-c2c(Cl)ccc3c2CCNCC3)s1 ; Cl]

Add tetrakistriphenylphosphine palladium(0) (27 mg, 0.024 mmol), cesium fluoride (143 mg, 0.942 mmol) and 5-methyl-thiophen-2-yl-boronic acid (134 mg, 0.942 mmol) to a stirred solution of 7-chloro-3-(2,2,2-trifluoroacetyl)-6-trifluoromethanesulfonyloxy-2,3,4,5-tetrahydro-1H-benzo[d]azepine (200 mg, 0.471 mmol) in anhydrous DME (8 mL) at room temperature. Heat at 90° C. overnight. Cool the reaction mixture to room temperature, dilute with EtOAc and wash with water. Extract the aqueous phase twice with EtOAc. Dry the combined organic extracts over Na$_2$SO$_4$, filter and concentrate in vacuo. Purify the crude mixture by chromatography on silica gel eluting with hexane/EtOAc (1:0 and 19:1) to obtain 7-chloro-6-(5-methyl-thiophen-2-yl)-3-(2,2,2-trifluoroacetyl)-2,3,4,5-tetrahydro-1H-benzo[d]azepine (124 mg, 70%).

Use a method similar to the General Procedure 1-2, using 7-chloro-6-(5-methyl-thiophen-2-yl)-3-(2,2,2-trifluoroacetyl)-2,3,4,5-tetrahydro-1H-benzo[d]azepine (100 mg, 0.268 mmol) to obtain 7-chloro-6-(5-methyl-thiophen-2-yl)-2,3,4,5-tetrahydro-1H-benzo[d]azepine as an oil (74 mg, 100%) that was used without further purification. Use a method similar to the General Procedure 2-2 to obtain the title compound as a solid (70 mg, 83%). MS (ES+) m/z: 278 (M+H)$^+$.

EXAMPLES 10-11

Examples 10-11 may be prepared essentially as described in Example 9 by using 7-chloro-3-(2,2,2-trifluoroacetyl)-6-trifluoromethanesulfonyloxy-2,3,4,5-tetrahydro-1H-benzo[d]azepine and the appropriately substituted thiophen-2-yl-boronic acid. Overall yields and MS (ES+) data are shown in the Table below.

| Ex. | Structure | Compound | Yield (%) | MS (ES+) m/z |
|---|---|---|---|---|
| 10 | 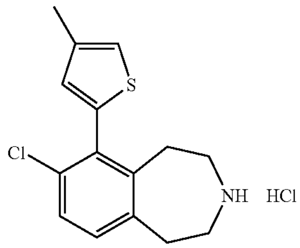 [SMILES: Cc1csc(-c2c(Cl)ccc3c2CCNCC3)c1 ; Cl] | 7-Chloro-6-(4-methyl-thiophen-2-yl)-2,3,4,5-tetrahydro-1H-benzo[d]azepine Hydrochloride | 78 | 278 (M + H)+ |
| 11 | 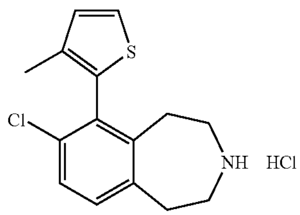 [SMILES: Cc1ccsc1-c1c(Cl)ccc2c1CCNCC2 ; Cl] | 7-Chloro-6-(3-methyl-thiophen-2-yl)-2,3,4,5-tetrahydro-1H-benzo[d]azepine Hydrochloride | 14 | 278 (M + H)+ |

EXAMPLE 12

7-Chloro-6-pyridin-3-ylmethyl-2,3,4,5-tetrahydro-1H-benzo[d]azepine Succinate

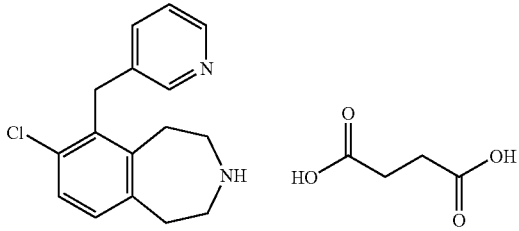 [SMILES: Clc1ccc2c(c1Cc1cccnc1)CCNCC2 ; O=C(O)CCC(=O)O]

Combine 6-bromomethyl-3-tert-butoxycarbonyl-7-chloro-2,3,4,5-tetrahydro-1H-benzo[d]azepine (700 mg, 1.89 mmol), pyridine-3-boronic acid (273 mg, 2.22 mmol), tetrakis(triphenylphospine)palladium(0) (1.1 g, 0.95 mmol), and sodium carbonate (600 mg, 5.66 mmol) in a mixture of toluene (14 mL), ethanol (3.5 mL) and water (0.7 mL). Heat the mixture to 60° C. for 12 h under nitrogen. Cool the reaction and concentrate in vacuo. Purify by chromatography on silica gel eluting with hexane and hexane/EtOAc (10:1, 5:1 and 1:1) to obtain 3-tert-butoxycarbonyl-7-chloro-6-pyridin-3-ylmethyl-2,3,4,5-tetrahydro-1H-benzo[d]azepine as an off-white solid (410 mg, 59%).

Use a method similar to the General Procedure 1-3 to deprotect 3-tert-butoxycarbonyl-7-chloro-6-pyridin-3-ylmethyl-2,3,4,5-tetrahydro-1H-benzo[d]azepine (410 mg, 1.1 mmol). Elute the crude mixture through a SCX column to obtain 7-chloro-6-pyridin-3-ylmethyl-2,3,4,5-tetrahydro-1H-benzo[d]azepine (265 mg, 88%). Use a method similar to the General Procedure 2-1 to obtain the title compound as a white solid (350 mg, 65%). MS (ES+) m/z: 273 (M+H)+.

EXAMPLE 13

7-Chloro-6-(2-pyridin-2-yl-ethyl)-2,3,4,5-tetrahydro-1H-benzo[d]azepine Succinate

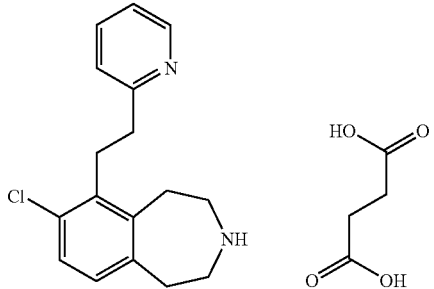 [SMILES: Clc1ccc2c(c1CCc1ccccn1)CCNCC2 ; O=C(O)CCC(=O)O]

Use a method similar to the General Procedure 1-2 to deprotect 7-chloro-6-(2-pyridin-2-yl-ethyl)-3-(2,2,2-trifluoroacetyl)-2,3,4,5-tetrahydro-1H-benzo[d]azepine (103 mg, 0.27 mmol). Purify by SCX chromatography then UV-guided reverse phase HPLC [Supelco Discovery C18 column, 21.2× 100 mm, 5 μm packing; flow rate: 20 mL/min; eluting with water/acetonitrile/acetic acid gradient over 15 min, fraction collection triggered using UV detector (220 and 254 nm)] to obtain 7-chloro-6-(2-pyridin-2-yl-ethyl)-2,3,4,5-tetrahydro-1H-benzo[d]azepine (56 mg, 72%). MS (ES+) m/z: 287 (M+H)+. Use a method similar to the General Procedure 2-1 to obtain the title compound as a white solid (81 mg, 100%). MS (ES+) m/z: 287 (M+H)+.

EXAMPLES 14-17

Examples 14-17 may be prepared essentially as described in Example 13. Purify by SCX chromatography and/or UV-guided reverse phase HPLC [Supelco Discovery C18 column, 21.2×100 mm, 5 μm packing; flow rate: 20 mL/min; eluting with water/acetonitrile/acetic acid gradient over 15 min, fraction collection triggered using UV detector (220 and 254 nm)]. Overall yields and MS (ES+) data are shown in the Table below.

| Ex. | Structure | Compound | Yield (%) | MS (ES+) m/z |
|---|---|---|---|---|
| 14 | 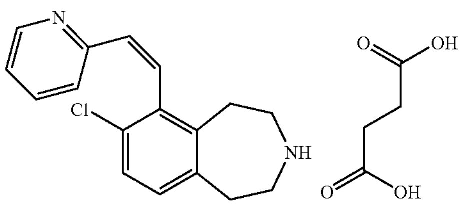 | 7-Chloro-6-(2-pyridin-2-yl-vinyl)-2,3,4,5-tetrahydro-1H-benzo[d]azepine Succinate | 26 | 285 (M + H)⁺ |
| 15 | 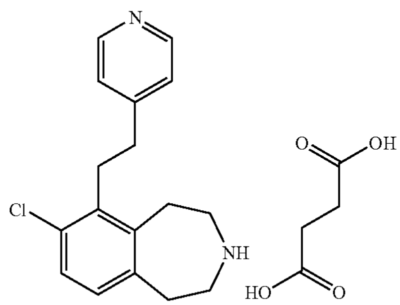 | 7-Chloro-6-(2-pyridin-4-yl-ethyl)-2,3,4,5-tetrahydro-1H-benzo[d]azepine Succinate | 68 | 287 (M + H)⁺ |
| 16 | 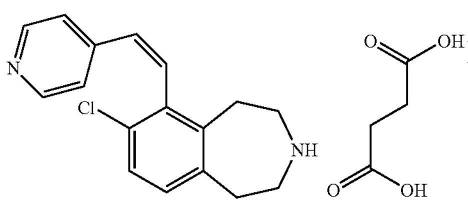 | 7-Chloro-6-(2-pyridin-4-yl-vinyl)-2,3,4,5-tetrahydro-1H-benzo[d]azepine Succinate | 73 | 285 (M + H)⁺ |
| 17 | 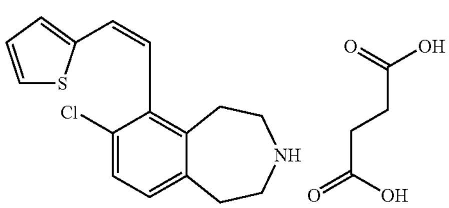 | 7-Chloro-6-(2-thiophen-2-yl-vinyl)-2,3,4,5-tetrahydro-1H-benzo[d]azepine Succinate | 38 | 290 (M + H)⁺ |

EXAMPLE 18

7-Chloro-6-(2-pyridin-3-yl-ethyl)-2,3,4,5-tetrahydro-1H-benzo[d]azepine Succinate

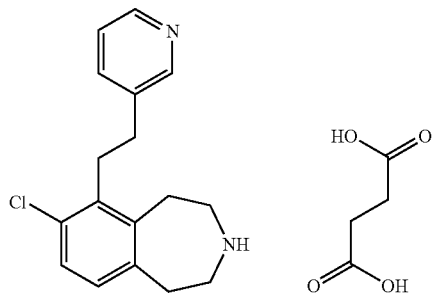 [SMILES: Clc1ccc2c(c1CCc1cccnc1)CCNCC2 ; O=C(O)CCC(=O)O]

Use a method similar to the General Procedure 2-1, using 7-chloro-6-(2-pyridin-3-yl-ethyl)-2,3,4,5-tetrahydro-1H-benzo[d]azepine, to obtain the title compound as a white solid (70 mg, 100%). MS (ES+) m/z: 287 (M+H)⁺.

EXAMPLE 19

Example 19 may be prepared essentially as described in Example 18 by using 7-chloro-6-(2-pyridin-3-yl-vinyl)-2,3,4,5-tetrahydro-1H-benzo[d]azepine. Overall yield and MS (ES+) data are shown in the Table below.

| Ex. | Structure | Compound | Yield (%) | MS (ES+) m/z |
|---|---|---|---|---|
| 19 | 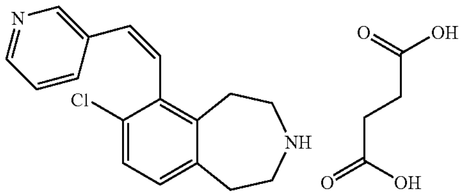 | 7-Chloro-6-(2-pyridin-3-yl-vinyl)-2,3,4,5-tetrahydro-1H-benzo[d]azepine Succinate | 91 | 285 (M + H)+ |

EXAMPLE 20

7-Chloro-6-[2-(2,4-difluorophenyl)-vinyl]-2,3,4,5-tetrahydro-1H-benzo[d]azepine (L)-Tartrate

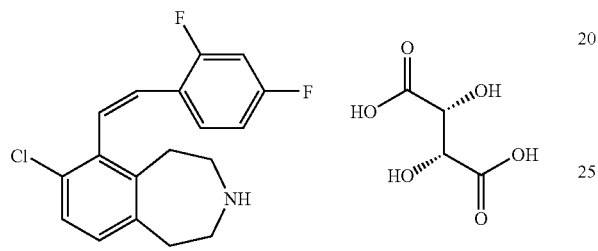

Use a method similar to the General Procedure 1-1 to deprotect 7-chloro-6-[2-(2,4-difluorophenyl)-vinyl]-3-(2,2,2-trifluoroacetyl)-2,3,4,5-tetrahydro-1H-benzo[d]azepine. Use a method similar to the General Procedure 2-3 to obtain the title compound as a solid (104 mg, 77% overall yield). MS (ES+) m/z: 320 (M+H)+.

EXAMPLES 21-23

Examples 21-23 may be prepared essentially as described in Example 20. Overall yields and MS (ES+) data are shown in the Table below.

| Ex. | Structure | Compound | Yield (%) | MS (ES+) m/z |
|---|---|---|---|---|
| 21 | 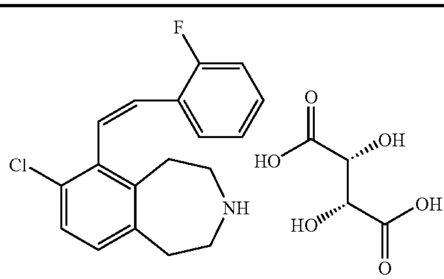 | 7-Chloro-6-[2-(2-fluorophenyl)-vinyl]-2,3,4,5-tetrahydro-1H-benzo[d]azepine (L)-Tartrate | 88 | 302 (M + H)+ |
| 22 | 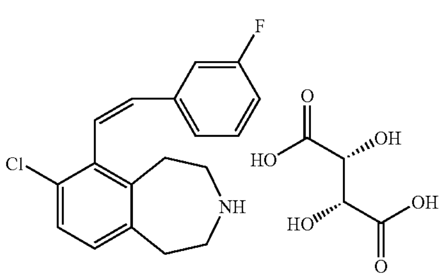 | 7-Chloro-6-[2-(3-fluorophenyl)-vinyl]-2,3,4,5-tetrahydro-1H-benzo[d]azepine (L)-Tartrate | 100 | 302 (M + H)+ |

-continued

| Ex. | Structure | Compound | Yield (%) | MS (ES+) m/z |
|---|---|---|---|---|
| 23 | 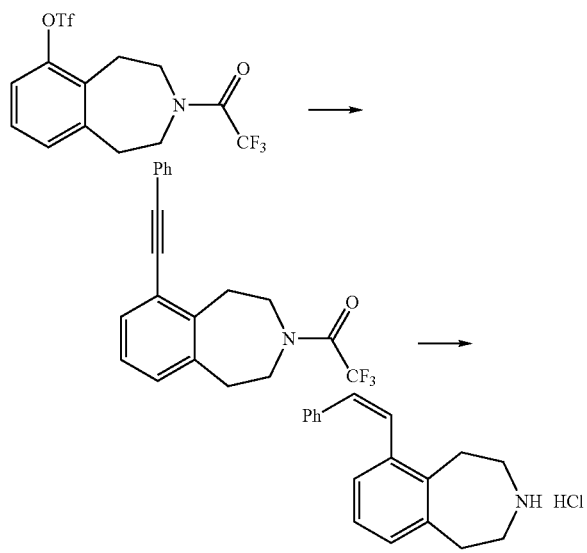 | 7-Chloro-6-[2-(3-fluorophenyl)-ethyl]-2,3,4,5-tetrahydro-1H-benzo[d]azepine (L)-Tartrate | 78 | 304 (M + H)+ |

EXAMPLE 24

(Z)-6-(2-Phenyl-vinyl)-2,3,4,5-tetrahydro-1H-benzo[d]azepine Hydrochloride

6-Phenylethynyl-3-(2,2,2-trifluoroacetyl)-2,3,4,5-tetrahydro-1H-benzo[d]azepine: Combine 3-(2,2,2-trifluoroacetyl)-6-trifluoromethanesulfonyloxy-2,3,4,5-tetrahydro-1H-benzo[d]azepine (300 mg, 0.75 mmol), dichlorobis(triphenylphosphine)-palladium(II) dichloromethane adduct (54 mg, 0.08 mmol), copper iodide (42 mg, 0.23 mmol) and tetrabutyl ammonium iodide (830 mg, 2.25 mmol) in DMF (3.3 mL) containing triethylamine (0.67 mL) and stir the mixture for 5 min at room temperature. Add phenylacetylene (0.17 mL, 1.5 mmol) and heat the mixture to 70° C. under nitrogen atmosphere for 16 h. Cool the reaction to room temperature and dilute with EtOAc/hexane (1:1, 250 mL). Filter the slurry through Celite®. Wash the filtrate with water (2×300 mL), dry the organic phase over Na₂SO₄, filter and concentrate in vacuo. Purify by chromatography on silica gel eluting with hexane/EtOAc (19:1 to 9:1) to afford 6-phenylethynyl-3-(2,2,2-trifluoroacetyl)-2,3,4,5-tetrahydro-1H-benzo[d]azepine (251 mg, 98%) as a yellow oil.

(Z)-6-(2-Phenyl-vinyl)-2,3,4,5-tetrahydro-1H-benzo[d]azepine Hydrochloride: Add a solution of 6-phenylethynyl-3-(2,2,2-trifluoroacetyl)-2,3,4,5-tetrahydro-1H-benzo[d]azepine (104 mg, 0.30 mmol) in EtOAc (10 mL) to a to a slurry of Lindlar's catalyst (50 mg) in EtOAc (10 mL). Pressurize to 35 psi of hydrogen and stir at room temperature for 1 h. Filter and concentrate in vacuo. Dissolve the crude residue (108 mg) in methanol (15 mL). Add 5N aqueous NaOH (5 mL) and stir the reaction at room temperature for 2 h. Concentrate the reaction mixture in vacuo and extract the aqueous phase with EtOAc (2×100 mL). Dry the organic layer over Na₂SO₄, filter and concentrate in vacuo. Purify by chromatography on silica gel eluting with DCM/2M ammonia in methanol (1:0 to 19:1 gradient) and concentrate in vacuo. Dissolve the residue in DCM and add an excess of 2M hydrogen chloride in diethyl ether. Concentrate in vacuo and dry the residue under vacuum to isolate the title compound as a tan glass (47 mg, 55%). MS (ES+) m/z: 249.9 (M+H)+.

EXAMPLE 25

7-Chloro-6-(2-thiazol-2-yl-ethyl)-2,3,4,5-tetrahydro-1H-benzo[d]azepine (L)-Tartrate

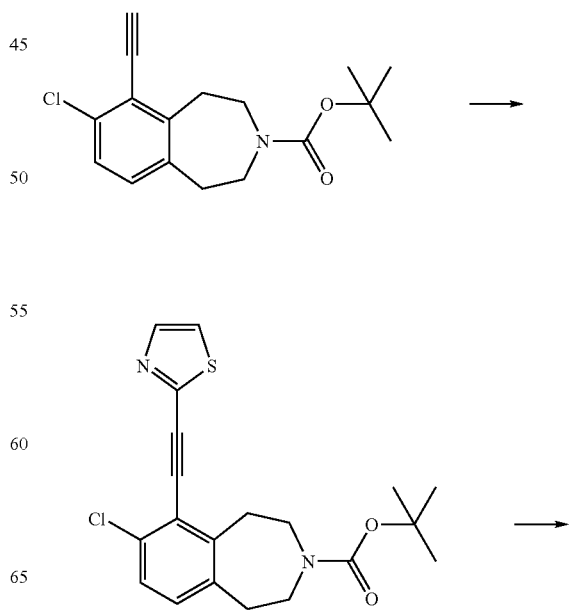

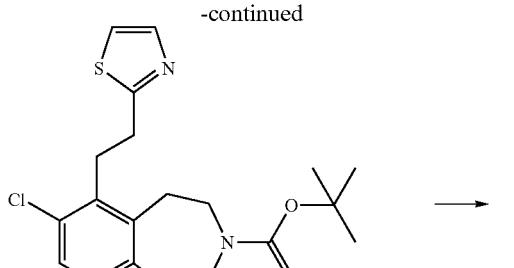

3-tert-Butoxycarbonyl-7-chloro-6-(thiazol-2-ylethnyl)-2,3,4,5-tetrahydro-1H-benzo[d]azepine: Dissolve 2-bromothiazole (0.09 mL, 0.96 mmol) in isopropylamine (10 mL) at room temperature, under nitrogen, then add bis(benzonitrile)palladium(II) chloride (37 mg, 0.096 mmol), triphenylphoshine (50 mg, 0.19 mmol) and copper(I) iodide (18 mg, 0.096 mmol). Degas the solution and purge with nitrogen, then add 3-tert-butoxycarbonyl-7-chloro-6-ethynyl-2,3,4,5-tetrahydro-1H-benzo[d]azepine (148 mg, 0.48 mmol). Seal the reaction vessel, stir at room temperature for 30 min, then at 75° C. for 4 h. Concentrate in vacuo, dissolve the residue with diethyl ether and wash with 2M aqueous HCl. Dry the organic layer over $MgSO_4$, filter and concentrate in vacuo. Purify the crude mixture by chromatography on silica gel eluting with isohexane/EtOAc (1:0 to 4:1 gradient over 30 min) to obtain the desired intermediate (165 mg, 89%). MS (ES+) m/z: 389 $(M+H)^+$.

3-tert-Butoxycarbonyl-7-chloro-6-(2-thiazol-2-yl-ethyl)-2,3,4,5-tetrahydro-1H-benzo[d]azepine: Add a solution of 3-tert-butoxycarbonyl-7-chloro-6-(thiazol-2-ylethynyl)-2,3,4,5-tetrahydro-1H-benzo[d]azepine (160 mg, 0.41 mmol) in ethanol (10 mL) to a suspension of 10% Pd/C (Degussa type E101, 160 mg), then acetic acid (0.5 mL). Hydrogenate for 7 h (68-70 psi) then filter the catalyst through Celite® and concentrate in vacuo. Purify by chromatography on silica gel eluting with isohexane/EtOAc (1:0 to 4:1 gradient over 40 min) to obtain the desired intermediate (16 mg, 10%). MS (ES+) m/z: 393 $(M+H)^+$.

7-Chloro-6-(2-thiazol-2-yl-ethyl)-2,3,4,5-tetrahydro-1H-benzo[d]azepine (L)-Tartrate: Use a method similar to the General Procedure 1-4 to deprotect 3-tert-butoxycarbonyl-7-chloro-6-(2-thiazol-2-yl-ethyl)-2,3,4,5-tetrahydro-1H-benzo[d]azepine (14 mg, 0.036 mmol). Purify by SCX chromatography to obtain 7-chloro-6-(2-thiazol-2-yl-ethyl)-2,3,4,5-tetrahydro-1H-benzo[d]azepine. Use a method similar to the General Procedure 2-3 to obtain the title compound as a solid (14 mg, 88%). MS (ES+) m/z: 293 $(M+H)^+$.

EXAMPLE 26

7-Chloro-6-[3-(2,2-dimethyl-propionylamino)-prop-1-ynyl]-2,3,4,5-tetrahydro-1H-benzo[d]azepine (L)-Tartrate

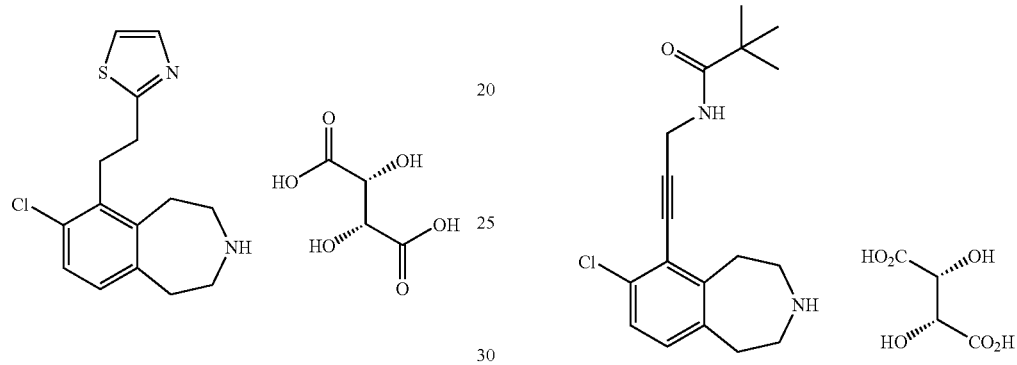

Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (212 mg, 0.5 mmol) and 2,2-dimethyl-N-prop-2-ynyl-propionamide (139 mg, 1 mmol) (prepared by following the procedure described in *Org. Lett.* 2004, 6, 3593) in DMF/triethylamine (5:1, 6 mL). Purify by chromatography on silica gel eluting with hexane/EtOAc (10:1 to 7:3 gradient) to obtain 7-chloro-6-[3-(2,2-dimethyl-propionylamino)-prop-1-ynyl]-3-(2,2,2-trifluoroacetyl)-2,3,4,5-tetrahydro-1H-benzo[d]azepine (120 mg, 58%).

Use a method similar to the General Procedure 1-2, using 7-chloro-6-[3-(2,2-dimethyl-propionylamino)-prop-1-ynyl]-3-(2,2,2-trifluoroacetyl)-2,3,4,5-tetrahydro-1H-benzo[d]azepine (120 mg, 0.29 mmol) to obtain 7-chloro-6-[3-(2,2-dimethyl-propionylamino)-prop-1-ynyl]-2,3,4,5-tetrahydro-1H-benzo[d]azepine. Use a method similar to the General Procedure 2-3 to obtain the title compound (75 mg, 55% over 2 steps). MS (ES+) m/z: 319 $(M+H)^+$.

EXAMPLES 27-30

Examples 27-30 may be prepared essentially as described in Example 26 by using 7-chloro-3-(2,2,2-trifluoroacetyl)-6-trifluoromethanesulfonyloxy-2,3,4,5-tetrahydro-1H-benzo[d]azepine and the appropriately substituted alkyne. Overall yields and MS (ES+) data are shown in the Table below.

| Ex. | Structure | Compound | Yield (%) | MS (ES+) m/z |
|---|---|---|---|---|
| 27 | 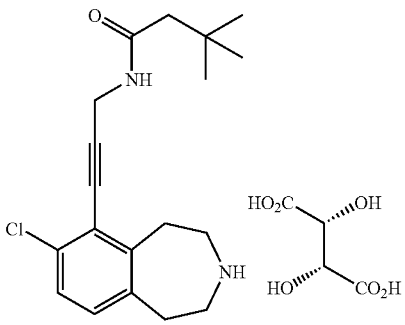 [SMILES: CC(C)(C)CC(=O)NCC#Cc1c(Cl)ccc2c1CCNCC2 ; O=C(O)[C@H](O)[C@@H](O)C(=O)O] | 7-Chloro-6-[3-(3,3-dimethyl-butyrylamino)-prop-1-ynyl]-2,3,4,5-tetrahydro-1H-benzo[d]azepine (L)-Tartrate | 61 | 333 (M + H)+ |
| 28 | 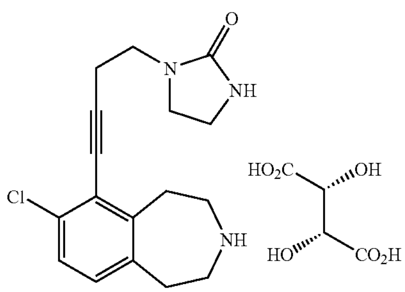 [SMILES: O=C1NCCN1CCC#Cc1c(Cl)ccc2c1CCNCC2 ; O=C(O)[C@H](O)[C@@H](O)C(=O)O] | 7-Chloro-6-[4-(2-oxo-imidazolidin-1-yl)-but-1-ynyl]-2,3,4,5-tetrahydro-1H-benzo[d]azepine (L)-Tartrate | 58 | 318 (M + H)+ |
| 29 | 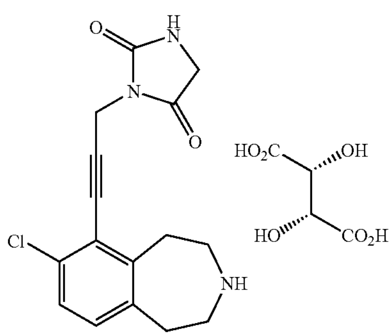 [SMILES: O=C1CNC(=O)N1CC#Cc1c(Cl)ccc2c1CCNCC2 ; O=C(O)[C@H](O)[C@@H](O)C(=O)O] | 7-Chloro-6-[3-(2,4-dioxo-imidazolidin-3-yl)-prop-1-ynyl]-2,3,4,5-tetrahydro-1H-benzo[d]azepine (L)-Tartrate | 39 | 318 (M + H)+ |
| 30 | 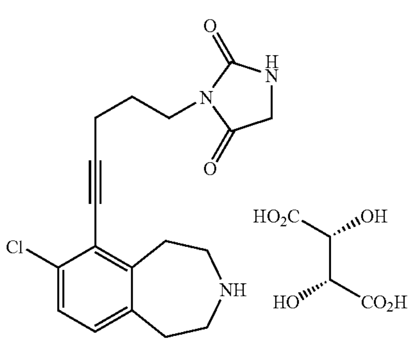 [SMILES: O=C1CNC(=O)N1CCCC#Cc1c(Cl)ccc2c1CCNCC2 ; O=C(O)[C@H](O)[C@@H](O)C(=O)O] | 7-Chloro-6-[5-(2,4-dioxo-imidazolidin-3-yl)-pent-1-ynyl]-2,3,4,5-tetrahydro-1H-benzo[d]azepine (L)-Tartrate | 34 | 346 (M + H)+ |

EXAMPLE 31

7-Chloro-6-[4-(2,2-dimethyl-propionylamino)-but-1-ynyl]-2,3,4,5-tetrahydro-1H-benzo[d]azepine

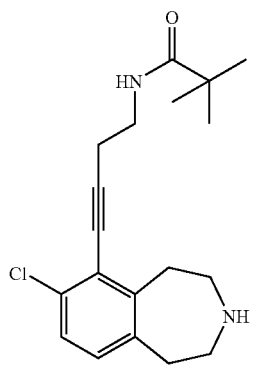 [SMILES: CC(C)(C)C(=O)NCCC#Cc1c(Cl)ccc2c1CCNCC2]

Use a method similar to the General Procedure 3 to couple 7-chloro-3-(2,2,2-trifluoroacetyl)-6-trifluoromethanesulfonyloxy-2,3,4,5-tetrahydro-1H-benzo[d]azepine (425 mg, 1 mmol) with N-but-3-ynyl-2,2-dimethyl-propionamide (306 mg, 2 mmol) in DMF (10 mL). Purify by chromatography on silica gel eluting with cyclohexane/EtOAc (85:15 to 0:100 gradient) to obtain 7-chloro-6-[4-(2,2-dimethyl-propionylamino)-but-1-ynyl]-3-(2,2,2-trifluoroacetyl)-2,3,4,5-tetrahydro-1H-benzo[d]azepine as an oil (437 mg, 99%).

Use a method similar to the General Procedure 1-1, using 7N ammonia in methanol/water/THF (10:1:1 ratio) as solvent, to deprotect 7-chloro-6-[4-(2,2-dimethyl-propionylamino)-but-1-ynyl]-3-(2,2,2-trifluoroacetyl)-2,3,4,5-tetrahydro-1H-benzo[d]azepine (62 mg, 0.14 mmol) and afford the title compound as an oil (44 mg, 91%). MS (ES+) m/z: 333.1 (M+H)$^+$.

EXAMPLES 32-37

Examples 32-37 may be prepared essentially as described in Example 31 by using 7-chloro-3-(2,2,2-trifluoroacetyl)-6-trifluoromethanesulfonyloxy-2,3,4,5-tetrahydro-1H-benzo[d]azepine and the appropriately substituted alkyne. Overall yields and MS (ES+) data are shown in the Table below. Example 32 was prepared as (L)-Tartrate by following essentially the procedure described in the General Procedure 2-3.

| Ex. | Structure | Compound | Yield (%) | MS (ES+) m/z |
|---|---|---|---|---|
| 32 | 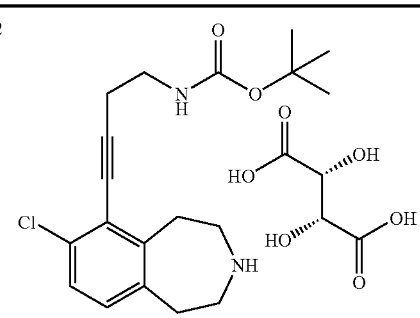 | 6-(4-tert-Butoxycarbonylamino-but-1-ynyl)-7-chloro-2,3,4,5-tetrahydro-1H-benzo[d]azepine (L)-Tartrate | 68 | 349 (M + H)$^+$ |
| 33 | 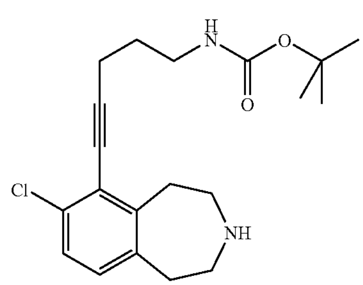 [SMILES: CC(C)(C)OC(=O)NCCCC#Cc1c(Cl)ccc2c1CCNCC2] | 6-(5-tert-Butoxycarbonylamino-pent-1-ynyl)-7-chloro-2,3,4,5-tetrahydro-1H-benzo[d]azepine | 41 | 363 (M + H)$^+$ |
| 34 | 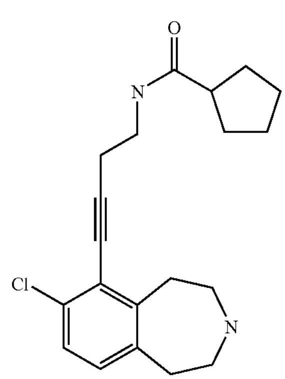 [SMILES: O=C(NCCC#Cc1c(Cl)ccc2c1CCNCC2)C1CCCC1] | 7-Chloro-6-[4-(cyclopentanecarbonyl-amino)-but-1-ynyl]-2,3,4,5-tetrahydro-1H-benzo[d]azepine | 98 | 345.1 (M + H)$^+$ |

-continued

| Ex. | Structure | Compound | Yield (%) | MS (ES+) m/z |
|---|---|---|---|---|
| 35 | 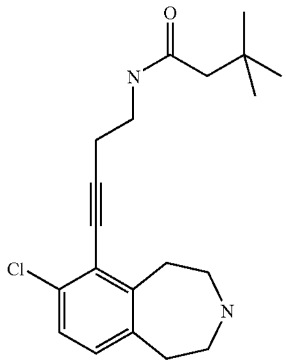 [SMILES: CC(C)(C)CC(=O)NCCC#Cc1c(Cl)ccc2c1CCNCC2] | 7-Chloro-6-[4-(3,3-dimethyl-butyrylamino-but-1-ynyl]-2,3,4,5-tetrahydro-1H-benzo[d]azepine | 49 | 347.1 (M + H)+ |
| 36 | 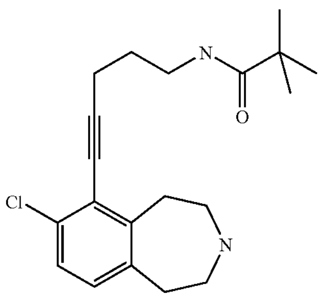 [SMILES: CC(C)(C)C(=O)NCCCC#Cc1c(Cl)ccc2c1CCNCC2] | 7-Chloro-6-[5-(2,2-dimethyl-propionylamino)-pent-1-ynyl]-2,3,4,5-tetrahydro-1H-benzo[d]azepine | 54 | 347.1 (M + H)+ |
| 37 | 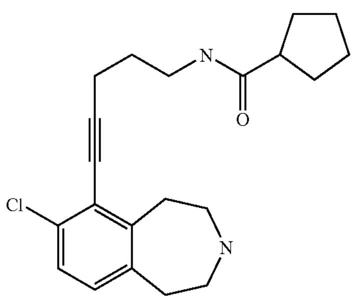 [SMILES: O=C(NCCCC#Cc1c(Cl)ccc2c1CCNCC2)C1CCCC1] | 7-Chloro-6-[5-(cyclopentanecarbonyl-amino)-pent-1-ynyl)-2,3,4,5-tetrahydro-1H-benzo[d]azepine | 41 | 359.1 (M + H)+ |

EXAMPLE 38

7-Chloro-6-[4-(2-oxo-imidazolidin-1-yl)-butyl]-2,3,4,5-tetrahydro-1H-benzo[d]azepine

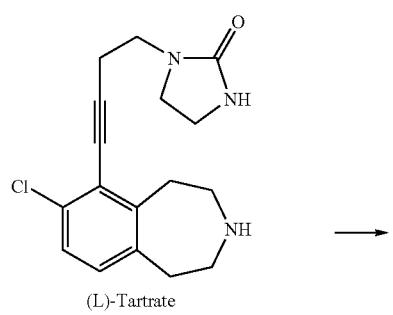

(L)-Tartrate

-continued

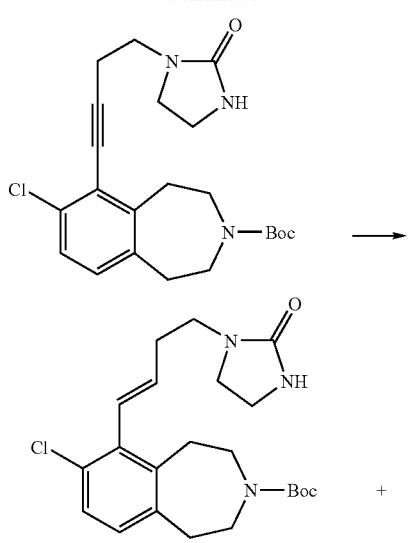

+

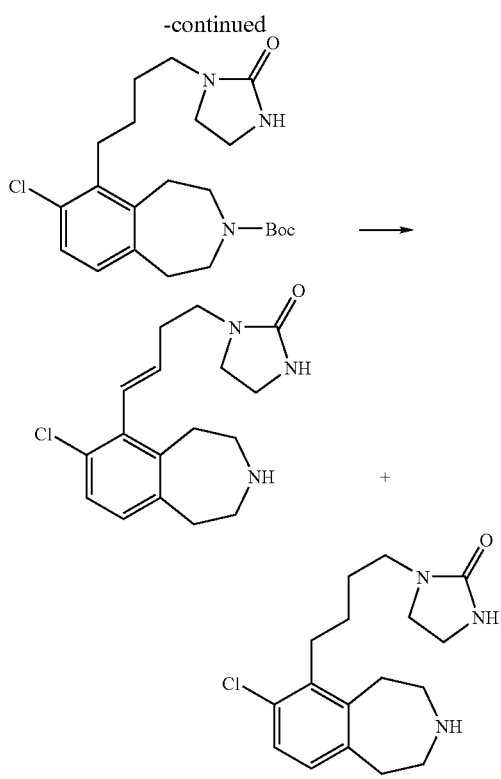

Filter a solution of 7-chloro-6-[4-(2-oxo-imidazolidin-1-yl)-but-1-ynyl]-2,3,4,5-tetrahydro-1H-benzo[d]azepine (L)-tartrate (33 mg, 0.07 mmol) in methanol (5 mL) through a SCX-2 cartridge (2 g), eluting with a solution of 7N ammonia in methanol (10 mL), to obtain the free base. Concentrate in vacuo, and dissolve the residue in anhydrous DCM. Add di-tert-butyl-dicarbonate (18 mg, 0.08 mmol) to this solution and stir at room temperature for 3 h. Add 7N ammonia in MeOH (5 mL), stir for further 1 h and concentrate in vacuo to obtain 3-tert-butoxycarbonyl-7-chloro-6-[4-(2-oxo-imidazolidin-1-yl)-but-1-ynyl]-2,3,4,5-tetrahydro-1H-benzo[d]azepine (23 mg) suitable for use without further purification.

Add a solution of 3-tert-butoxycarbonyl-7-chloro-6-[4-(2-oxo-imidazolidin-1-yl)-but-1-ynyl]-2,3,4,5-tetrahydro-1H-benzo[d]azepine (23 mg, 0.06 mmol) in EtOAc (10 mL) to a heterogeneous mixture of 10% Pd/C (Degussa type E101) in EtOAc (10 mL). Submit the mixture to hydrogenation under 15 psi hydrogen at room temperature for 30 min. Filtrate the reaction mixture over Celite®, rinse with EtOAc and concentrate in vacuo to give a yellow oil as a mixture of (Z)-3-tert-butoxycarbonyl-7-chloro-6-[4-(2-oxo-imidazolidin-1-yl)-but-1-enyl]-2,3,4,5-tetrahydro-1H-benzo[d]azepine and 3-tert-butoxycarbonyl-7-chloro-6-[4-(2-oxo-imidazolidin-1-yl)-butyl]-2,3,4,5-tetrahydro-1H-benzo[d]azepine.

Use the mixture as crude without further purification. Add a solution of TFA (5 mL) in DCM (10 mL) and stir at room temperature for 2 h. Concentrate in vacuo and purify the crude mixture by UV-guided HPLC (UV Flex) to obtain (Z)-7-chloro-6-[4-(2-oxo-imidazolidin-1-yl)-but-1-enyl]-2,3,4,5-tetrahydro-1H-benzo[d]azepine (19 mg) and 7-chloro-6-[4-(2-oxo-imidazolidin-1-yl)-butyl]-2,3,4,5-tetrahydro-1H-benzo[d]azepine [1.5 mg, MS (ES+) m/z: 322 (M+H)$^+$].

EXAMPLES 39-41

Examples 39-41 may be prepared essentially as described in Example 38 by using the appropriately substituted 6-(alk-1-ynyl)-2,3,4,5-tetrahydro-1H-benzo[d]azepine. Overall yields and MS (ES+) data are shown in the Table below.

| Ex. | Structure | Compound | Yield (%) | MS (ES+) m/z |
|---|---|---|---|---|
| 39 | 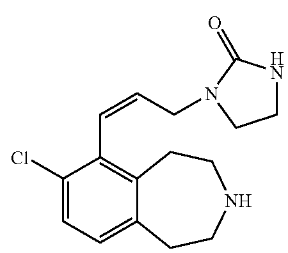 [SMILES: O=C1NCCN1C/C=C\c1c(Cl)ccc2c1CCNCC2] | (Z)-7-Chloro-6-[3-(2-oxo-imidazolidin-1-yl)-prop-1-enyl]-2,3,4,5-tetrahydro-1H-benzo[d]azepine | 76 | 306 (M + H)$^+$ |
| 40 | 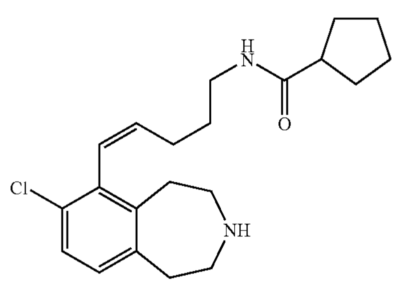 [SMILES: O=C(NCCC/C=C\c1c(Cl)ccc2c1CCNCC2)C1CCCC1] | 7-Chloro-6-[5-(cyclopentanecarbonyl-amino)-pent-1-enyl]-2,3,4,5-tetrahydro-1H-benzo[d]azepine | 82 | 361 (M + H)$^+$ |

| Ex. | Structure | Compound | Yield (%) | MS (ES+) m/z |
|---|---|---|---|---|
| 41 | 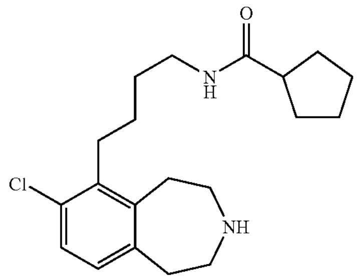 [SMILES: O=C(NCCCCc1c(Cl)ccc2c1CCNCC2)C1CCCC1] | 7-Chloro-6-[4-(cyclopentanecarbonyl-amino)-butyl]-2,3,4,5-tetrahydro-1H-benzo[d]azepine | 80 | 349 (M + H)+ |

EXAMPLE 42

7-Chloro-6-[5-(cyclopentanecarbonyl-amino)-pentyl]-2,3,4,5-tetrahydro-1H-benzo[d]azepine (L)-Tartrate

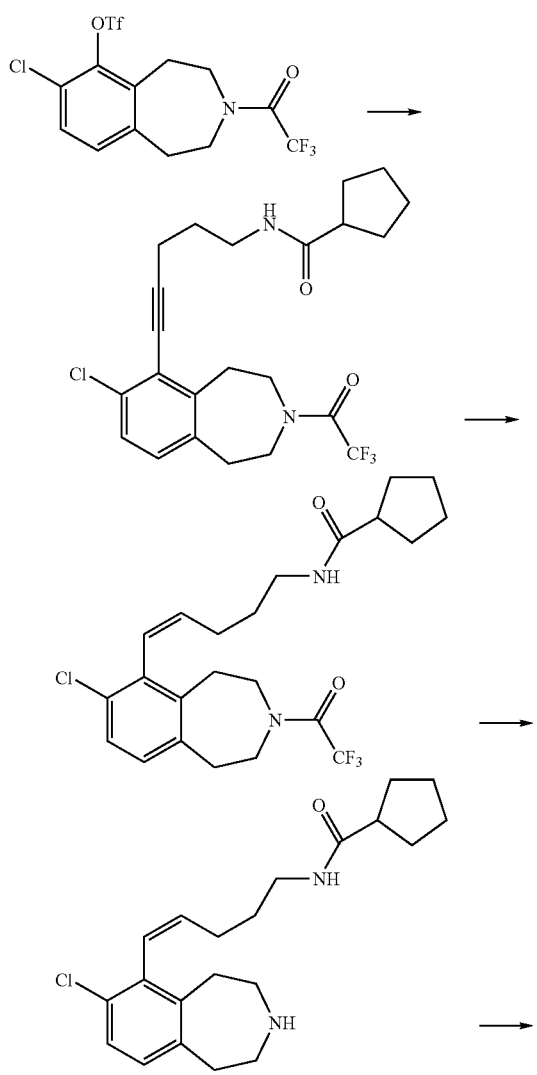

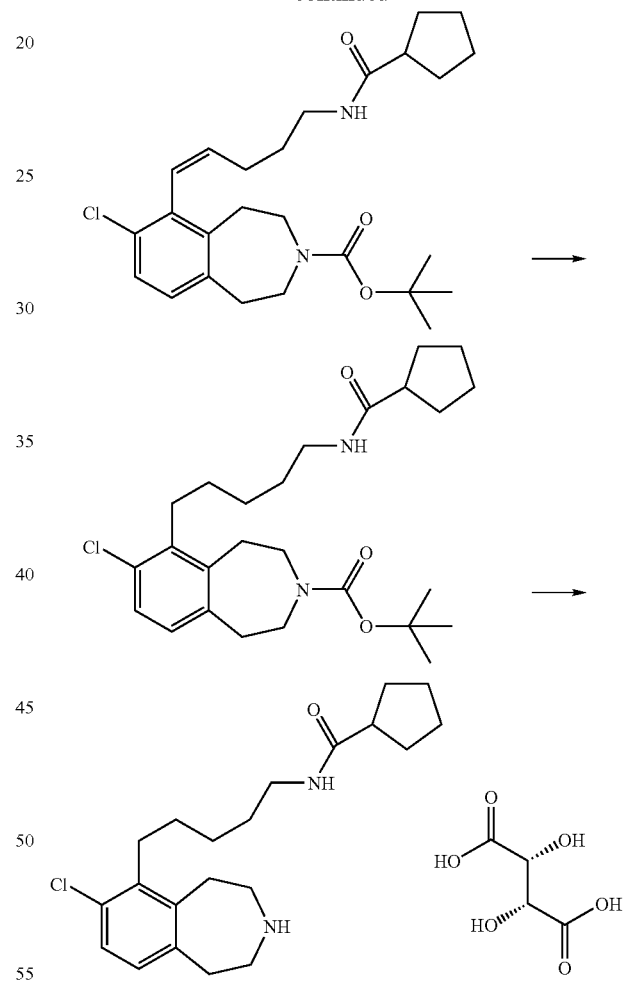

7-Chloro-6-[5-(cyclopentanecarbonyl-amino)-pent-1-ynyl]-3-(2,2,2-trifluoroacetyl)-2,3,4,5-tetrahydro-1H-benzo[d]azepine: In an oven dried flask degas DMF (20 mL) by gently bubbling nitrogen gas for 2 h. Add then 7-chloro-3-(2,2,2-trifluoroacetyl)-6-trifluoromethanesulfonyloxy-2,3,4,5-tetrahydro-1H-benzo[d]azepine (1.0 g, 2.35 mmoles), N-pent-4-ynyl-cyclopentylcarboxamide (842 mg, 4.7 mmoles), copper iodide (134 mg, 0.705 mmoles), triethylamine (4.7 mL), tetra-n-butylammonium iodide (2.6 g, 7.05 mmoles) and bis(triphenylphosphine)palladium(II) chloride (165 mg, 0.235 mmoles) and heat the resulting mixture at 80° C. under nitrogen atmosphere while stirring overnight. Concentrate the mixture in vacuo, and then filter through a short pad of Celite® eluting with EtOAc. Purify the residue by chromatography on silica gel eluting with dichloromethane/EtOAc/cyclohexane (3:5:1) to obtain the desired intermediate as an oil (726 mg, 68%). MS (ES+) m/z=455.1 (M+H)$^+$.

7-Chloro-6-[5-(cyclopentanecarbonyl-amino)-pent-1-enyl]-3-(2,2,2-trifluoroacetyl)-2,3,4,5-tetrahydro-1H-benzo[d]azepine: Dissolve 7-chloro-6-[5-(cyclopentanecarbonyl-amino)-pent-1-ynyl]-3-(2,2,2-trifluoroacetyl)-2,3,4,5-tetrahydro-1H-benzo[d]azepine (726 mg) in EtOAc (20 mL). Add 10% Pd/C (Degussa type, 100 mg) and then stir the mixture under 15 psi of hydrogen for 10 min. As reaction is not completed, add extra catalyst (147 mg) and stir under 15 psi of hydrogen for an extra 15 min. Filter the reaction mixture through a short pad of Celite® and concentrate in vacuo to obtain the desired intermediate that was used in the next step without further purification. MS (ES+) m/z=457.2 (M+H)$^+$.

7-Chloro-6-[5-(cyclopentanecarbonol-amino)-pent-1-enyl]-2,3,4,5-tetrahydro-1H-benzo[d]azepine: Dissolve the crude material obtained in the previous step in 7N ammonia in methanol (40 mL) and then add water (15 mL) and THF (15 mL) and stir overnight at room temperature. Concentrate in vacuo and then purify the residue via preparative HPLC to obtain the desired intermediate as an oil (246 mg, 43% for the last two steps). MS (ES+) m/z=361.2 (M+H)$^+$.

3-tert-Butoxycarbonyl-7-chloro-6-[5-(cyclopentanecarbonyl-amino)-pent-1-enyl]-2,3,4,5-tetrahydro-1H-benzo[d]azepine: Dissolve 7-chloro-6-[5-(cyclopentanecarbonyl-amino)-pent-1-enyl]-2,3,4,5-tetrahydro-1H-benzo[d]azepine (279 mg, 0.77 mmoles) in dichloromethane (5 mL) and then add di-tert-butyl-dicarbonate (168 mg, 0.77 mmoles). Stir at room temperature overnight and then concentrate in vacuo to obtain the desired intermediate that was suitable for use without further purification. MS (ES+) m/z=483.2 (M+Na)$^+$.

3-tert-Butoxycarbonyl-7-chloro-6-[5-(cyclopentanecarbonyl-amino)-pentyl]-2,3,4,5-tetrahydro-1H-benzo[d]azepine: Dissolve 3-tert-butoxycarbonyl-7-chloro-6-[5-(cyclopentanecarbonyl-amino)-pent-1-enyl]-2,3,4,5-tetrahydro-1H-benzo[d]azepine as obtained in the previous step in EtOAc (20 mL) and add 10% Pd/C (Degussa type, 200 mg). Then apply a pressure of 70 psi of hydrogen while shaken vigorously. Filter the crude mixture through a short pad of Celite® and concentrate in vacuo. Purify the resulting material by preparative HPLC to obtain the desired intermediate as a clear oil (311 mg, 87% for the two previous steps). MS (ES+) m/z=485.2 (M+Na)$^+$.

7-Chloro-6-[5-(cyclopentanecarbonyl-amino)-pentyl]-2,3,4,5-tetrahydro-1H-benzo[d]azepine (L)-Tartrate: Dissolve 3-tert-butoxycarbonyl-7-chloro-6-[5-(cyclopentanecarbonyl-amino)-pentyl]-2,3,4,5-tetrahydro-1H-benzo[d]azepine (311 mg, 0.67 mmoles) in dichloromethane (10 mL) and add trifluoroacetic acid (3 mL). Stir the reaction for 1 h. Concentrate in vacuo and purify the residue by preparative HPLC to give 7-chloro-6-[5-(cyclopentanecarbonyl-amino)-pentyl]-2,3,4,5-tetrahydro-1H-benzo[d]azepine (135 mg) as an oil. Dissolve the oil in methanol (5 mL) and add (L)-tartaric acid (56 mg, 0.37 mmoles). Concentrate the mixture in vacuo and then add water (5 mL). The resulting solution is then freeze dried overnight to yield the title compound as a white solid (184 mg, 55%). MS (ES+) m/z=363.2 (M+H)$^+$.

EXAMPLE 43

7-Chloro-6-[3-(cyclopentanecarbonyl-amino)-prop-1-ynyl]-2,3,4,5-tetrahydro-1H-benzo[d]azepine (L)-Tartrate

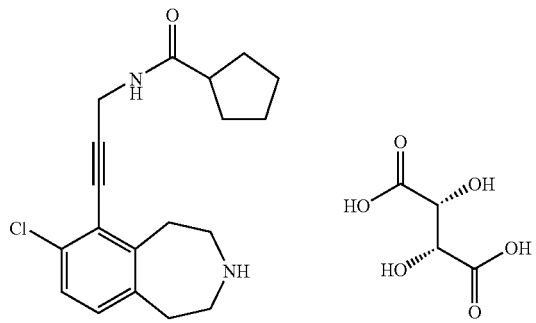 [SMILES: O=C(NCC#Cc1c(Cl)ccc2c1CCNCC2)C1CCCC1 ; O=C(O)[C@H](O)[C@@H](O)C(=O)O]

Dissolve 7-chloro-3-(2,2,2-trifluoroacetyl)-6-trifluoromethanesulfonyloxy-2,3,4,5-tetrahydro-1H-benzo[d]azepine (1 g, 2.35 mmol), tris(dibenzylideneacetone)-dipalladium(0) (0.03 equiv.), copper(I) iodide (0.06 equiv.) and triphenylphosphine (0.25 equiv.) in triethylamine/DMF (3:1, 4 mL). Stir the mixture for 5 min at ambient temperature, add N-prop-2-ynyl-cyclopentylcarboxamide (430 mg, 2.82 mmol) and heat at 70° C. for 18 h in a sealed tube. Cool the reaction mixture to ambient temperature, dilute with EtOAc/hexane (1:1) and wash with water. Dry the organic fraction over MgSO$_4$, filter and concentrate in vacuo. Purify by chromatography on silica gel eluting with hexane/EtOAc (10:1 to 7:3) to obtain 7-chloro-6-[3-(cyclopentanecarbonyl-amino)-prop-1-ynyl]-3-(2,2,2-trifluoroacetyl)-2,3,4,5-tetrahydro-1H-benzo[d]azepine (500 g, 50%).

Use a method similar to the General Procedure 1-2 using 7-chloro-6-[3-(cyclopentanecarbonyl-amino)-prop-1-ynyl]-3-(2,2,2-trifluoroacetyl)-2,3,4,5-tetrahydro-1H-benzo[d]azepine (167 mg, 0.39 mmol) to give 7-chloro-6-[3-(cyclopentanecarbonyl-amino)-prop-1-ynyl]-2,3,4,5-tetrahydro-1H-benzo[d]azepine. Use a method similar to the General Procedure 2-3 to give the title compound (145 mg, 78%). MS (ES+) m/z: 331 (M+H)$^+$.

EXAMPLE 44

7-Chloro-6-[(Z)-3-(cyclopentanecarbonyl-amino)-propenyl]-2,3,4,5-tetrahydro-1H-benzo[d]azepine (L)-Tartrate

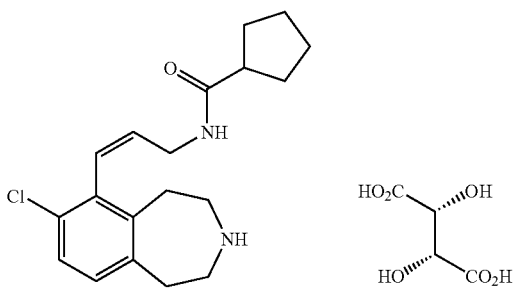 [SMILES: O=C(NC/C=C\c1c(Cl)ccc2c1CCNCC2)C1CCCC1 ; O=C(O)[C@H](O)[C@@H](O)C(=O)O]

Dissolve 7-chloro-6-[3-(cyclopentanecarbonyl-amino)-prop-1-ynyl]-3-(2,2,2-trifluoroacetyl)-2,3,4,5-tetrahydro- 1H-benzo[d]azepine (170 mg, 0.4 mmol) in EtOAc (50 mL) and submit the mixture to hydrogenation over 10% Pd/C (85 mg) at 15 psi for 10 mins. Filter the mixture through Celite® and concentrate the filtrate to give 7-chloro-6-[(Z)-3-(cyclopentanecarbonyl-amino)-propenyl]-3-(2,2,2-trifluoroacetyl)-2,3,4,5-tetrahydro-1H-benzo[d]azepine as a pale yellow solid (170 mg).

Use a method similar to the General Procedure 1-2 using 7-chloro-6-[(Z)-3-(cyclopentanecarbonyl-amino)-propenyl]-3-(2,2,2-trifluoroacetyl)-2,3,4,5-tetrahydro-1H-benzo[d]azepine (170 mg, 0.39 mmol) to give 7-chloro-6-[(Z)-3-(cyclopentanecarbonyl-amino)-propenyl]-2,3,4,5-tetrahydro-1H-benzo[d]azepine. Use a method similar to the General Procedure 2-3 to give the title compound (93 mg, 70%). MS (ES+) m/z: 333 (M+H)+.

EXAMPLE 45

7-Chloro-6-{4-[(cyclopentanecarbonyl-amino)-methyl]-phenyl}-2,3,4,5-tetrahydro-1H-benzo[d]azepine (L)-Tartrate

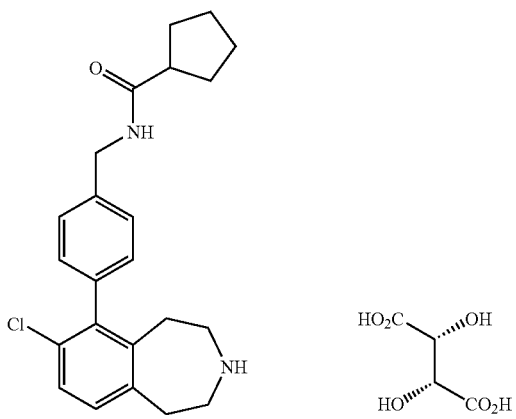 [SMILES: O=C(NCc1ccc(-c2c(Cl)ccc3c2CCNCC3)cc1)C1CCCC1 ; O=C(O)[C@H](O)[C@@H](O)C(=O)O]

Dissolve 7-chloro-3-(2,2,2-trifluoroacetyl)-6-trifluoromethanesulfonyloxy-2,3,4,5-tetrahydro-1H-benzo[d]azepine (425 mg, 1 mmol), bis(triphenylphosphine)-palladium(II) chloride (0.1 equiv.), 4-[(cyclopentanecarbonyl-amino)-methyl]-phenyl-boronic acid (490 mg, 2.0 mmol) and sodium carbonate (2 equiv.) in THF/water (2:1, 15 mL) and heat the mixture at 80° C. for 6 h. Cool the reaction mixture to ambient temperature, dilute with EtOAc and wash with water. Dry the organic fraction over MgSO4, filter and concentrate in vacuo to obtain 7-chloro-6-{4-[(cyclopentanecarbonyl-amino)-methyl]-phenyl}-3-(2,2,2-trifluoroacetyl)-2,3,4,5-tetrahydro-1H-benzo[d]azepine, suitable for use without further purification.

Use a method similar to the General Procedure 1-2, using 7-chloro-6-{4-[(cyclopentanecarbonyl-amino)-methyl]-phenyl}-3-(2,2,2-trifluoroacetyl)-2,3,4,5-tetrahydro-1H-benzo[d]azepine (602 mg, 1.26 mmol) to obtain 7-chloro-6-{4-[(cyclopentanecarbonyl-amino)-methyl]-phenyl}-2,3,4,5-tetrahydro-1H-benzo[d]azepine. Use a method similar to the General Procedure 2-3 to give the title compound (340 mg, 70%). MS (ES+) m/z: 384 (M+H)+.

EXAMPLE 46

7-Chloro-6-{3-[(2,2,2-trifluoroethyl-amino)-methyl]-phenyl}-2,3,4,5-tetrahydro-1H-benzo[d]azepine (L)-Tartrate

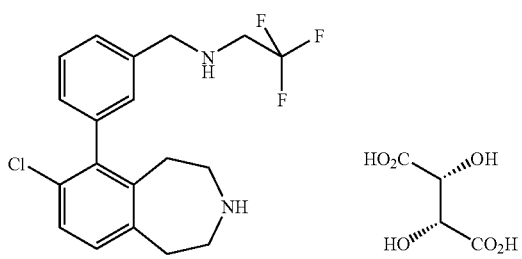 [SMILES: FC(F)(F)CNCc1cccc(-c2c(Cl)ccc3c2CCNCC3)c1 ; O=C(O)[C@H](O)[C@@H](O)C(=O)O]

Dissolve 7-chloro-3-(2,2,2-trifluoroacetyl)-6-trifluoromethanesulfonyloxy-2,3,4,5-tetrahydro-1H-benzo[d]azepine (425 mg, 1 mmol), bis(triphenylphosphine)-palladium(II) chloride (0.1 equiv.), 3-[(2,2,2-trifluoroethyl-amino)-methyl]-phenyl-boronic acid (465 mg, 2.0 mmol) and sodium carbonate (2 equiv.) in THF/water (2:1, 15 mL) and heat the mixture at 80° C. for 6 h. Cool the reaction mixture to ambient temperature, dilute with EtOAc and wash with water. Dry the organic fraction over MgSO4, filter and concentrate in vacuo to obtain 7-chloro-3-(2,2,2-trifluoroacetyl)-6-{3-[(2,2,2-trifluoroethyl-amino)-methyl]-phenyl}-2,3,4,5-tetrahydro-1H-benzo[d]azepine, suitable for use without further purification.

Use a method similar to the General Procedure 1-2, using 7-chloro-3-(2,2,2-trifluoroacetyl)-6-{3-[(2,2,2-trifluoroethyl-amino)-methyl]-phenyl}-2,3,4,5-tetrahydro-1H-benzo[d]azepine (528 mg, 1.14 mmol) to obtain 7-chloro-6-{3-[(2,2,2-trifluoroethyl-amino)-methyl]-phenyl}-2,3,4,5-tetrahydro-1H-benzo[d]azepine. Use a method similar to the General Procedure 2-3 to give the title compound (240 mg, 57%). MS (ES+) m/z: 369 (M+H)+.

The compounds of the present invention are relatively selective for the 5-HT$_{2C}$ receptor. The compounds of the present invention are particularly relatively selective for the 5-HT$_{2C}$ receptor in comparison to other 5-HT receptor subtypes and specifically the 5-HT$_{2A}$ and 5-HT$_{2B}$ receptors. This selectivity is demonstrated in the following agonist activity assays and receptor binding assays.

Agonist Activity Assays (G Alpha g-GTPγ[$^{35}$S] Binding Assays)

The 5-HT$_2$ receptors are functionally coupled to specific G-proteins. Agonist activation of 5-HT$_2$ G-protein-coupled receptors results in the release of GDP from the α-subunit (G alpha q or G alpha i) of the G-protein and the subsequent binding of GTP. The binding of the stable analog GTPγ[$^{35}$S] is an indicator of receptor activation (i.e. agonist activity).

The G alpha q-GTPγ[$^{35}$S] binding assay is used to determine the in vitro potency (EC$_{50}$) and maximal efficacy (E$_{max}$, normalized to the 5-HT response) of a test compound at the 5-HT$_{2A}$, 5-HT$_{2B}$, and 5-HT$_{2C}$ receptors. The area under the dose response curve (AUC) is also determined for each receptor subtype and used to measure the test compound's selectivity for the 5-HT$_{2C}$ receptor over the 5-HT$_{2A}$ and 5-HT$_{2B}$ receptors, expressed as Selectivity Ratios (AUC 2C/2A and AUC 2C/2B, respectively). The Selectivity Ratios allow the assessment of selectivity based on both potency and efficacy. A selectivity measure that incorporates both potency and efficacy at the 5-HT$_{2C}$ receptor, as compared to the 5-HT$_{2A}$ and 5-HT$_{2B}$. receptors, is considered important due to the adverse events associated with 5-HT$_{2A}$ and 5-HT$_{2B}$ agonist activity (see introduction). Membrane Preparation: Grow AV12 cells stably transfected with the human 5-HT$_{2A}$, 5-HT$_{2B}$, or 5-HT$_{2C}$ receptors in suspension, harvest by centrifugation, wash the cell pellet with phosphate buffered saline, pH 7.4, pellet the cells again, remove the supernatant, freeze the cell pellet on dry ice and store at −70° C. Thaw stock cell pellet and resuspend in 50 mM Tris, pH 7.4, aliquot into 1-2 mL volumes and refreeze at −70° C. for subsequent assays. (As is appreciated in the art, optimal cell quantities used per aliquot will vary with the individual transfected cell line used. In one embodiment, 5-HT$_{2A}$ and 5-HT$_{2C}$ transfected cells are typically used at about 6×10$^8$ cells per aliquot, while 5-HT$_{2B}$ cells are typically used at about 7.5×10$^8$ cells per aliquot).

On the day of assay, thaw membranes, wash the membranes with assay buffer (50 mM Tris-HCl (pH 7.4), 10 mM MgCl$_2$, 100 mM NaCl, and 0.2 mM EDTA), resuspend in assay buffer and incubate for 10 min. at 37° C. to hydrolyze any residual endogenous 5-HT. Wash the membranes again with assay buffer, and resuspend in assay buffer at a concentration to provide aliquots of about 1-4×10$^6$ cell equivalents per well (typically about 1-2×10$^6$ cell equivalents for assays with 5-HT$_{2A}$ or 5-HT$_{2C}$ receptor assays, and about 3-4×10$^6$ cell equivalents for assays with 5-HT$_{2B}$ receptor assays). Homogenize the cells with a tissue grinder and use the homogenate directly in the assay as described below.

G alpha q-GTPγ[$^{35}$S] Binding Assays: The immunoadsorption scintillation proximity assay (ISPA) of [$^{35}$S]-GTPγS binding to G alpha q is modified from published conditions (DeLapp et al, JPET 289 (1999) 946-955). Dissolve test compounds in DMSO and dilute in assay buffer to provide a range of concentrations to generate a concentration response curve. In wells of a 96 well microtiter plate, mix diluted test compound, GDP (0.1 μM final concentration), and [$^{35}$S]-GTPγS (between 0.5 and 1.0 nM final concentration). Add an aliquot of membranes to the incubation mixture and mix the plates to initiate agonist stimulation of the nucleotide exchange (200 μl final volume). Incubate the microtiter plates for 30 min. at room temperature. Quench the incubation with IGEPAL® CA-630 detergent (0.27% final concentration). Add affinity purified polyclonal rabbit anti-G alpha q antibody (about 1-2 μg per well), and anti-rabbit Ig scintillation proximity assay beads (Amersham; about 1.25 mg per well; 300 μl final volume). Seal the plates and incubate the mixture for 3 h at room temperature. Centrifuge the microtiter plates briefly to pellet beads. Quantitate the GTP-γ[$^{35}$S] binding by microtiter plate scintillation spectrometry (Wallac Trilux MicroBeta™ scintillation counter).

Data Analysis: For each concentration response curve for a test compound at a given receptor, analyze the data with GraphPad Prism™ software (v3.02; GraphPad Software, San Diego, Calif.) running on a personal computer with MicroSoft Windows OS®, using nonlinear regression analysis curve fitting to determine the EC$_{50}$ and E$_{max}$ (normalized to 5-HT control curves). Determine the Area Under the agonist concentration-response Curve (AUC) with GraphPad Prism™ by the trapezoidal method.

To calculate the Selectivity Ratios, first, determine the AUC for the test compound for each receptor subtype as described above. Second, normalize the AUC's at each receptor subtype relative to the AUC determined for 5-HT at that receptor. The normalized AUC for a test compound at a given receptor is therefore expressed as a percentage of the AUC determined for 5-HT at that receptor. For example:

5HT$_{2A}$ Normalized AUC =
$$a = \frac{(AUC_{test\ compound}\ at\ 5HT_{2A}\ receptor)}{(AUC_{5\text{-}HT}\ at\ 5HT_{2A}\ receptor)} \times 100\%$$

5HT$_{2B}$ Normalized AUC =
$$b = \frac{(AUC_{test\ compound}\ at\ 5HT_{2B}\ receptor)}{(AUC_{5\text{-}HT}\ at\ 5HT_{2B}\ receptor)} \times 100\%$$

5HT$_{2C}$ Normalized AUC =
$$c = \frac{(AUC_{test\ compound}\ at\ 5HT_{2C}\ receptor)}{(AUC_{5\text{-}HT}\ at\ 5HT_{2C}\ receptor)} \times 100\%$$

Third, calculate the Selectivity Ratios for the test compound as follows:

Selectivity Ratio for 5-HT$_{2C}$ receptor/5-HT$_{2A}$ receptor (AUC 2C/2A)=c/a

Selectivity Ratio for 5-HT$_{2C}$ receptor/5-HT$_{2B}$ receptor (AUC 2C/2B)=c/b

For reference purposes, the AUC 2C/2A and AUC 2C/2B for 5-HT are each 1.0. Likewise, the ratios for mCPP (meta-chlorophenylpiperazine) are tested and are found to be 2.1 and 2.1 respectively.

Representative compounds of the present invention are tested in the G alpha q-GTPγ[$^{35}$S] assays for the 5-HT$_{2A}$, 5-HT$_{2B}$, and 5-HT$_{2C}$ receptors essentially as described above and are found to be a highly potent and selective agonists of the 5-HT$_{2C}$ receptor, with EC$_{50}$'s typically less than or equal to 200 nM, and AUC 2C/2A and AUC 2C/2B ratios greater than 1.5. Preferred compounds are those with EC50's less than or equal to 100 nM, and AUC 2C/2A and AUC 2C/2B ratios greater than or equal to 2.0. More preferred are those with EC50's less than or equal to 50 nM, and AUC 2C/2A and AUC 2C/2B ratios greater than or equal to 3.0.

Ligand Binding Assays

The ligand binding affinity of the compounds of the present invention to the 5-HT$_{2C}$ receptor subtype is measured essentially as described by Wainscott (Wainscott, et al., *Journal of Pharmacology and Experimental Therapeutics*, 276:720-727 (1996)). Data is analyzed by nonlinear regression analysis on the concentration response curves using the four parameter logistic equation described by DeLean (DeLean, et al, *Molecular Pharmacology*, 21, 5-16 (1982)). IC$_{50}$ values are converted to K$_i$ values using the Cheng-Prusoff equation (Cheng, et al., *Biochem. Pharmacol.*, 22, 3099-3108 (1973)).

Representative compounds of the present invention are tested essentially as described above and are found to have excellent affinity for the 5-HT$_{2C}$ receptor, with K$_i$'s typically less than or equal to about 200 nM. Preferred compounds are those with K$_i$'s of less than or equal to about 100 nM. More preferred are those with K$_i$'s less than or equal to 50 nM.

Affinities for other receptor subtypes can readily be determined by slight modification of the above described radioligand receptor binding assay using cells transfected with the desired receptor in place of cells transfected with the 5-HT$_{2C}$ receptor subtype and using an appropriate radioligand. The binding affinities for representative compounds of the present invention for a variety of receptors are determined in such assays and the compounds are found to have surprisingly higher affinity for the 5-HT$_{2C}$ receptor. Affinity for the 5-HT$_{2C}$ receptor is found to be significantly higher than for other 5-HT receptor subtypes, and notably higher than the 5-HT$_{2A}$ and 5-HT$_{2B}$ receptor subtypes. Preferred compounds are those with IC$_{50}$'s equal to or greater than 300 nM for the alpha 1 and alpha 2 adrenergic receptors and equal to or greater than 500 nM for $D_1$ and $D_2$ dopaminergic receptors. More preferred compounds are those with $IC_{50}$'s equal to or greater than 1000 nM for the alpha 1 and alpha 2 adrenergic receptors and the $D_1$ and $D_2$ dopaminergic receptors. Still more preferred are those compounds with $IC_{50}$'s equal to or greater than 3000 nM for the alpha 1 and alpha 2 adrenergic receptors and the $D_1$ and $D_2$ dopaminergic receptors.

For the above in vitro assays, exemplified compounds are assayed and found to have either an $EC_{50}$ or a $K_i$ value of equal to or less than 50 nM, and to have AUC 2C/2A and AUC 2C/2B ratios of greater than or equal to 2.0. Exemplified compounds are assayed and found to have alpha 1 and alpha 2 adrenergic receptor $IC_{50}$'s equal to or greater than 300 nM, and $D_1$ and $D_2$ dopaminergic receptor $IC_{50}$'s equal to or greater than 500 nM.

Rat Feeding Assays

The ability of the compounds of the present invention to treat obesity is demonstrated by testing in acute and chronic rat feeding assays.

Animals: Obtain male Long-Evans rats (Harlan Sprague-Dawley, Indianapolis, Ind.) that are approximately one hundred-days old and have been maintained on a calorie rich diet since weaning (TD 95217, 40% calories from fat; Teklad, Madison, Wis.). House the rats individually with a 12 h: 12 h light:dark cycle (lights on from about 22:00 h to about 10:00 h) and maintain rats on the same diet (TD 95217) with free access to water, for about 1-2 weeks to acclimate the rats to the environment. Dose rats orally with vehicle (10% acacia with 0.15% saccharin in water) once daily for at least 1 day (typically 1-2 days) to acclimate the rats to the procedures. Randomize the rats into groups so each group has similar mean body weights.

Calorimetric Acute Feeding Assay: At approximately 8:00 h on the day of assay, weigh each rat and transfer to individual chambers of an open circuit calorimetry system (Oxymax, Columbus Instruments International Corporation; Columbus, Ohio), with free access to food (pre-weighed) and water, and begin measuring $VO_2$ and $VCO_2$. At approximately 10:00 h, dose rats orally with vehicle or test compound, return them to their calorimetry chambers, and continue measuring $VO_2$ and $VCO_2$ at regular time intervals (approximately hourly). At approximately 8:00 h the following day, measure rat body weight and the remaining food, assuming the difference in weight of food is equal to the mass of food consumed. Calculate the 24 h energy expenditure (EE) and respiratory quotient (RQ) essentially as described in Chen, Y. and Heiman, M. L., Regulatory Peptide, 92:113-119 (2000). EE during light photoperiod is indicative of the resting metabolic rate and RQ is indicative of the fuel source the animal utilizes (pure carbohydrate metabolism gives an RQ of about 1.0, pure fat metabolism gives an RQ of about 0.7, mixed carbohydrate and fat metabolism gives intermediate values for RQ). Calculate EE as the product of calorific value (CV) and $VO_2$ per body weight (kg); where $CV=3.815+1.232*RQ$, and RQ is the ratio of $CO_2$ produced ($VCO_2$) to $O_2$ consumed ($VO_2$). Caloric intake is calculated as (mass of 24 h food intake in grams)×(physiological fuel value of the diet in kilocalorie/g) per kg of body weight.

Acute Feeding Assay with a selective 5-$HT_{2C}$ receptor antagonist: The above calorimetric acute feeding assay is conducted with the following modifications. Open circuit calorimetry systems are not used and only the 24 h periodic food intake and body weight are measured. Three groups of rats are used with the first group receiving a subcutaneous dose of saline (0.5 mL) about 15 minutes prior to the oral dose of vehicle, the second group receiving a subcutaneous dose of saline (0.5 mL) about 15 minutes prior to the oral dose of test compound in vehicle, and the third group receiving a subcutaneous injection of a selective 5-$HT_{2C}$ receptor antagonist, 6-chloro-5-methyl-N-{2-[(2-methylpyridin-3-yl-oxy)pyridin-5-yl]aminocarbonyl}-2,3-dihydroindole (3 mg/Kg, in 35% cyclodextrin, 0.5 mL), about 15 min. prior to the oral dose of test compound in vehicle.

Chronic Feeding Assay: At between approximately 8:00 h and 10:00 h on day one of the assay, weigh and orally dose each rat with vehicle or test compound and return the animal to its home cage, with free access to food (pre-weighed) and water. For each of days 2-15, at between approximately 8:00 h and 10:00 h, measure rat body weight and the weight of food consumed in the last 24 h period, and administer daily oral dose of test compound or vehicle. On days −2 and 15 measure total fat mass and lean mass by nuclear magnetic resonance (NMR) using an EchoMRI™ system (Echo Medical Systems, Houston Tex.). (See Frank C. Tinsley, Gersh Z. Taicher, and Mark L. Heiman, "Evaluation of a New Quantitative Magnetic Resonance (QMR) Method for Mouse Whole Body Composition Analysis", Obesity Research, submitted May 1, 2003.)

Representative compounds of the present invention are tested in acute and chronic feeding assays essentially as described above. In the acute assays, the compounds are found to significantly reduce 24 h food intake, which effect is blocked by pre-administration of the 5-$HT_{2C}$ receptor antagonist. The compounds also are found to dose-dependently reduce RQ without significantly changing the energy expenditure during the light photo-period. Thus the compounds are found to reduce caloric intake and increase the proportion of fuel deriving from fat utilization, without significantly changing the resting metabolic rate. In the chronic assay, the compounds are found to significantly decrease cumulative food intake and cumulative body weight change in a dose-dependent manner compared to control animals. The decrease in body weight is found to be due to loss of adipose tissue while lean body mass is not changed.

The ability of the 5-$HT_{2C}$ receptor agonists of the present invention to treat obsessive/compulsive disorder is demonstrated by testing in a variety of in vivo assays as follows:

Marble Burying Assay

Marble burying in mice has been used to model anxiety disorders including obsessive-compulsive disorders (OCD) due to ethological study of the behavior (e.g. Gyertyan I. "Analysis of the marble burying response: Marbles serve to measure digging rather than evoke burying", *Behavioural Pharmacology* 6: 24-31, (1995)) and due to the pharmacological effects of clinical standards (c.f., Njung'E K. Handley S L. "Evaluation of marble-burying behavior as a model of anxiety", *Pharmacology, Biochemistry & Behavior.* 38: 63-67, (1991)); Borsini F., Podhorna J., and Marazziti, D. "Do animal models of anxiety predict anxiolytic effects of antidepressants?", *Psychopharmacology* 163: 121-141, (2002)). Thus, drugs used in the treatment of generalized anxiety in humans (e.g. benzodiazepines) as well as compounds used to treat OCD (e.g. SSRIs like fluoxetine) decrease burying.

House experimentally-naïve male, NIH Swiss mice (Harlan Sprague-Dawley, Indianapolis, Ind.) weighing between 28-35 g in groups of 12 for at least three days prior to testing in a vivarium with 12 h light and dark cycles. Conduct experiments during the light cycle in a dimly lit experimental testing room. Dose mice with vehicle or test compound and, after a specified pretreatment interval (generally 30 min.), place each mouse individually on a rotorod (Ugo Basile 7650)

operating at a speed of 6 revolutions/min. and observe for falling. After 2 min. on the rotorod, place the mice individually in a 17×28×12 cm high plastic tub with 5 mm sawdust shavings on the floor that are covered with 20 blue marbles (1.5 cm diameter) placed in the center. After 30 min., count the number of marbles buried (⅔ covered with sawdust). Assess the test compound's effect on marble burying with Dunnett's test and the effect on rotorod performance by Fisher's exact test.

Clinically effective standard compounds suppress marble burying at doses that are devoid of motor-impairing effects as measured on the rotorod. The in vivo efficacy of $5HT_{2C}$ compounds at the $5HT_{2C}$ receptor is confirmed by the prevention of effects of the $5HT_{2C}$ agonists on marble burying by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the marble burying assay essentially as described and are surprisingly found to reduce burying behavior in the test mice. The reduction of burying behavior is found to be blocked by co-administration of the $5-HT_{2C}$ antagonist. In contrast to the compounds of the present invention, the anxiolytic compound chlordiazepoxide and the antipsychotic compound chlorpromazine decrease marble burying only at doses that also disrupt rotorod performance.

Nestlet Shredding

Mice naturally will construct nests of material available in their living environment. Since this behavior is obsessive in nature, it has been used to model OCD (Xia Li, Denise Morrow and Jeffrey M. Witkin, "Decreases in nestlet shredding of mice by serotonin uptake inhibitors: comparison with marble burying", Psychopharmacology, submitted Jul. 14, 2003). House experimentally-naïve male, NIH Swiss mice (Harlan Sprague-Dawley, Indianapolis, Ind.) weighing between 28-35 g in groups of 12 for at least three days prior to testing in a vivarium with a 12 h light/dark cycle. Conduct experiments during the light cycle in an experimental room with normal overhead fluorescent lighting. Dose mice with vehicle or test compound and after a specified pretreatment interval (generally 30 min.), place the mice individually in a 17×28×12 cm high plastic tub with about 5 mm sawdust shavings on the floor along with a pre-weighed multi-ply gauze pad (51 mm square). After 30 min., weigh the remainder of the gauze pad not removed by the mouse. Determine the weight of the gauze used for nestlet construction by subtraction. Compare the results for test compound treated mice to the results for vehicle control treated mice with Dunnett's test.

Clinically effective OCD treatment standard compounds suppress nestlet shredding at doses that are devoid of motor-impairing effects as measured by the rotorod test. The in vivo efficacy of $5HT_{2C}$ compounds at the $5HT_{2C}$ receptor is confirmed by the prevention of effects of the $5HT_{2C}$ agonists on nestlet shredding by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed essentially as described above and are surprisingly found to suppress nestlet shredding at doses that are devoid of motor-impairing effects as measured by the rotorod test.

In contrast to the compounds of the present invention, the anxiolytic chlordiazepoxide and the psychomotor stimulant d-amphetamine decreases nestlet shredding only at doses that produce motoric side effects (depression or stimulation, respectively).

Schedule-Induced Polydipsia

Food-deprived rats exposed to intermittent presentations of food will drink amounts of water that are far in excess of their normal daily intake and in excess of their intake when given all of their food at one time (Falk J L. "Production of polydipsia in normal rats by an intermittent food schedule", Science 133: 195-196, (1961)). This excessive behavior is persistent and has been used to model OCD.

Maintain Wistar rats on a food restricted diet (to maintain 85% free feeding weight), but with free access to water. Train the rats in a behavioral testing chamber to press a lever to receive a food pellet under a fixed interval schedule, such that the rats are rewarded with a 45 mg food pellet the first time they press a lever after a 120 second interval has elapsed. The fixed interval is then reset to 120 seconds and the process repeated. Thus, during a 90 min. test session, the rats can earn a maximum of 45 pellets. The behavioral chamber is also equipped with a water bottle that is weighed before and after the session to determine the amount of water consumed.

Administer test compounds on Tuesdays and Fridays. Determine control day performances on Thursdays. Administer compounds either orally at 60 min. before the beginning of a test session, or subcutaneously at 20 min. before the beginning of a test session. Compare the rates of lever pressing and water consumption for each animal's performance during sessions after test compound treatment with that animal's performance during control sessions, expressed as a percent of the control rate. Average the individual percent of control rates for each dose and calculate the standard error of the mean.

Clinically effective OCD treatment standard compounds (e.g. chlomipramine, fluoxetine) suppress schedule-induced polydipsia without producing notable changes in motor patterns, food intake, or behavior the following day. The in vivo efficacy of $5HT_{2C}$ compounds at the $5HT_{2C}$ receptor is confirmed by the prevention of effects of the $5HT_{2C}$ agonists on excessive drinking by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the schedule-induced polydipsia assay essentially as described above and are surprisingly found to suppress schedule-induced polydipsia without producing notable changes in motor patterns, food intake, or behavior the following day. The behavior suppression is blocked by co-administration of the $5-HT_{2C}$ antagonist.

In contrast to the compounds of the present invention, the psychomotor stimulant d-amphetamine decreases excessive drinking only at behaviorally stimulating doses and these effects are not prevented by the $5HT_{2C}$ receptor antagonist.

While it is possible to administer compounds employed in the methods of this invention directly without any formulation, the compounds are usually administered in the form of pharmaceutical compositions comprising a pharmaceutically acceptable excipient and at least one compound of Formula I or a pharmaceutically acceptable salt thereof. These compositions can be administered by a variety of routes including oral, rectal, transdermal, subcutaneous, intravenous, intramuscular, and intranasal. The compounds employed in the methods of this invention are effective as both injectable and oral compositions. Such compositions are prepared in a manner well known in the pharmaceutical art. See, e.g. REMINGTON'S PHARMACEUTICAL SCIENCES, (16th ed. 1980).

In making the compositions employed in the present invention the active ingredient is usually mixed with at least one excipient, diluted by at least one excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Under some circumstances, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compound employed, the type of pharmacokinetic profile desired from the route of administration, and the state of the patient.

We claim:
1. A compound of Formula I:

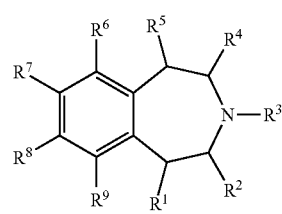

where:
$R^1$ is hydrogen;
$R^2$, $R^3$, and $R^4$ are each hydrogen;
$R^5$ is hydrogen;
$R^6$ is —C≡C—$R^{10}$;
$R^7$ is chloro;
$R^8$ is hydrogen;
$R^9$ is hydrogen;
$R^{10}$ is
  $R^{12}$—C(O)N($R^{13}$)—($C_1$-$C_5$)alkyl
$R^{12}$ is ($C_1$-$C_6$)alkyl optionally substituted with 1 to 6 fluoro substituents;
  ($C_3$-$C_7$)cycloalkyl($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl,
  ($C_1$-$C_6$)alkoxy-($C_0$-$C_5$)alkyl optionally substituted on the alkoxy and alkyl moieties independently with 1 to 6 fluoro substituents,
  ($C_3$-$C_7$)cycloalkyloxy-($C_0$-$C_5$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, $(C_1-C_6)$alkyl-S-$(C_1-C_5)$alkyl optionally substituted on each alkyl moiety independently with 1 to 6 fluoro substituents, $(C_3-C_7)$cycloalkyl-S-$(C_1-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkyl optionally substituted on the alkyl moiety with 1 to 6 fluoro substituents, or $Ar^4$—$(C_0-C_3)$alkyl optionally substituted on the alkyl moiety with 1 to 6 fluoro substituents;

$R^{13}$ is hydrogen or $(C_1-C_3)$alkyl optionally substituted with 1 to 6 fluoro substituents;

$Ar^4$ is pyridyl optionally substituted with 1 to 4 independently selected halo substituents, or with 1 to 3 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylsulfonyl, $(C_1-C_6)$alkyl-C(O)—, and $(C_1-C_6)$alkyl-NHC(O)—;

$Ph^3$ is phenyl optionally substituted with 1 to 5 independently selected halo substituents, or with 1 to 3 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylsulfonyl, $(C_1-C_6)$alkyl-C(O)—, and $(C_1-C_6)$alkyl-NHC(O)—;

or a pharmaceutically acceptable salt thereof.

2. A compound according to formula Ia:

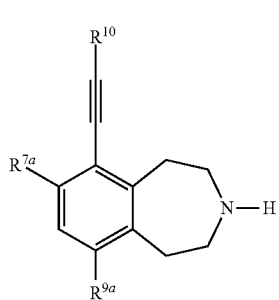

Ia wherein
$R^{7a}$ is chloro;
$R^{9a}$ is hydrogen; and
$R^{10}$ is
$R^{14}R^{15}NC(O)$—$NR^{13}$—$(C_1-C_5)$alkyl optionally substituted on the moiety with 1 to 6 fluorine substituents,
$R^{13}$ is hydrogen or $(C_1-C_3)$alkyl optionally substituted with 1 to 6 fluoro substituents;

$R^{14}$ is $(C_1-C_6)$alkyl optionally substituted with 1 to 6 fluoro substituents;

$(C_3-C_7)$cycloalkyl$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $(C_1-C_6)$alkoxy-$(C_1-C_5)$alkyl optionally substituted on the alkoxy and alkyl moieties independently with 1 to 6 fluoro substituents, $(C_3-C_7)$cycloalkyloxy-$(C_1-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $(C_1-C_6)$alkyl-S—$(C_1-C_5)$alkyl optionally substituted on the alkyl moieties independently with 1 to 6 fluoro substituents, $(C_3-C_7)$cycloalkylthio-$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, $Ph^3$-$(C_0-C_3)$alkyl optionally substituted on the alkyl moiety with 1 to 6 fluoro substituents, or $Ar^4$—$(C_0-C_3)$alkyl optionally substituted on the alkyl moiety with 1 to 6 fluoro substituents;

$R^{15}$ is hydrogen or $(C_1-C_3)$alkyl optionally substituted with 1 to 6 fluoro substituents, or $R^{14}$ and $R^{15}$ may be taken together with the nitrogen atom to which they are attached to form $Het^2$;

$Ar^4$ is pyridyl optionally substituted with 1 to 4 independently selected halo substituents, or with 1 to 3 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylsulfonyl, $(C_1-C_6)$alkyl-C(O)—, and $(C_1-C_6)$alkyl-NHC(O)—;

$Het^2$ is a saturated, nitrogen-containing heterocycle substituent selected from the group consisting of pyrrolidinyl, piperidinyl, homopiperidinyl, morpholinyl, thiomorpholinyl, homomorpholinyl, homothiomorpholinyl, and piperazine, any one of which may optionally be substituted with $(C_2-C_6)$alkyl optionally substituted with 1 to 6 fluro substituents, or with 1 to 2 methyl substituents each optionally substituted with 1 to 3 fluoro substituents;

$Ph^3$ is phenyl optionally substituted with 1 to 5 independently selected halo substituents, or with 1 to 3 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylsulfonyl, $(C_1-C_6)$alkyl-C(O)—, and $(C_1-C_6)$alkyl-NHC(O)—;
or a pharmaceutically acceptable salt thereof.

3. A compound according to formula Ib:

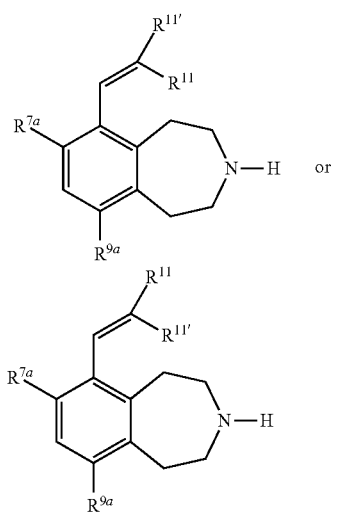

wherein
$R^{7a}$ is chloro;
$R^{9a}$ is hydrogen;
$R^{11}$ is $Ar^1$—$(C_0-C_3)$alkyl optionally substituted on the alkyl moiety with 1 to 6 fluoro substituents, $Ph^2$-$(C_0-C_3)$alkyl optionally substituted on the alkyl moiety with 1 to 6 fluoro substituents, $R^{12}$—C(O)N($R^{13}$)—$(C_1-C_5)$alkyl optionally substituted on the alkyl moiety with 1 to 6 fluoro substituents, or $Het^1$-$(C_1-C_5)$alkyl optionally substituted on the alkyl moiety with 1 to 6 fluoro substituents;
$R^{11'}$ is hydrogen or methyl;
$R^{12}$ is $(C_1-C_6)$alkyl optionally substituted with 1 to 6 fluoro substituents;
$(C_3-C_7)$cycloalkyl($C_0-C_3$)alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkoxy-$(C_0-C_5)$alkyl optionally substituted on the alkoxy and alkyl moieties independently with 1 to 6 fluoro substituents,
$(C_3-C_7)$cycloalkyloxy-$(C_0-C_5)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-S—$(C_1-C_5)$alkyl optionally substituted on each alkyl moiety independently with 1 to 6 fluoro substituents,
$(C_3-C_7)$cycloalkyl-S—$(C_1-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$Ph^3$-$(C_0-C_3)$alkyl optionally substituted on the alkyl moiety with 1 to 6 fluoro substituents, or
$Ar^4$—$(C_0-C_3)$alkyl optionally substituted on the alkyl moiety with 1 to 6 fluoro substituents;
$R^{13}$ is hydrogen or $(C_1-C_3)$alkyl optionally substituted with 1 to 6 fluoro substituents;
$Ar^1$ is an aromatic heterocycle substituent selected from the group consisting of pyrrolyl furanyl, thiophenyl, thiazolyl, isothiazolyl, oxazolyl, isoxazolyl and pyridyl, any of which may optionally be substituted with 1 to 3 substituents independently selected from the group consisting of halo, $(C_1-C_3)$alkyl, $(C_1-C_3)$alkoxy, —$CF_3$, —O—$CF_3$, nitro, cyano, hydroxy and —$SCF_3$,
wherein when $Ar^1$ is pyridyl, said pyridyl may alternatively, optionally be substituted with
i) 1 to 4 independently selected halo substituents; or
ii) 1 to 3 substituents independently selected from the group consisting of halo, cyano, and hydroxy, methyl, —$CF_3$, and methoxy; or
iii) 0, 1, or 2 substituents independently selected from the group consisting of halo, cyano, and hydroxy, methyl, —$CF_3$, and methoxy, and further substituted with one substituent selected from the group consisting of
$(C_1-C_6)$alkyl optionally substituted with 1 to 6 fluoro substituents,
$(C_1-C_6)$alkoxy-$(C_0-C_3)$alkyl optionally substituted on the alkoxy and alkyl moieties independently with 1 to 6 fluoro substituents,
$(C_3-C_7)$cycloalkyloxy-$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally further substituted with 1 to 6 fluoro substituents, provided that no more than 2 of the substituents on the cycloalkyl moiety are alkyl,
$(C_1-C_6)$alkyl-S—$(C_0-C_3)$alkyl optionally substituted on the alkyl moieties independently with 1 to 6 fluoro substituents,
$(C_3-C_7)$cycloalkylthio($C_0-C_3$)alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl,
$(C_1-C_6)$alkyl-$SO_2$—$(C_0-C_3)$alkyl optionally substituted on the alkyl moieties independently with 1 to 6 fluoro substituents,
$(C_3-C_7)$cycloalkyl-$SO_2$—$(C_0-C_3)$alkyl optionally substituted on the alkyl moiety with 1 to 6 fluoro substituents, and optionally substituted on the cycloalkyl moiety with 1 to 6 substituents independently selected from fluoro and $(C_1-C_4)$alkyl optionally substituted with 1 to 6 fluoro substituents, provided that no more than 2 of the substituents on the cycloalkyl moiety are alkyl, ($C_1$-$C_6$)alkyl-C(O)—($C_0$-$C_3$)alkyl optionally substituted on the alkyl moieties independently with 1 to 6 fluoro substituents, ($C_3$-$C_7$)cycloalkyl-C(O)—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-C(O)NH—($C_0$-$C_3$)alkyl optionally substituted on the alkyl moieties independently with 1 to 6 fluoro substituents, ($C_3$-$C_7$)cycloalkyl-C(O)NH—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-NHC(O)—($C_0$-$C_3$)alkyl optionally substituted on the alkyl moieties independently with 1 to 6 fluoro substituents, and ($C_3$-$C_7$)cycloalkyl-NHC(O)—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl;

$Ar^3$ is pyridyl optionally substituted with 1 to 4 independently selected halo substituents, or with 1 to 3 substituents independently selected from the group consisting of halo, cyano, hydroxy, —$SCF_3$, ($C_1$-$C_6$)alkyl optionally further substituted with 1 to 6 fluoro substituents, and ($C_1$-$C_6$)alkoxy optionally further substituted with 1 to 6 fluoro substituents;

$Ar^4$ is pyridyl optionally substituted with 1 to 4 independently selected halo substituents, or with 1 to 3 substituents independently selected from the group consisting of halo, cyano, hydroxy, ($C_1$-$C_6$)alkyl optionally further substituted with 1 to 6 fluoro substituents, ($C_1$-$C_6$) alkoxy optionally further substituted with 1 to 6 fluoro substituents, ($C_1$-$C_6$)alkylthio optionally further substituted with 1 to 6 fluoro substituents, ($C_1$-$C_6$)alkylsulfonyl, ($C_1$-$C_6$)alkyl-C(O)—, and ($C_1$-$C_6$)alkyl-NHC(O)—;

$Het^1$ is a heterocycle, linked through either carbon or nitrogen, selected from the group consisting of pyrazolyl, pyrazolinyl, pyrazolidinyl, imidazolyl, imidazolinyl, imidazolidinyl, thiazolyl, thiazolinyl, thiazolidinyl, oxazolyl, oxazolinyl, oxazolidinyl, pyrrolyl, pyrrolinyl, pyrrolidinyl, 1,2,4-triazolyl, 1,3,4-triazolyl, piperidyl, tetrahydropyridyl, dihydropyridyl, piperazinyl, tetrahydropyrazinyl, dihydropyrazinyl, hexahydropyrimidyl, tetrahydropyrimidyl, dihydropyrimidyl, morpholinyl, thiomorpholinyl, homomorpholinyl, homopiperidinyl, indazolyl, indazolinyl, benzimidazolyl, benzimidazolinyl, benzothiazolyl, benzothiazolinyl, benzoxazolyl, benzoxazolinyl, indolyl, indolinyl, isoindolyl, isoindolinyl, benzotriazolyl, dihydroquinolinyl, tetrahydroquinolinyl, dihydroisoquinolinyl, tetrahydroisoquinolinyl, dihydroquinazolinyl, tetrahydroquinazolinyl, dihydroquinoxalinyl, tetrahydroquinoxalinyl, benzoxazinyl, benzothiazinyl, benzazepinyl, and benzoxazepinyl, any one of which may be optionally substituted on carbon atoms of the heterocyclic ring with 1 to 2 oxo substituents, and independently optionally substituted on either carbon or nitrogen atoms of the heterocyclic ring, with 1 to 2 substituents independently selected from the group consisting of ($C_1$-$C_6$) alkyl optionally further substituted with 1 to 6 fluoro substituents, $Ph^1$-($C_0$-$C_3$)alkyl optionally further substituted on the alkyl moiety with 1 to 6 fluoro substituents, and $Ar^3$—($C_0$-$C_3$) alkyl optionally further substituted on the alkyl moiety with 1 to 6 fluoro substituents, or two adjacent substituents taken together with the heterocyclic ring atoms to which they are attached form a 5- or 6-membered saturated or partially saturated ring;

$Ph^1$ is phenyl optionally substituted with 1 to 5 independently selected halo substituents, or with 1 to 3 substituents independently selected from the group consisting of halo, cyano, —$SCF_3$, hydroxy, ($C_1$-$C_6$)alkyl optionally further substituted with 1 to 6 fluoro substituents, and ($C_1$-$C_6$)alkoxy optionally further substituted with 1 to 6 fluoro substituents;

$Ph^2$ is phenyl optionally substituted with
i) 1 to 5 independently selected halo substituents; or
ii) 1 to 3 substituents independently selected from the group consisting of halo, cyano, hydroxy, methyl, methoxy, and —$CF_3$; or
iii) 0, 1 or 2 substituents independently selected from the group consisting of halo, cyano, hydroxy, methyl, methoxy, and —$CF_3$, and further substituted with one substituent selected from the group consisting of ($C_1$-$C_6$)alkyl optionally substituted with 1 to 6 fluoro substituents, ($C_1$-$C_6$)alkoxy-($C_0$-$C_3$)alkyl optionally substituted on the alkoxy and alkyl moieties independently with 1 to 6 fluoro substituents, ($C_3$-$C_7$)cycloalkyloxy-($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-S—($C_0$-$C_3$)alkyl optionally substituted on the alkyl moieties independently with 1 to 6 fluoro substituents, ($C_3$-$C_7$)cycloalkylthio($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-$SO_2$—($C_0$-$C_3$)alkyl optionally substituted on the alkyl moieties independently with 1 to 6 fluoro substituents, ($C_3$-$C_7$)cycloalkyl-$SO_2$—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-C(O)—($C_0$-$C_3$)alkyl optionally substituted on the alkyl moieties independently with 1 to 6 fluoro substituents, ($C_3$-$C_7$)cycloalkyl-C(O)—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-C(O)NH—($C_0$-$C_3$)alkyl optionally substituted on the alkyl moieties independently with 1 to 6 fluoro substituents, ($C_3$-$C_7$)cycloalkyl-C(O)NH—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-NHC(O)—($C_0$-$C_3$)alkyl optionally substituted on the alkyl moieties independently with 1 to 6 fluoro substituents, and ($C_3$-$C_7$)cycloalkyl-NHC(O)—($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl; and $Ph^3$ is phenyl optionally substituted with 1 to 5 independently selected halo substituents, or with 1 to 3 substituents independently selected from the group consisting of halo, cyano, hydroxy, ($C_1$-$C_6$)alkyl optionally further substituted with 1 to 6 fluoro substituents, ($C_1$-$C_6$)alkoxy optionally further substituted with 1 to 6 fluoro substituents, ($C_1$-$C_6$)alkylthio optionally further substituted with 1 to 6 fluoro substituents, ($C_1$-$C_6$)alkylsulfonyl, ($C_1$-$C_6$)alkyl-C(O)—, and ($C_1$-$C_6$)alkyl-NHC(O)—;

or a pharmaceutically acceptable salt thereof.

4. A compound according to formula Ic:

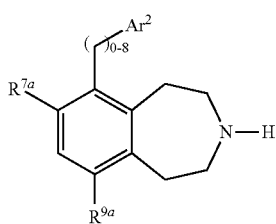

Ic wherein
$R^{7a}$ is chloro;
$R^{9a}$ is hydrogen;
$Ar^2$ is an aromatic group linked through carbon selected from the list consisting of phenyl, naphthyl, pyrrolyl, 1,2,3-triazolyl, thiophenyl, thiazolyl, isothiazolyl, oxazolyl, isoxazolyl and pyridyl, any one of which may be optionally substituted with 1 to 5 independently selected halo substituents, or with 1 to 3 substituents independently selected from the group consisting of halo, cyano, phenyl, hydroxy, ($C_1$-$C_6$)alkyl optionally further substituted with 1 to 6 fluoro substituents, ($C_1$-$C_6$)alkoxy optionally further substituted with 1 to 6 fluoro substituents, ($C_1$-$C_6$)alkylthio optionally further substituted with 1 to 6 fluoro substituents, ($C_1$-$C_6$)alkyl-$NR^{13}$—($C_1$-$C_3$)alkyl optionally further substituted on an alkyl moiety with 1 to 6 fluoro substituents, ($C_3$-$C_7$)cycloalkyl-($C_0$-$C_3$)alkyl-$NR^{13}$—($C_1$-$C_3$)alkyl optionally further substituted on an alkyl moiety with 1 to 6 fluoro substituents, ($C_1$-$C_6$)alkyl-C(O)$NR^{13}$—($C_1$-$C_3$)alkyl optionally further substituted on an alkyl moiety with 1 to 6 fluoro substituents, and ($C_3$-$C_7$)cycloalkyl-($C_0$-$C_3$)alkyl-$NR^{13}$—($C_1$-$C_3$)alkyl optionally further substituted on an alkyl moiety with 1 to 6 fluoro substituents; and $R^{13}$ is hydrogen or ($C_1$-$C_3$)alkyl optionally substituted with 1 to 6 fluoro substituents;

or a pharmaceutically acceptable salt thereof.

5. A compound according to formula Id:

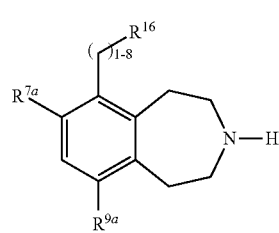

Id wherein
$R^{7a}$ is chloro;
$R^{9a}$ is hydrogen;
$R^{16}$ is -$Het^1$ or —$N(R^{13})C(O)$—$R^{12}$;
$R^{12}$ is ($C_1$-$C_6$)alkyl optionally substituted with 1 to 6 fluoro substituents;

($C_3$-$C_7$)cycloalkyl($C_0$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkoxy-($C_0$-$C_5$)alkyl optionally substituted on the alkoxy and alkyl moieties independently with 1 to 6 fluoro substituents, ($C_3$-$C_7$)cycloalkyloxy-($C_0$-$C_5$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl, ($C_1$-$C_6$)alkyl-S—($C_1$-$C_5$)alkyl optionally substituted on each alkyl moiety independently with 1 to 6 fluoro substituents, ($C_3$-$C_7$)cycloalkyl-S—($C_1$-$C_3$)alkyl optionally substituted on the alkyl moiety with 1 to 6 fluoro substituents, and optionally substituted on the cycloalkyl moiety with 1 to 6 substituents independently selected from fluoro and ($C_1$-$C_4$)alkyl optionally substituted with 1 to 6 fluoro substituents, provided that no more than 2 of the substituents on the cycloalkyl moiety are alkyl,
$Ph^3$-$(C_0$-$C_3)$alkyl optionally substituted on the alkyl moiety with 1 to 6 fluoro substituents, or
$Ar^4$—$(C_0$-$C_3)$alkyl optionally substituted on the alkyl moiety with 1 to 6 fluoro substituents;

$R^{13}$ is hydrogen or $(C_1$-$C_3)$alkyl optionally substituted with 1 to 6 fluoro substituents;

$Ar^3$ is pyridyl optionally substituted with 1 to 4 independently selected halo substituents, or with 1 to 3 substituents independently selected from the group consisting of halo, cyano, hydroxy, -$SCF_3$, $(C_1$-$C_6)$alkyl optionally further substituted with 1 to 6 fluoro substituents, and $(C_1$-$C_6)$alkoxy optionally further substituted with 1 to 6 fluoro substituents;

$Ar^4$ is pyridyl optionally substituted with 1 to 4 independently selected halo substituents, or with 1 to 3 substituents independently selected from the group consisting of halo, cyano, hydroxy, $(C_1$-$C_6)$alkyl optionally further substituted with 1 to 6 fluoro substituents, $(C_1$-$C_6)$alkoxy optionally further substituted with 1 to 6 fluoro substituents, $(C_1$-$C_6)$alkylthio optionally further substituted with 1 to 6 fluoro substituents, $(C_1$-$C_6)$alkylsulfonyl, $(C_1$-$C_6)$alkyl-C(O)—, and $(C_1$-$C_6)$alkyl-NHC(O)—;

$Het^1$ is a heterocycle, linked through either carbon or nitrogen, selected from the group consisting of pyrazolyl, pyrazolinyl, pyrazolidinyl, imidazolyl, imidazolinyl, imidazolidinyl, thiazolyl, thiazolinyl, thiazolidinyl, oxazolyl, oxazolinyl, oxazolidinyl, pyrrolyl, pyrrolinyl, pyrrolidinyl, 1,2,4-triazolyl, 1,3,4-triazolyl, piperidyl, tetrahydropyridyl, dihydropyridyl, piperazinyl, tetrahydropyrazinyl, dihydropyrazinyl, hexahydropyrimidyl, tetrahydropyrimidyl, dihydropyrimidyl, morpholinyl, thiomorpholinyl, homomorpholinyl, homopiperidinyl, indazolyl, indazolinyl, benzimidazolyl, benzimidazolinyl, benzothiazolyl, benzothiazolinyl, benzoxazolyl, benzoxazolinyl, indolyl, indolinyl, isoindolyl, isoindolinyl, benzotriazolyl, dihydroquinolinyl, tetrahydroquinolinyl, dihydroisoquinolinyl, tetrahydroisoquinolinyl, dihydroquinazolinyl, tetrahydroquinazolinyl, dihydroquinoxalinyl, tetrahydroquinoxalinyl, benzoxazinyl, benzothiazinyl, benzazepinyl, and benzoxazepinyl, any one of which may be optionally substituted on carbon atoms of the heterocyclic ring with 1 to 2 oxo substituents, and independently optionally substituted on either carbon or nitrogen atoms of the heterocyclic ring, with 1 to 2 substituents independently selected from the group consisting of $(C_1$-$C_6)$ alkyl optionally further substituted with 1 to 6 fluoro substituents, $Ph^1$-$(C_0$-$C_3)$alkyl optionally further substituted on the alkyl moiety with 1 to 6 fluoro substituents, and $Ar^3$—$(C_0$-$C_3)$alkyl optionally further substituted on the alkyl moiety with 1 to 6 fluoro substituents, or two adjacent substituents taken together with the heterocyclic ring atoms to which they are attached form a 5- or 6-membered saturated or partially saturated ring;

$Ph^1$ is phenyl optionally substituted with 1 to 5 independently selected halo substituents, or with 1 to 3 substituents independently selected from the group consisting of halo, cyano, —$SCF_3$, hydroxy, $(C_1$-$C_6)$alkyl optionally further substituted with 1 to 6 fluoro substituents, and $(C_1$-$C_6)$alkoxy optionally further substituted with 1 to 6 fluoro substituents; and $Ph^3$ is phenyl optionally substituted with 1 to 5 independently selected halo substituents, or with 1 to 3 substituents independently selected from the group consisting of halo, cyano, hydroxy, $(C_1$-$C_6)$alkyl optionally further substituted with 1 to 6 fluoro substituents, $(C_1$-$C_6)$alkoxy optionally further substituted with 1 to 6 fluoro substituents, $(C_1$-$C_6)$alkylthio optionally further substituted with 1 to 6 fluoro substituents, $(C_1$-$C_6)$alkylsulfonyl, $(C_1$-$C_6)$alkyl-C(O)—, and $(C_1$-$C_6)$alkyl-NHC(O)—;

or a pharmaceutically acceptable salt thereof.

* * * * *

UNITED STATES PATENT AND TRADEMARK OFFICE
CERTIFICATE OF CORRECTION

PATENT NO. : 8,420,631 B2  
APPLICATION NO. : 11/995344  
DATED : April 16, 2013  
INVENTOR(S) : Allen et al.

Page 1 of 1

It is certified that error appears in the above-identified patent and that said Letters Patent is hereby corrected as shown below:

Title page, Column 2 (Abstract), Line 1, Delete "6-substituted 2,3,4,5" and insert -- 6-substituted-2,3,4,5 --, therefor.

In the Claims:

Column 87, Line 64, In Claim 2, before "moiety" insert -- alkyl --.

Column 88, Line 58, In Claim 2, delete "fluro" and insert -- fluoro --, therefor.

Column 90, Line 15 (Approx.), In Claim 3, delete "pyrrolyl furanyl," and insert -- pyrrolyl, furanyl, --, therefor.

Signed and Sealed this  
Sixteenth Day of July, 2013

Teresa Stanek Rea  
*Acting Director of the United States Patent and Trademark Office*